(12) United States Patent
Hanai et al.

(10) Patent No.: US 7,241,568 B2
(45) Date of Patent: Jul. 10, 2007

(54) ANTI-FIBROBLAST GROWTH FACTOR-8 MONOCLONAL ANTIBODY

(75) Inventors: Nobuo Hanai, Princeton, NJ (US); Motoo Yamasaki, Tokyo (JP); Akiko Furuya, Machida (JP); Akira Tanaka, Tochigi (JP); Kenya Shitara, Machida (JP); Naoki Shimada, Machida (JP); Kazuyasu Nakamura, Machida (JP); Maiko Hirota, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 475 days.

(21) Appl. No.: 10/434,469

(22) Filed: May 9, 2003

(65) Prior Publication Data

US 2004/0091480 A1      May 13, 2004

Related U.S. Application Data

(60) Continuation-in-part of application No. 09/876,040, filed on Jun. 8, 2001, now abandoned, which is a division of application No. 09/326,590, filed on Jun. 7, 1999, now Pat. No. 6,310,184, which is a division of application No. 08/832,236, filed on Apr. 3, 1997, now Pat. No. 5,952,472.

(30) Foreign Application Priority Data

Apr. 3, 1996     (JP)     .................. P. 8-81754

(51) Int. Cl.
*A61K 39/00* (2006.01)
*A61K 39/395* (2006.01)

(52) U.S. Cl. .................... 435/6; 424/130.1; 424/142.1; 424/155.1

(58) Field of Classification Search ............. 424/130.1, 424/133.1, 138.1, 141.1, 142.1, 155.1, 156.1, 424/158.1
See application file for complete search history.

(56) References Cited

U.S. PATENT DOCUMENTS

| 5,225,539 | A | 7/1993 | Winter ..................... 530/387.3 |
| 5,585,089 | A | 12/1996 | Queen et al. ............. 424/133.1 |
| 5,693,761 | A | 12/1997 | Queen et al. ............. 536/23.53 |
| 5,693,762 | A | 12/1997 | Queen et al. ............. 530/387.3 |
| 5,952,472 | A | 9/1999 | Hanai et al. .............. 530/387.1 |
| 6,180,370 | B1 | 1/2001 | Queen et al. ............. 435/69.6 |
| 6,310,184 | B1 | 10/2001 | Hanai et al. .............. 530/387.1 |
| 6,331,415 | B1 | 12/2001 | Cabilly et al. ............. 435/69.6 |

FOREIGN PATENT DOCUMENTS

| EP | 0 799 835 A2 | 10/1997 |
| EP | 0799835 A2 * | 10/1997 |
| EP | 0 882 794 A2 | 12/1998 |
| EP | 1 422 243 A1 | 5/2004 |
| EP | 1422243 A1 * | 5/2004 |
| JP | 2001-46066 | 2/2001 |
| WO | WO 92/12734 | 8/1992 |
| WO | 9503831 | 2/1995 |
| WO | WO 03/002608 | 1/2003 |
| WO | WO 2003002608 A1 * | 1/2003 |

OTHER PUBLICATIONS

Dorin et al. (Oncogene 1999; 18: 2755-2761).*
Valve et al. (In. J. Cancer 2000, 88: 718-725).*
Freshney (Culture of Animal Cells, A Manual of Basic Technique, Alan R. Liss, Inc., 1983, New York, p. 4.*
Dermer (Bio/Technology, 1994, 12:320).*
Johnstone and Thorpe (Immunochemistry in Practice, Blackwell Scientific Publications, Oxford), 1987.*
Kimmel et al (J. Neurosurg., 66:161-171), 1987.*
Hird et al (Genes and Cancer, Carney et al., Ed., John Wiley and Sons, Ltd), 1990.*
Freshney (Culture of Animal Cells, A Manual of Basic Technique, Alan R. Liss, Inc., New York), 1983.*
Jain (Scientific American Jul. 1994).*
Gura (Science, v278, 1997, pp. 1041-1042).*
Dermer (Bio/Technology, 12:320), 1994.*
Gura (Science, 278:1041-1042), 1997.*
Jain (Sci. Am., 271:58-65), 1994.*
Curti (Crit. Rev. in Oncology/Hermatology, 14:29-39), 1993.*
Hartwell et al (Science, 278:1064-1068), 1997.*
Sato et al (J. Steroid Biochem. Molec. Bio., 1993, 47 [1-6] 91-98).*
Koga et al(J. Steroid Biochem. Molec. Biol., 1995, 54 [½] 1-6).*
Sevier et al (Clin. Chem., 1981, 27(11) 1797-1806).*
Dermer (Bio/Technology, 12:230).
Gura (Science, 278:1041-1042).
Jain (Sci. Am., 271:58-65).
Curti (Crit. Rev. in Oncology/Hamatology, 14:29-39).
Johnstone and Thorpe (Immunochemistry in Practice, Blackwell Scientific Publications, Oxford) 1987.
Kimmel et al (J. Neurosurg., 66: 161-171) 1987.
Hird et al (Genes and Cancer, Carney et al., Ed., John Wiley and Sons, Ltd.) 1990 O:\bjs\249\249-310\7.pdf.
Freshney (Culture of Animal Cells, A Manual of Basic Technique, Alan R. Liss, Inc., NY) 1983.
Prac. Natl. Acad. Sci. USA, vol. 89, pp. 8928-8932, Oct. 1992, Biochemistry, Cloning and characterization of an androgen-induced growth factor essential for the androgen-dependent growth of mouse mammary carcinoma cells, Tanaka et al.
FEBS LETTERS 3663 (1995) 226-230, Federation of European Biochemical Societies, "Human androgen-induced growth factor in prostate and breast cancer cells: its molecular cloning and growth properties" Tanaka et al.

(Continued)

*Primary Examiner*—Shanon Foley
*Assistant Examiner*—Brandon Fetterolf
(74) *Attorney, Agent, or Firm*—Nixon & Vanderhye P.C.

(57) ABSTRACT

A method for preventing or treating a disease, comprising administering to human or animal in need of such prevention or treatment an effective amount of a monoclonal antibody which specifically binds to FGF-8 and inhibits FGF-8 activity.

26 Claims, 21 Drawing Sheets

OTHER PUBLICATIONS

MacArthur et al 1995 Cell Growth and Differentiation, vol. 6, pp. 817-825 FGF-8 Isoforms Differ in NIH3T3.

Roitt Essential IMmunoloogy 6th Edition Production of Effectors pp. 107-109 The monoclonal antibody revolution.

Lorenzi et al, "Expression Cloning Development . . . ", Oncogene vol. 10 No. 10, 1995, pp. 2051-2055.

Tanaka et al, "High Frequency of Fibroblast Growth Factor . . . ", Cancer Research vol. 58, No. 10, May 1998, pp. 2053-2056.

Sato et al. J Steroid Biochem Molec. Bio, 1993, 47 (1-6) 91-98.

Koga et al. J Steroid Biochem Molec. Bio, 1995, 54 (½) 1-6.

Seiver et al (Clin Chem 1981, 27(11) 1797-1806).

Yoshida et al (Agro Biol Chem 53(4) 1095-1101 (1989).

Lorenzi et al, "Expression Cloning Development . . . ", Oncogene vol. 10 No. 10, 1995, pp. 2051-2055.

Tanaka et al, "High Frequency of Fibroblast Growth Factor . . . ", Cancer Research vol. 58, No. 10, May 1998, pp. 2053-2056.

Prac. Natl. Acad. Sci. USA, vol. 89, pp. 8928-8932, Oct. 1992, Biochemistry, "Cloning and characterization of an androgen-induced growth factor essential for the androgen-dependent growth of mouse mammary carcinoma cells", Tanaka et al.

FEBS LETTERS 3663 (1995) 226-230, Federation of European Biochemical Societies, "Human androgen-induced growth factor in prostate and breast cancer cells: its molecular cloning and growth properties", Tanaka et al.

MacArthur et al 1995 Cell Growth and Differentiation, vol. 6 pp. 817-825 FGF-8 Isoforms Differ in NIH3T3.

Roitt Essential Immunology 6th Edition Production of Effectors pp. 107-109 The Monoclonal antibody revolution.

VJ Gnanapragasam et al, British Journal of Cancer, 2003, 88, pp. 1432-1438.

Morrison et al, Proc. Natl. Acad. Sci., Nov. 1984, vol. 81, pp. 6851-6855.

Jones et al, Nature, vol. 321, May 29, 1986, pp. 522-525.

Reichmann et al, Nature, vol. 332, Mar. 24, 1988, pp. 323-327.

Lorenzi et al, Oncogene (1995), vol. 10, pp. 2051-2055.

Tanaka et al, Cancer Research, 1998, vol. 58, No. 10, pp. 2053-2056.

Vaughan et al, 1998, vol. 16, No. 6, pp. 535-539.

Supplementary European Search Report dated Mar. 23, 2005 issued in EP 02 74 3765.

\* cited by examiner

SEQUENCE LISTING

```
<160> NUMBER OF SEQ ID NOS: 43

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: synthetic
      peptide from FGF-8

<400> SEQUENCE: 1

Gln Val Thr Val Gln Ser Ser Pro Asn Phe Thr Gln His Val Arg Glu
 1               5                  10                  15

Gln Ser Leu Val Thr Asp Gln Leu Cys
            20                  25

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: reference
      antigen

<400> SEQUENCE: 2

Cys Ala Thr Ala Ala Asp Gln Glu Lys Asn Pro Glu Gly Asp Gly
 1               5                  10                  15

<210> SEQ ID NO 3
```

```
<211> LENGTH: 420
<212> TYPE: DNA
<213> ORGANISM: Mus musculus
<220> FEATURE:
<221> NAME/KEY: CDS
<222> LOCATION: (1)..(420)

<400> SEQUENCE: 3 atg gaa tgg atc tgg atc ttt ctc ttc ttc ctc tca gga act aca ggt      48
Met Glu Trp Ile Trp Ile Phe Leu Phe Phe Leu Ser Gly Thr Thr Gly
 1               5                  10                  15 gtc tac tcc cag gtt cag ctg cag cag tct gga gct gag gtg gcg agg      96
Val Tyr Ser Gln Val Gln Leu Gln Gln Ser Gly Ala Glu Val Ala Arg
             20                  25                  30 ccc ggg gct tca gtg aaa ctg tcc tgc aag gct tct ggc tac acc ttc     144
Pro Gly Ala Ser Val Lys Leu Ser Cys Lys Ala Ser Gly Tyr Thr Phe
         35                  40                  45 act gac tac tat cta aac tgg gtg aag cag agg tct gga cag ggc ctt     192
Thr Asp Tyr Tyr Leu Asn Trp Val Lys Gln Arg Ser Gly Gln Gly Leu
     50                  55                  60 gag tgg att gga gag att gat cct gga agt gat agt ata tat tat aat     240
Glu Trp Ile Gly Glu Ile Asp Pro Gly Ser Asp Ser Ile Tyr Tyr Asn
 65                  70                  75                  80 gaa aac ttg gag ggc agg gcc aca ctg act gca gac aaa tcc tcc agc     288
Glu Asn Leu Glu Gly Arg Ala Thr Leu Thr Ala Asp Lys Ser Ser Ser
                 85                  90                  95 aca gcc tac atg cag ctc aac agc ctg aca tct gag gac tct gca gtc     336
Thr Ala Tyr Met Gln Leu Asn Ser Leu Thr Ser Glu Asp Ser Ala Val
            100                 105                 110 tat ttc tgt gca aga tat ggg tat tct aga tac gac gta agg ttt gtc     384
Tyr Phe Cys Ala Arg Tyr Gly Tyr Ser Arg Tyr Asp Val Arg Phe Val
        115                 120                 125 tac tgg ggc caa ggg act ctg gtc act gtc tct aca                     420
Tyr Trp Gly Gln Gly Thr Leu Val Thr Val Ser Thr
    130                 135                 140

<210> SEQ ID NO 4
<211> LENGTH: 140
<212> TYPE: PRT
<213> ORGANISM: Mus musculus

<400> SEQUENCE: 4

Met Glu Trp Ile Trp Ile Phe Leu Phe Phe Leu Ser Gly Thr Thr Gly
 1               5                  10                  15

Val Tyr Ser Gln Val Gln Leu Gln Gln Ser Gly Ala Glu Val Ala Arg
             20                  25                  30

Pro Gly Ala Ser Val Lys Leu Ser Cys Lys Ala Ser Gly Tyr Thr Phe
         35                  40                  45

Thr Asp Tyr Tyr Leu Asn Trp Val Lys Gln Arg Ser Gly Gln Gly Leu
     50                  55                  60

Glu Trp Ile Gly Glu Ile Asp Pro Gly Ser Asp Ser Ile Tyr Tyr Asn
 65                  70                  75                  80

Glu Asn Leu Glu Gly Arg Ala Thr Leu Thr Ala Asp Lys Ser Ser Ser
                 85                  90                  95

Thr Ala Tyr Met Gln Leu Asn Ser Leu Thr Ser Glu Asp Ser Ala Val
            100                 105                 110

Tyr Phe Cys Ala Arg Tyr Gly Tyr Ser Arg Tyr Asp Val Arg Phe Val
        115                 120                 125

Tyr Trp Gly Gln Gly Thr Leu Val Thr Val Ser Thr
    130                 135                 140
```

<210> SEQ ID NO 5
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 5

| | | | | | | | | | | | | | | | | |
|---|---|---|---|---|---|---|---|---|---|---|---|---|---|---|---|---|
| atg | aag | ttg | cct | gtt | agg | ctg | ttg | gtg | ctg | atg | ttc | tgg | att | cct | gct | 48 |
| Met | Lys | Leu | Pro | Val | Arg | Leu | Leu | Val | Leu | Met | Phe | Trp | Ile | Pro | Ala | |
| 1 | | | | 5 | | | | | 10 | | | | | 15 | | |
| tcc | agg | agt | gat | gtt | ttg | atg | acc | caa | act | cca | ctc | tcc | ctg | cct | gtc | 96 |
| Ser | Arg | Ser | Asp | Val | Leu | Met | Thr | Gln | Thr | Pro | Leu | Ser | Leu | Pro | Val | |
| | | | 20 | | | | | 25 | | | | | 30 | | | |
| agt | ctt | gga | gat | caa | gcc | tcc | atc | tct | tgc | aga | tct | agt | cag | agt | ctt | 144 |
| Ser | Leu | Gly | Asp | Gln | Ala | Ser | Ile | Ser | Cys | Arg | Ser | Ser | Gln | Ser | Leu | |
| | | 35 | | | | | 40 | | | | | 45 | | | | |
| gta | cat | agt | aat | gga | aga | acc | tat | tta | gaa | tgg | tac | ctg | cag | aaa | cct | 192 |
| Val | His | Ser | Asn | Gly | Arg | Thr | Tyr | Leu | Glu | Trp | Tyr | Leu | Gln | Lys | Pro | |
| 50 | | | | | 55 | | | | | 60 | | | | | | |
| ggc | cag | tca | cca | aag | gtc | ctg | atc | tac | aaa | gtt | tcc | aac | cga | att | tct | 240 |
| Gly | Gln | Ser | Pro | Lys | Val | Leu | Ile | Tyr | Lys | Val | Ser | Asn | Arg | Ile | Ser | |
| 65 | | | | | 70 | | | | | 75 | | | | | 80 | |
| ggg | gtc | cca | gac | agg | ttc | agt | ggc | agt | gga | tca | ggg | aca | gat | ttc | aca | 288 |
| Gly | Val | Pro | Asp | Arg | Phe | Ser | Gly | Ser | Gly | Ser | Gly | Thr | Asp | Phe | Thr | |
| | | | | 85 | | | | | 90 | | | | | 95 | | |
| ctc | aaa | atc | agc | aga | gtg | gag | gct | gag | gat | ctg | gga | gtt | tat | ttc | tgc | 336 |
| Leu | Lys | Ile | Ser | Arg | Val | Glu | Ala | Glu | Asp | Leu | Gly | Val | Tyr | Phe | Cys | |
| | | | 100 | | | | | 105 | | | | | 110 | | | |
| ttt | cag | ggt | tca | cat | gtt | ccg | tac | acg | ttc | gga | ggg | ggg | acc | aag | ctg | 384 |
| Phe | Gln | Gly | Ser | His | Val | Pro | Tyr | Thr | Phe | Gly | Gly | Gly | Thr | Lys | Leu | |
| | | 115 | | | | | 120 | | | | | 125 | | | | |
| gaa | ata | aaa | | | | | | | | | | | | | | 393 |
| Glu | Ile | Lys | | | | | | | | | | | | | | |
| | | 130 | | | | | | | | | | | | | | |

<210> SEQ ID NO 6
<211> LENGTH: 131
<212> TYPE: PRT
<213> ORGANISM: Mus musculus

<400> SEQUENCE: 6

Met Lys Leu Pro Val Arg Leu Leu Val Leu Met Phe Trp Ile Pro Ala
1               5                   10                  15

Ser Arg Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Arg Thr Tyr Leu Glu Trp Tyr Leu Gln Lys Pro
50                  55                  60

Gly Gln Ser Pro Lys Val Leu Ile Tyr Lys Val Ser Asn Arg Ile Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Gly Ser His Val Pro Tyr Thr Phe Gly Gly Gly Thr Lys Leu
        115                 120                 125

```
Glu Ile Lys
    130

<210> SEQ ID NO 7
<211> LENGTH: 5
<212> TYPE: PRT
<213> ORGANISM: Mus musculus

<400> SEQUENCE: 7

Asp Tyr Tyr Leu Asn
 1               5

<210> SEQ ID NO 8
<211> LENGTH: 17
<212> TYPE: PRT
<213> ORGANISM: Mus musculus

<400> SEQUENCE: 8

Glu Ile Asp Pro Gly Ser Asp Ser Ile Tyr Tyr Asn Glu Asn Leu Glu
 1               5                  10                  15

Gly

<210> SEQ ID NO 9
<211> LENGTH: 12
<212> TYPE: PRT
<213> ORGANISM: Mus musculus

<400> SEQUENCE: 9

Tyr Gly Tyr Ser Arg Tyr Asp Val Arg Phe Val Tyr
 1               5                  10

<210> SEQ ID NO 10
<211> LENGTH: 16
<212> TYPE: PRT
<213> ORGANISM: Mus musculus

<400> SEQUENCE: 10

Arg Ser Ser Gln Ser Leu Val His Ser Asn Gly Arg Thr Tyr Leu Glu
 1               5                  10                  15

<210> SEQ ID NO 11
<211> LENGTH: 7
<212> TYPE: PRT
<213> ORGANISM: Mus musculus

<400> SEQUENCE: 11

Lys Val Ser Asn Arg Ile Ser
 1               5

<210> SEQ ID NO 12
<211> LENGTH: 9
<212> TYPE: PRT
<213> ORGANISM: Mus musculus

<400> SEQUENCE: 12

Phe Gln Gly Ser His Val Pro Tyr Thr
 1               5

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: pKM1334H7-1
```

```
                                primer

<400> SEQUENCE: 13
ctgaattcgc ggccgctagt cc                                              22

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: pKM1334H7-1
      primer

<400> SEQUENCE: 14
atgggccctt ggtggaggct gtagagacag tgaccagag                            39

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: pKM1334L7-1
      primer

<400> SEQUENCE: 15
ctgaattcgc ggccgctgct gt                                              22

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: pKM1334L7-1
      primer

<400> SEQUENCE: 16
atcgtacgtt ttatttccag cttggtcc                                        28

<210> SEQ ID NO 17
<211> LENGTH: 25
<212> TYPE: PRT
<213> ORGANISM: Homo sapiens

<400> SEQUENCE: 17

Gln Val Thr Val Gln Ser Ser Pro Asn Phe Thr Gln His Val Arg Glu
  1               5                  10                  15

Gln Ser Leu Val Thr Asp Gln Leu Cys
            20                  25

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: VH
      synthetic peptide

<400> SEQUENCE: 18

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45
```

```
Gly Glu Ile Asp Pro Gly Ser Asp Ser Ile Tyr Tyr Asn Glu Asn Leu
    50                  55                  60

Glu Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Ser
        115                 120

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: VL
      synthetic peptide

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Ser
                20                  25                  30

Asn Gly Arg Thr Tyr Leu Glu Trp Tyr Leu Gln Lys Pro Gly Gln Ser
            35                  40                  45

Pro Gln Leu Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
            100                 105                 110

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: VH
      synthetic peptide

<400> SEQUENCE: 20

Gln Val Gln Leu Val Gln Ser Gly Ala Glu Val Ala Arg Pro Gly Ala
1               5                   10                  15

Ser Val Lys Val Ser Cys Lys Ala Ser Gly Tyr Thr Phe Thr Asp Tyr
                20                  25                  30

Tyr Leu Asn Trp Val Arg Gln Arg Ser Gly Gln Gly Leu Glu Trp Ile
            35                  40                  45

Gly Glu Ile Asp Pro Gly Ser Asp Ser Ile Tyr Tyr Asn Glu Asn Leu
    50                  55                  60

Glu Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Gly Tyr Ser Arg Tyr Asp Val Arg Phe Val Tyr Trp Gly
            100                 105                 110
```

```
Gln Gly Thr Leu Val Thr Val Ser Ser
        115                 120

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: VL
      synthetic peptide

<400> SEQUENCE: 21

Asp Val Val Met Thr Gln Ser Pro Leu Ser Leu Pro Val Ser Leu Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Lys Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 22
<211> LENGTH: 141
<212> TYPE: DNA
<213> ORGANISM: Artificial Sequence
<220> FEATURE:
<223> OTHER INFORMATION: Description of Artificial Sequence: antibody V
      region segment

<400> SEQUENCE: 22
caggaaacag ctatgacgaa ttcgcggccg cacactgact ctaaccatgg aatggatctg      60
gatctttctc ttcttcctct caggaactac aggtgtctac tcccaggtgc agctggtgca    120
gtctggggct gaggtgaaga a                                              141

<210> SEQ ID NO 23
<211> LENGTH: 141
<212> TYPE: DNA
<213> ORGANISM: Artificial Sequence
<220> FEATURE:
<223> OTHER INFORMATION: Description of Artificial Sequence: antibody V
      region segment

<400> SEQUENCE: 23
aggatcgatc tctcccatcc actcaagccc ttgtccgggg gcctgccgca cccagtttag      60
atagtagtca gtgaaggtgt atccagaagc cttgcaggag accttcactg aggcccccggg   120 cttcttcacc tcagccccag a                                              141

<210> SEQ ID NO 24
<211> LENGTH: 141
<212> TYPE: DNA
<213> ORGANISM: Artificial Sequence
<220> FEATURE:
<223> OTHER INFORMATION: Description of Artificial Sequence: antibody V
      region segment

<400> SEQUENCE: 24
```

```
ggatgggaga gatcgatcct ggaagtgata gtatatatta taatgaaaac ttggagggca    60
gagtcacgat taccgcggac acatccacga gcacagccta catggagctg agcagcctga   120
gatctgagga cacggccgtg t                                              141

<210> SEQ ID NO 25
<211> LENGTH: 141
<212> TYPE: DNA
<213> ORGANISM: Artificial Sequence
<220> FEATURE:
<223> OTHER INFORMATION: Description of Artificial Sequence: antibody V
      region segment

<400> SEQUENCE: 25
gttttcccag tcacgactag tgggcccttg gtggaggctg aggagacggt gaccagggtt    60
ccctggcccc agtagacaaa ccttacgtcg tatctagaat acccatatct cgcacagtaa   120
tacacggccg tgtcctcaga t                                              141

<210> SEQ ID NO 26
<211> LENGTH: 141
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 26
caggaaacag ctatgacgaa ttcgcggccg cacactgact ctaaccatgg aatggatctg    60
gatctttctc ttcttcctct caggaactac aggtgtctac tcccaggtgc agctggtgca   120
gtctggggct gaggtggcga g                                              141

<210> SEQ ID NO 27
<211> LENGTH: 141
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 27
aggatcgatc tctccaatcc actcaagccc ttgtccagac ctctgccgca cccagtttag    60
atagtagtca gtgaaggtgt atccagaagc cttgcaggag accttcactg aggccccggg   120
cctcgccacc tcagccccag a                                              141

<210> SEQ ID NO 28
<211> LENGTH: 141
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 28
ggattggaga gatcgatcct ggaagtgata gtatatatta taatgaaaac ttggagggca    60
gagtcacgat taccgcggac acatccacga gcacagccta catggagctg agcagcctga   120
gatctgagga cacggccgtg t                                              141

<210> SEQ ID NO 29
<211> LENGTH: 141
<212> TYPE: DNA
```

```
<213> ORGANISM: Artificial Sequence
<220> FEATURE:
<223> OTHER INFORMATION: Description of Artificial Sequence: item 1(1)
      of Example 4 oligo

<400> SEQUENCE: 29
gttttcccag tcacgactag tgggcccttg gtggaggctg aggagacggt gaccagggtt    60
ccctggcccc agtagacaaa ccttacgtcg tatctagaat acccatatct cgcacagaaa   120
tacacggccg tgtcctcaga t                                             141

<210> SEQ ID NO 30
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 30
caggaaacag ctatgacgaa ttcaggttgc ctcctcaaaa tgaagttgcc tgttaggctg    60
ttggtgctga tgttctggat tcctgcttcc aggagtgata tcgtgatgac tcagtctcca   120
ctctccctgc                                                          130

<210> SEQ ID NO 31
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 31
agactggcct ggcttctgca ggtaccattc taaataggtt cttccattac tatgtacaag    60
actctgacta gatctgcagg agatggaggc cggctctcca ggggtgacgg gcagggagag   120
tggagactga                                                          130

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 32
tgcagaagcc aggccagtct ccacagctcc tgatctataa agtttccaac cgaatttctg    60 ggtcccaga caggttcagt ggcagtggat ccgggacaga tttcacactg aaaatcagca   120
gggtggaggc                                                          130

<210> SEQ ID NO 33
<211> LENGTH: 129
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 33
gttttcccag tcacgactag tcgtacgttt gatttccacc ttggtccctt ggccgaacgt    60
gtacggaaca tgtgaaccct gaaagcagta ataaaccccg acgtcctcag cctccaccct   120
```

```
gctgattttt                                                                 129

<210> SEQ ID NO 34
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 34
caggaaacag ctatgacgaa ttcaggttgc ctcctcaaaa tgaagttgcc tgttaggctg          60
ttggtgctga tgttctggat tcctgcttcc aggagtgatg ttgtgatgac tcagtctcca         120
ctctccctgc                                                                130

<210> SEQ ID NO 35
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 35
agactggcct ggcttctgca ggtaccattc taaataggtt cttccattac tatgtacaag          60
actctgacta gatctgcagg agatggaggc cggctctcca agactgacgg gcagggagag         120
tggagactga                                                                130

<210> SEQ ID NO 36
<211> LENGTH: 130
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 36
tgcagaagcc aggccagtct ccaaaggtcc tgatctataa agtttccaac cgaatttctg          60
gggtcccaga caggttcagt ggcagtggat ccgggacaga tttcacactg aaaatcagca         120
gggtggaggc                                                                130

<210> SEQ ID NO 37
<211> LENGTH: 129
<212> TYPE: DNA
<213> ORGANISM: Artificial Sequence
<220> FEATURE:
<223> OTHER INFORMATION: Description of Artificial Sequence: item 1(1)
      of Example 4 oligo

<400> SEQUENCE: 37
gttttcccag tcacgactag tcgtacgttt gatttccacc ttggtccctt ggccgaacgt          60
gtacggaaca tgtgaaccct gaaagcagaa ataaaccccg acgtcctcag cctccaccct         120
gctgattttt                                                                129

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: pKM1334LV6
      primer
```

<400> SEQUENCE: 38
atggtacctg cagaagccag gccagtctcc acaggtcct        39

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence:
     pKM1334LV2-2 primer

<400> SEQUENCE: 39
atggtacctg cagaagccag gccagtctcc acagctcct        39

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: LV.4-3 of
     KM8035

<400> SEQUENCE: 40

Asp Ile Val Met Thr Gln Ser Pro Leu Ser Leu Pro Val Ser Leu Gly
  1               5                  10                  15

Glu Pro Ala Ser Ile Ser Cys Arg Ser Ser Gln Ser Leu Val His Ser
             20                  25                  30

Asn Gly Arg Thr Tyr Leu Glu Trp Tyr Leu Gln Lys Pro Gly Gln Ser
         35                  40                  45

Pro Gln Val Leu Ile Tyr Lys Val Ser Asn Arg Ile Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Ser His Val Pro Tyr Thr Phe Gly Gln Gly Thr Lys Val Glu Ile Lys
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: LV.3-1 of
     VL of KM8036

<400> SEQUENCE: 41

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
             20                  25                  30

Asn Gly Arg Thr Tyr Leu Glu Trp Tyr Leu Gln Lys Pro Gly Gln Ser
         35                  40                  45

Pro Gln Val Leu Ile Tyr Lys Val Ser Asn Arg Ile Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Ser His Val Pro Tyr Thr Phe Gly Gln Gly Thr Lys Val Glu Ile Lys

```
                     100             105             110

<210> SEQ ID NO 42
<211> LENGTH: 121
<212> TYPE: PRT
<213> ORGANISM: Mus musculus

<400> SEQUENCE: 42

Gln Val Gln Leu Gln Gln Ser Gly Ala Glu Val Ala Arg Pro Gly Ala
 1               5                  10                  15

Ser Val Lys Leu Ser Cys Lys Ala Ser Gly Tyr Thr Phe Thr Asp Tyr
            20                  25                  30

Tyr Leu Asn Trp Val Lys Gln Arg Ser Gly Gln Gly Leu Glu Trp Ile
         35                  40                  45

Gly Glu Ile Asp Pro Gly Ser Asp Ser Ile Tyr Tyr Asn Glu Asn Leu
     50                  55                  60

Glu Gly Arg Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Thr
            115                 120

<210> SEQ ID NO 43
<211> LENGTH: 112
<212> TYPE: PRT
<213> ORGANISM: Mus musculus

<400> SEQUENCE: 43

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
         35                  40                  45

Pro Lys Val Leu Ile Tyr Lys Val Ser Asn Arg Ile Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                 85                  90                  95

Ser His Val Pro Tyr Thr Phe Gly Gly Gly Thr Lys Leu Glu Ile Lys
            100                 105                 110
```

ANTI-FIBROBLAST GROWTH FACTOR-8 MONOCLONAL ANTIBODY

This application is a continuation-in-part of Ser. No. 09/876,040 filed Jun. 8, 2001, now abandoned, which is a division of Ser. No. 09/326,590 filed Jun. 7,1999, now U.S. Pat. No. 6,310,184, which is a division of Ser. No. 08/832,236 filed Apr. 3, 1997, now U.S. Pat. No. 5,952,472, the entire contents of which are incorporated herein by reference.

FIELD OF THE INVENTION

The present invention relates to a monoclonal antibody which specifically binds to fibroblast growth factor-8, has a neutralization activity, namely it inhibits activity of fibroblast growth factor-8, and therefore is useful for the morbid state analysis and treatment of human tumor cells grown through induction by fibroblast growth factor-8.

BACKGROUND OF THE INVENTION

Androgen induced growth factor (AIGF) is a factor isolated in 1992 from a culture supernatant of a mouse mammary tumor cell line SC-3 [Shionogi Carcinoma-3: *J. Steroid Biochem.*, 27, 459 (1987)] which shows sex hormone-dependent growth. AIGF is a growth factor which is induced and produced by androgen stimulation and activates growth of SC-3 cells in an autocrine manner [*Proc. Natl. Acad. Sci.*, 89, 8928–8932, (1992)]. The results of gene cloning efforts revealed that it has a homology of 30 to 40% with the FGF family at the amino acid level, and it was named fibroblast growth factor-8 (hereinafter referred to as "FGF-8"). Thereafter, human FGF-8 was cloned from a human placenta genomic library using mouse FGF-8 as a probe, which coincided with the mouse FGF-8 by a factor of 85% at the nucleotide level and 100% at the amino acid level [*FEBS Letters*, 363, 226 (1995)]. It has been assumed that sex hormone induced growth factors would exhibit an autocrine role in tumors such as prostatic cancer, and breast cancer which show sex hormone-dependent growth, and the isolation and cloning of FGF-8, though in a mouse system, was the first evidence of such a mechanism. It is probable that FGF-8 also plays a role in carcinogenesis and tumor growth in humans by a similar mechanism, but clear evidence has not yet been obtained. However, since expression of FGF-8 m-RNA can be found in several human tumor cell lines of prostatic cancer and breast cancer and enhancement of cell growth can be observed when FGF-8 expressed in CHO cells is added to the culture system of these cell lines or a cell line of fibroblasts [*FEBS Letters*, 363, 226 (1995)], expression of mRNA in various human cancer cell lines such as prostate cancer, breast cancer and ovarian cancer was confirmed [*Cell Growth & Differ.*, 7, 1425 (1996), *Oncogene*, 18, 1053 (1999), *Int. J. Cancer*, 88, 718 (2000)] and FGF-8s presented in human cancer tissues of prostate cancer, breast cancer and ovarian cancer was over-expressed compared to FGF-8s presented in normal tissues [*Cancer Res.*, 58, 2053, *Oncogene*, 18, 2755 (1999), *Oncogene*, 18, 1053 (1999), *Int. J. Cancer*, 88, 718 (2000)], such a possibility has been pointed out that FGF-8 also plays an autocrine and paracrine role on the sex hormone-dependent growth of cancer cells in human. On the other hand, since high frequency expression of FGF-8 has also been observed in various hormone-independent human prostate cancer cells, prostate cancer tissues and breast cancer cells [*Cell Growth & Differ.*, 7, 1425 (1996), *Oncogene*, 18, 2755 (1999), *Oncogene*, 18, 1053 (1999)], there is a high possibility that expression of FGF-8 is controlled by sex hormone independent fashion. Furthermore, since there is a report that antisense DNA for FGF-8 inhibited in vitro and in vivo growth of a hormone-independent prostate cancer cell line [*Oncogene*, 16, 1487 (1998)], the presence of an FGF-8-dependent growth mechanism is also suggested in cancers which lost hormone-dependency.

Based on these facts, antibodies against FGF-8 are effective in analyzing biological function of FGF-8 for cancer cells and also in diagnosing cancer cells such as prostate cancer and breast cancer using an immunological detection method. Furthermore, in neutralizing antibodies which inhibits functions of FGF-8, it is expected that they are useful for analyzing the biological function of FGF-8, diagnosing cancers such as prostate cancer, breast cancer and ovarian cancer and treating sex hormone-dependent cancers and sex hormone-independent cancers.

In consequence, an antibody specific for FGF-8 is useful for the analysis of the role and biological function of FGF-8 in the above-mentioned tumor cells, and also for the diagnosis of prostatic cancer, breast cancer and the like by immunological detection. Also, it appears that the antibody having a neutralization activity would be useful in studying biological activities of FGF-8 and effective in treating the cancers.

To date the isolation of a monoclonal antibody specific for FGF-8 has nor been reported.

SUMMARY OF THE INVENTION

An object of the present invention is to provide a method for preventing or treating a disease, comprising administering to human or animal in need of such prevention or treatment an effective amount of a monoclonal antibody which specifically binds to FGF-8 and inhibits the activity of FGF-8.

The inventors of the present invention have obtained a monoclonal antibody by preparing hybridomas using a partial peptide of FGF-8 as the immunogen, establishing a hybridoma strain capable of producing a monoclonal antibody which specifically binds to the peptide, culturing the hybridoma in a medium or administering it to an animal to induce an ascites tumor and then collecting the resulting culture supernatant or ascitic fluid. A Western blotting test using the monoclonal antibody confirmed that the antibody can bind to FGF-8 protein, when the monoclonal antibody was added to a culture broth of a mouse mammary tumor cell line SC-3 capable of showing sex hormone-dependent growth, and confirmed that the monoclonal antibody can inhibit the FGF-8 activity, namely it neutralizes FGF-8.

Furthermore, the inventors of the present invention obtained antibody H chain cDNA and L chain cDNA from a hybridoma KM1334 (FERM BP-5451) which produces a mouse antibody against FGF-8 belonging to IgG1 subclass, found that the V regions and CDRs were novel amino acid sequences, and expressed and purified an anti-FGF-8 human chimeric antibody and an anti-FGF-8 human CDR-grafted antibody by cloning cDNAs encoding the novel V regions or VH and VL comprising CDRs into an expression vector for animal cell comprising cDNAs encoding CH of a human antibody and L chain C region (CL) of a human antibody to thereby construct a vector for humanized antibody expression and then introducing the vector for expression antibody expression into an animal cell. Thus, the present invention has been accomplished.

These and other objects of the present invention have been attained by a method for preventing or treating a disease, comprising administering to human or animal in need of such prevention or treatment an effective amount of a monoclonal antibody which specifically binds to FGF-8 and inhibits FGF-8 activity.

DETAILED DESCRIPTION OF THE INVENTION

Figure 1:
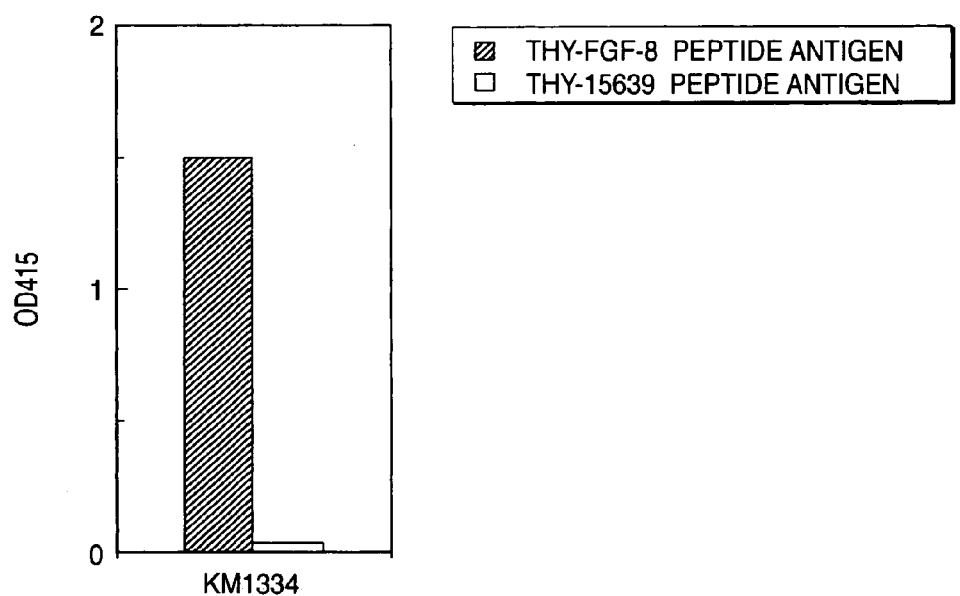
FIG. 1 shows the bindability of anti-FGF-8 monoclonal antibody KM1334 for antigens in an enzyme immunoassay (the term "anti-FGF-8 monoclonal antibody" as used herein means monoclonal antibody which specifically binds to FGF-8). In the drawing, the black quadrangle indicates the bindability for THY-FGF-8 (hereinafter referred to as "THY") peptide antigen, and the white quadrangle for THY-15639 peptide antigen.

The present invention relates to a method for treating diseases such as cancer diseases, comprising administering to human or animal a monoclonal antibody which specifically binds to FGF-8 and has activity of inhibiting FGF-8.

The cancer diseases in the present invention include sex hormone-dependent and -independent neoplastic diseases such as prostate cancer, breast cancer and ovarian cancer.

The monoclonal antibody which specifically binds to FGF-8 and has activity of inhibiting FGF-8 includes a monoclonal antibody produced by a hybridoma, a humanized antibody, the antibody fragment having the binding activity of the antibody, and the like.

The antibody which specifically binds to FGF-8 and has activity of inhibiting FGF-8 specifically includes an antibody which specifically binds to the amino acid sequence at positions 23 to 46 from the N-terminal of the amino acid sequence of FGF-8 and has activity of inhibiting FGF-8.

The monoclonal antibody produced by a hybridoma includes a monoclonal antibody obtained by the preparation method of a hybridoma described below, and specifically includes a monoclonal antibody KM1334 produced by a hybridoma KM1334 (FERM BP-5451).

The humanized antibody includes a human chimeric antibody, a human CDR-grafted antibody and the like.

A human chimeric antibody is an antibody comprising VH and VL of an antibody derived from a non-human animal, and CH and CL of a human antibody. The non-human animal may be any of mouse, rat, hamster, rabbit and the like, so long as a hybridoma can be prepared therefrom.

The human chimeric antibody can be produced by obtaining cDNAs encoding VH and VL from a hybridoma which produces a monoclonal antibody which reacts specifically with FGF-8, inserting the cDNAs into an expression vector for animal cell, having genes encoding a human antibody CH and a human antibody CL to construct a vector for human chimeric antibody expression, and introducing the vector into an animal cell to express the antibody.

Any CH of a human chimeric antibody may be used, so long as it belongs to human immunoglobulin (hIg), and those of hIgG class are preferred, and any one of subclasses further belonging to hIgG such as γ1, γ2, γ3 and γ4 can be used. Also, any CL of a human chimeric antibody can be used, so long as it belongs to hIg, and those of κ class or λ class can be used.

The human chimeric antibody which specifically reacts with FGF-8 (anti-FGF-8 chimeric antibody) includes a human chimeric antibody which comprises complementarity determining region (hereinafter referred to as "CDR") 1, CDR2 and CDR3 of an antibody heavy chain (H chain) variable region (V region) comprising the amino acid sequences represented by SEQ ID NOs:7, 8 and 9, respectively and/or comprises CDR1, CDR2 and CDR3 of an antibody light chain (L chain) variable region (V region) comprising the amino acid sequences represented by SEQ ID NOs:10, 11 and 12, respectively, and preferably a human chimeric antibody in which VH comprises the amino acid sequence represented by SEQ ID NO:42 and/or VL comprises the amino acid sequence represented by SEQ ID NO:43. Examples include antibody KM3034 in which VH of the antibody comprises the amino acid sequence represented by SEQ ID NO:42, CH of the human antibody comprises an amino acid sequence of γ1 subclass, VL of the antibody comprises the amino acid sequence represented by SEQ ID NO:43 and CL of the human antibody comprises an amino acid sequence of κ class.

A human CDR-grafted antibody is an antibody in which CDR amino acid sequences of VH and VL of an antibody derived from a non-human animal are grafted into appropriate positions of VH and VL of an human antibody.

The human CDR-grafted antibody of the present invention can be produced by grafting CDR sequences of VH and VL of an antibody which specifically reacts with FGF-8 of a non-human animal into FRs in VH and VL of any human antibody to construct cDNAs encoding V regions obtained, inserting the cDNAs into an expression vector for animal cell, having DNAs encoding CH and CL of a human antibody to construct a vector for human CDR-grafted antibody expression, and then introducing it into an animal cell to express the antibody.

Any CH of human CDR-grafted antibody may be used, so long as it belongs to hIg, but those of hIgG class are preferred and any one of subclasses further belonging to hIgG such as γ1, γ2, γ3 and γ4 can be used. Also, any CL of human CDR-grafted antibody may be used so long as it belongs to hIg, and those of κ class or λ class can be used.

The human CDR-grafted antibody which specifically reacts with FGF-8 (anti-FGF-8-CDR-grafted antibody) includes a human CDR-grafted antibody which comprises CDR1, CDR2 and CDR3 of an antibody VH comprising the amino acid sequences represented by SEQ ID NOs:7, 8 and 9, respectively and/or comprises CDR1, CDR2 and CDR3 of an antibody VL comprising the amino acid sequences represented by SEQ ID NOs:10, 11 and 12, respectively, preferably a human CDR-grafted antibody in which VH comprises the amino acid sequence represented by SEQ ID NO:18 and/or VL comprises the amino acid sequence represented by SEQ ID NO:19, and more preferably a human CDR-grafted antibody in which VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:18 is substituted with an other amino acid residue, a human CDR-grafted antibody in which VL of the antibody comprises an amino acid sequence in which at least one amino acid residue selected from Ile at position 2, Val at position 3, Thr at position 14, Pro at position 15, Gln at position 50, Leu at position 51 and Tyr at position 92 in the amino acid sequence represented by SEQ ID NO:19 is substituted with an other amino acid residue, and a human CDR-grafted antibody in which VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:18 is substituted with an other amino acid, and wherein VL of the antibody comprises an amino acid sequence in which at least one amino acid residue selected from Ile at position 2, Val at position 3, Thr at position 14, Pro at position 15, Gin at position 50, Leu at position 51 and Tyr at position 92 in the amino acid sequence represented by SEQ ID NO:19 is substituted with an other amino acid. Examples of VH include the amino acid sequence represented by SEQ ID NO:20 in which six residues of Lys at position 12, Lys at position 13, Ala at position 40, Pro at position 41, Met at position 48 and Tyr at position 95 in the amino acid sequence represented by SEQ ID NO:18 are modified with Ala, Arg, Arg, Ser, Ile and Phe, respectively. Examples of VL include the amino acid sequence represented by SEQ ID NO:21 in which six residues of Ile at position 2, Thr at position 14, Pro at position 15, Gin at position 50, Leu at position 51 and Tyr at position 92 in the amino acid sequence represented by SEQ ID NO:19 are modified with Val, Ser, Leu, Lys, Val and Phe, respectively, the amino acid sequence represented by SEQ ID NO:40 in which four residues of Thr at position 14, Pro at position 15, Leu at position 51 and Tyr at position 92 are modified with Ser, Leu, Val and Phe, respectively, and the amino acid sequence represented by SEQ ID NO:41 in which three residues of Ile at position 2, Leu at position 51 and Tyr at position 92 are modified with Val, Val and Phe, respectively.

Examples include a human CDR-grafted antibody in which VH of the antibody comprises the amino acid sequence represented by SEQ ID NO:18 or 20, a human CDR-grafted antibody in which VL of the antibody comprises the amino acid sequence represented by SEQ ID NO:19, 21, 40 or 41, a human CDR-grafted antibody in which VH and VL of the antibody comprise the amino acid sequences represented by SEQ ID NO:18 or 20 and SEQ ID NO:19, 21, 40 or 41, respectively, and the like, preferably a human CDR-grafted antibody in which VH and VL of the antibody comprise the amino acid sequence represented by SEQ ID NO:18 and SEQ ID NO:21, respectively, a human CDR-grafted antibody in which VH and VL of the antibody comprise the amino acid sequence represented by SEQ ID NO:18 and SEQ ID NO:40, respectively, and a human CDR-grafted antibody in which VH and VL of the antibody comprise the amino acid sequence represented by SEQ ID NO:18 and SEQ ID NO:41, respectively.

The fragment having the activity of the antibody includes Fab, Fab', F(ab')$_2$, scFv, diabody, dsFv, a peptide comprising CDR, and the like.

An Fab is an antibody fragment having a molecular weight of about 50,000 and antigen binding activity, in which about a half of the N-terminal side of H chain and the entire L chain, among fragments obtained by treating IgG with a protease, papain (cut at an amino acid residue at position 224 of the H chain), are bound together through a disulfide bond (S—S bond).

The Fab can be obtained by treating a human CDR-grafted antibody of the present invention which specifically reacts with FGF-8, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and antigen binding activity, which is slightly larger than the Fab bound via an S—S bond of the hinge region, among fragments obtained by treating IgG with a protease, pepsin (cut at the amino acid residue at position 234 in H chain).

The F(ab')$_2$ can be obtained by treating an antibody which specifically reacts with FGF-8, with a protease, pepsin. Also, the F(ab')$_2$ can be produced by binding Fab' described below via an thioether bond or an S—S bond.

An Fab' is an antibody fragment having a molecular weight of about 50,000 and antigen binding activity, which is obtained by cutting an S—S bond of the hinge region of the above F(ab')$_2$.

The Fab' can be obtained by treating F(ab')$_2$ which specifically reacts with FGF-8, with a reducing agent, dithiothreitol. Also, the Fab' can be produced by inserting DNA encoding the Fab' of the antibody into an expression vector for prokaryote or an expression vector for eukaryote, and introducing the vector into a prokaryote or eukaryote to express the Fab'.

An scFv is a VH-P-VL or VL P-VH polypeptide in which one chain VH and one chain VL are linked using an appropriate peptide linker (P) of 12 or more residues and which has an antigen-binding activity.

The scFv can be produced by obtaining cDNAs encoding VH and VL of an antibody which specifically reacts with FGF-8, constructing DNA encoding the scFv, inserting the DNA into an expression vector for prokaryote or an expression vector for eukaryote, and then introducing the expression vector into a prokaryote or eukaryote to express the scFv.

A diabody is an antibody fragment in which scFv's having the same or different antigen binding specificity forms a dimer, and has an divalent antigen binding activity to the same antigen or two specific antigen binding activity to different antigens.

The diabody, for example, a divalent diabody which specifically reacts with FGF-8, can be produced by obtaining cDNAs encoding VH and VL of the antibody, constructing DNA encoding scFv having a polypeptide linker of 3 to 10 residues, inserting the DNA into an expression vector for prokaryote or an expression vector for eukaryote, and then introducing the expression vector into a prokaryote or eukaryote to express the diabody.

A dsFV is obtained by binding polypeptides in which one amino acid residue of each of VH and VL is substituted with a cysteine residue via an S—S bond between the cysteine residues. The amino acid residue which is substituted with a cysteine residue can be selected based on a three-dimensional structure estimation of the antibody in accordance with the method shown by Reiter et al. [*Protein Engineering*, 7, 697 (1994)].

The dsFv can be produced by obtaining cDNAs encoding VH and VL of an antibody which specifically reacts with FGF-8, constructing DNA encoding the dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of CDR of VH or VL. A peptide comprising plural CDRs can be prepared by binding them directly or via an appropriate peptide linker.

The peptide comprising CDR can be produced by constructing cDNAs encoding CDRs of VH and VL of an antibody which specifically reacts with FGF-S, inserting the cDNAs into an expression vector for prokaryote or an expression vector for eukaryote, and then by introducing the expression vector into a prokaryote or eukaryote to express the peptide. Also, the peptide comprising CDR can also be produced by a chemical synthesis method such as an Fmoc method (fluorenylmethoxycarbonyl method), a tboc method (t-butyloxycarbonyl method), or the like.

A process for producing the monoclonal antibody which specifically reacts to FGF-8 and inhibits FGF-8, a method for evaluating the activity and a method for using it are explained below.

1. Preparation of Monoclonal Antibody

Monoclonal antibody KM1334 produced by a hybridoma cell line KM1334 (FERM BP-5451), a monoclonal antibody of the present invention, specifically binds to FGF-8.

(1) Preparation of Antigen

As the antigen necessary for the preparation of the anti-FGF-9 monoclonal antibody, FGF-8 producing cells or a cell fraction thereof, or host cells transformed with a DNA fragment which encodes FGF-8, prepared using known techniques by integrating complete or a partial fragment of cDNA which encodes FGF-8 into procaryotic cells (e.g., *Escherichia coli* or the like) or eucaryotic cells (e.g., insect cells, mammal cells or the like) can be used as such or as a protein expressed and purified as a fusion protein, as well as a partial peptide of FGF-8 synthesized using a peptide synthesizer.

In order to increase immunogenicity, the peptide to be used as the antigen is linked to a carrier protein using a cross-linking agent. Examples of the carrier protein include keyhole limpet hemocyanin (hereinafter referred to as "KCLH"), bovine serum albumin (hereinafter referred to as "BSA"), cycloglobulin and the like. Examples of the cross-linking agent include glutaraldehyde, N-(m-maleimidobenzoyloxy)succinimide (hereinafter referred to as "MBS") and the like.

(2) Immunization of Animal and Preparation of Antibody-producing Cells

Animals immunized are not particularly limited as long as a hybridoma can be prepared. Hereinafter, mice and rats are enumerated as specific examples in the present invention.

Mice or rats of 3 to 20 weeks of age are immunized with the antigen prepared by the method of (1), and antibody-producing cells are collected from the spleen, lymph node or peripheral blood of the immunized animal. The immunization is carried out by administering the antigen together with an appropriate adjuvant (for example, complete Freund's adjuvant or a combination of aluminum hydroxide gel with pertussis vaccine) to the animal subcutaneously, intravenously or intraperitoneally. Following the first administration, the antigen is administered repeatedly 5 to 10 times at intervals of 1 to 2 weeks. Three to 7 days after each administration, a blood sample is collected from the venous plexus f the fundus of the eye, and the serum derived from the sample blood is tested, for example, by enzyme immunoassay [Enzyme-linked Immunosorbent Assay (ELISA), published by Igaku Shoin, 1976] to determine whether it binds to the antigen. A mouse or rat whose serum shows a sufficient antibody titer against the peptide used for immunization is submitted for use as a source of antibody-producing cells. For submission to fusion between splenocytes and myeloma cells, the spleen of the immunized mouse or rat is excised 3 to 7 days after the final administration of the antigenic substance and splenocytes of the spleen are collected. The spleen is cut to pieces in a serum-free basal medium (hereinafter referred to as "washing medium") and centrifuged, and the recovered cells are treated with Tris-ammonium chloride buffer (pH 7.65) for 1 to 2 minutes to eliminate erythrocytes. The remaining cells are then washed with the washing medium and used as splenocytes for cell fusion.

(3) Preparation of MYELOMA CELLS

Mouse-derived established cell lines are used as the myeloma cells. Thus, for instance, the 8-azaguanine-resistant mouse (BALB/c-derived) myeloma cell lines P3-X63Agg-U1 (P3-U1) [Current Topics in Microbiology and Immunology-1; *European Journal of Immunology*, 6, 511–519 (1976)], SP2/O-Ag14 (SP-2) [*Nature*, 276, 269–270 (1978)], P3-X63-Ag8653 (653) [*Journal of Immunology*, 123, 1548–1550 (1979)] and P3-X63-Ag8 (X63) [*Nature*, 256, 495–497 (1975)] may be used. These cell lines are subcultured in an 8-azaguanine medium [prepared by supplementing RPNE-1640 medium with glutamine (1.5 mM), 2-mercaptoethanol ($5\times10^{-5}$ M), gentamicin (10 µg/ml) and fetal calf serum (FCS) (10%) and further supplementing the resulting medium (hereinafter referred to as "normal medium") with 8-azaguanine (15 µg/ml)]. Three to four days before cell fusion, subculture is performed in the normal medium to thereby ensure a cell number of not less than $2\times10^7$ cells on the day of cell fusion.

(4) Cell Fusion

The antibody-producing cells obtained as described in (2) and the myeloma cells obtained as described in (3) are respectively washed thoroughly with the washing medium or PBS (1.83 g of disodium phosphate, 0.21 g of monopotassium phosphate and 7.65 g of sodium chloride per liter of distilled water, pH 7.2), and mixed in a proportion of 5 to 10 antibody-producing cells per myeloma cell. After recovering of the cells by centrifugation, the cells are thoroughly loosened, a mixture of 2 g of polyethylene glycol-1,000 (PEG-1,000), 2 ml of the washing medium and 0.7 ml of dimethyl sulfoxide is added to the cells with stirring in an amount of 0.2 to 1 ml/$10^8$ antibody-producing cells at 37° C., then several 1 to 2 ml portions of the washing medium are added at 1- to 2-minute intervals, and the whole amount is made 50 ml by further washing. After centrifugation, the recovered cells are loosened gently and then suspended in 100 ml of HAT medium [prepared by supplementing the normal medium with hypoxanthine ($10^{-4}$ M), thymidine ($1.5\times10^{-5}$ M) and aminopterin ($4\times10^{-7}$ M)]. This suspension is distributed in 100 µl portions into each well of 96-well culture plates, and incubation is carried out in a 5% $CO_2$ incubator at 37° C. for 7 to 14 days. After incubation, a portion of the culture supernatant is taken from each well and subjected, for example, to enzyme immunoassay which will be described later in (5) or to FACS (fluorescence-activated cell sorter), thereby selecting an antibody which specifically binds to the FGF-8 partial peptide. Thereafter, cloning is repeated twice by the limiting dilution method [using HT medium (HAT medium minus aminopterin) for the first cloning and the normal medium for the second] Cell lines for which a high antibody titer is constantly observed are selected as anti-FGF-8 monoclonal antibody-producing hybridoma cell lines.

(5) Selection of Anti-FGF-8 Monoclonal Antibody

Examples of the enzyme immunoassay for measuring antibodies include the sandwich method, an immunoenzymatic technique, a solid phase method in which an enzyme-labeled second antibody is used, a method in which an immobilized second antibody is used and a solid phase method in which an enzyme/anti-enzyme antibody system is used [*Protein, Nucleic Acid and Enzyme*, Supplement No.31, p.23 (1987)]. The following describes the method in which an enzyme-labeled second antibody is used.

Using a cross-linking agent, the antigenic peptide is linked in advance to a carrier protein which is different from the one used in the immunization A human FGF-8 partial peptide and a peptide having an amino acid sequence which is different from that of the partial peptide are linked to a carrier protein and used as control peptides. The peptide in a concentration of 1 to 50 µg/ml is distributed in 10 to 100 µl portions into each well of 96-well EIA plates and allowed to stand overnight at 4° C. to effect precoating. After blocking is effected with BSA solution or the like, a hybridoma culture supernatant or a purified antibody prepared in accordance with the following procedure (6) is used as a first antibody and distributed in 50 to 100 µl portions into each well of the EIA plates, and the reaction is carried out for 2 hours at room temperature or overnight at 4° C. After washing with PBS or a solution prepared by supplementing PBS with 0.05% Tween-20 (hereinafter referred to as "Tween-PBS"), 1 to 50 µg/ml solution of an anti-mouse or anti-rat immunoglobulin antibody labeled with biotin, an enzyme, a chemiluminescent substance, a radioactive compound or the like is used as a second antibody and distributed in 50 to 100 µl portions into each well of the EIA plate, and the reaction is carried out at room temperature for 1 to 2 hours. After thorough washing, each reaction corresponding to respective labeling substance of the second antibody is carried out, and a well which shows a specific bind to the human FGF-8 partial peptide is selected as a source of anti-FGF-8 monoclonal antibody.

(6) Preparation of Monoclonal Antibody

The hybridoma cells obtained in (4) capable of producing anti-FGF-8 monoclonal antibody are injected intraperitoneally into 8 to 10-week-old mice or nude mice treated with pristane [by intraperitoneal administration of 0.5 ml of 2,6,10,14-tetramethylpentadecane (pristane) followed by 3 to 10 days of rearing] at a dose of $2 \times 10^7$ to $5 \times 10^6$ cells per animal. The hybridoma causes an ascites tumor in 10 to 21 days. The ascitic fluid is collected from the mice, centrifuged (3,000 rpm, 5 minutes) to remove solid matter and, after salting out with 40 to 500% saturation ammonium sulfate, subjected to a caprylic acid precipitation method or passed through a DEAE-Sepharose column, a protein A column or a gel filtration column. Collected fractions of IgG or IgM are pooled to give a purified monoclonal antibody. The subclass of the antibody can be determined using a mouse monoclonal antibody typing kit or a rat monoclonal antibody typing kit. The amount of protein can be determined by the Lowry method or calculated based on the optical density at 280 nm.

(7) Confirmation of the Specificity of the Monoclonal Antibody (Western Blotting)

Bindability of the anti-FGF-8 monoclonal antibody selected in (5) with the FGF-8 protein is examined by Western blotting. A culture broth of a mouse breast cancer cell line SC-3 at the time of testosterone stimulation or FGF-8 protein in the culture broth or FGF-8 protein expressed in CHO cells is purified, fractionated by SDS-PAGE and then blotted on a nitrocellulose membrane or PVDF membrane. After blocking with BSA solution, reaction with a culture supernatant containing the anti-FGF-8 monoclonal antibody or 1 to 10 µg/ml of purified antibody is carried out at room temperature for 2 hours or overnight at 4° C. After washing with PBS or PBS-Tween, a 1 to 50 µg/ml solution of an anti-mouse or anti-rat immunoglobulin antibody labeled with biotin, an enzyme, a chemiluminescent substance, a radioactive compound or the like is used as a second antibody, and the reaction is carried out at room temperature for 1 to 2 hours. After thorough washing, each reaction corresponding to the respective labeling substance of the second antibody is carried out to confirm that the anti-FGF-8 monoclonal antibody can bind to the band which coincides with the molecular weight of the FGF-8 protein.

(8) Inhibition of FGF-8 Activity by the Monoclonal Antibody

The ability of the anti-FGF-8 monoclonal antibody selected in (5) to inhibit FGF activity is examined by a growth inhibition assay using a mouse breast cancer cell line SC-3 or a cell line derived from human prostatic cancer or breast cancer as the target cells. According to this method, the target cells are cultured in a medium containing FGF-8 (1 to 100 ng/ml) or testosterone, which is supplemented in advance with a culture supernatant containing the anti-FGF-8 monoclonal antibody or purified antibody serially diluted to a final concentration of 0.1 to 100 µg/ml. After 24 to 72 hours of culturing, the number of viable cells is measured using an MTT [3-(4,5-dimethyl-2-thiazonyl)-2,5-diphenyl-2H-tetrazolium bromide] solution or a cell counting kit, thereby confirming inhibition of FGF-8 activity by the anti-FGF-8 monoclonal antibody.

2. Production of Human Chimeric Antibody and Human CDR-grafted Antibody (1) Construction of Vector for Humanized Antibody Expression A vector for expression of humanized antibody is an expression vector for animal cell into which DNAs encoding CH and CL of a human antibody have been inserted, and is constructed by cloning each of DNAs encoding CH and CH of a human antibody into an expression vector for animal cell.

The C region of a human antibody may be CH and CL of any human antibody. Examples include CH belonging to γ1 subclass and CL belonging to κ class of a human antibody, and the like. As the DNAs encoding CH and CL of a human antibody, a chromosomal DNA comprising an exon and an intron or cDNA can be used. As the expression vector for animal cell, any expression vector can be used, so long as a C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981)], pSGIβd2–4 [*Cytotechnology*, 4, 173 (1990)], pSE1 UK-Sed1–3 [*Cytotechnol.*, 13, 79 (1993)] and the like. Examples of a promoter and enhancer used for an expression vector for animal cell include an SV40 early promoter and enhancer [*J. Biochem.*, 101, 1307 (1987)], a Moloney mouse leukemia virus LTR promoter and enhancer [*Biochem. Biophys. Res. Commun.*, 149, 960 (1987)], an immunoglobulin H chain promoter [*Cell*, 41, 479 (1985)] and enhancer [*Cell*, 33, 717 (1983)], and the like.

The vector for expression of humanized antibody may be either of a type in which the H chain and the L chain of the antibody exist on separate vectors or of a type in which both chains exist on the same vector (tandem type). In respect of easiness of construction of a vector for expression of humanized antibody expression, easiness of introduction into animal cells, and balance between the expression amounts of the H chain and the L chain of the antibody in animal cells, a tandem type of the vector for expression of humanized antibody is preferred [*J. Immunol. Methods*, 167, 271 (1994)]. Examples of the tandem type of the vector for humanized antibody expression include pKANTEX93 (WO97/10354), pEE18 [HYBRIDOMA, 17, 559 (1998)], and the like.

The constructed vector for expression of humanized antibody can be used for expression of a human chimeric antibody and a human CDR-grafted antibody in animal cells.

(2) Preparation of cDNA Encoding V Region of Antibody Derived from Non-Human Animal and Analysis of Amino Acid Sequence cDNAs encoding VH and VL of a non-human animal antibody such as a mouse antibody are obtained as follows.

mRNA is extracted from hybridoma cells producing a mouse antibody or the like, which synthesizes cDNA. The synthesized cDNA is inserted into a vector such as a phage or a plasmid to prepare a cDNA library. Each of a recombinant phage or recombinant plasmid containing cDNA encoding VH and a recombinant phage or recombinant plasmid containing cDNA encoding VL is isolated from the library using a part of the C region or V region of a mouse antibody as the probe. The full nucleotide sequences of VH and VL of the mouse antibody of interest on the recombinant phage or recombinant plasmid are determined, and the full amino acid sequences of VH and VL are deduced from the nucleotide sequences.

The non-human animal may be any animal such as mouse, rat, hamster or rabbit, so long as a hybridoma can be produced therefrom.

The method for preparing a total RNA from a hybridoma include a guanidine thiocyanate-cesium trifluoroacetate method [*Methods in Enymol.*, 154, 3 (1987)] and the like. The method for preparing mRNA from total RNA include an oligo (dT) immobilized cellulose column method [*Molecular Cloning: A Laboratory Manual*, Cold Spring Harbor Lab. Press, New York (1989)] and the like. Also, a kit for preparing mRNA from a hybridoma cell includes Fast Track mRNA Isolation Kit (manufactured by Invitrogen), Quick Prep mRNA Purification Kit (manufactured by Pharmacia) and the like.

The method for synthesizing cDNA and preparing a cDNA library include conventional methods [*Molecular Cloning: A Laboratory Manual*, Cold Spring Harbor Lab. Press, New York (1989), *Current Protocols in Molecular Biology*, Supplement 1–34]; a method using a commercially available kit such as Super Script™ Plasmid System for cDNA Synthesis and Plasmid Cloning (manufactured by GIBCO BRL), ZAP-cDNA Kit (manufactured by Stratagene); and the like.

Any vector into which the cDNA synthesized using mRNA extracted from a hybridoma as the template may be inserted for preparing a cDNA library, so long as the cDNA can be inserted. Examples include ZAP Express [*Strategies*, 5, 58 (1992)], pBluescript II SK((+)) [*Nucleic Acids Research*, 17, 9494 (1989)], kzapli (manufactured by Stratagene), λgt10 and λgt11 [*DNA Cloning: A Practical Approach*, 1, 49 (1985)], Lambda BlueMid (manufactured by Clontech), λExCell and pT7T318U (manufactured by Pharmacia), pcD2 [*Mol. Cell. Biol.*, 3, 280 (1983)], pUC18 [*Gene*, 33, 103 (1985)] and the like.

Any *E. coli* for introducing the cDNA library constructed by a phage or plasmid vector may be used, so long as the cDNA library can be introduced, expressed and maintained. Examples include XL1-Blue MRF' [*Strategies*, 581 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol Biol*, 16, 118 (1966)], JM105 [*Gene*, 38, 275 (1985) ] and the like.

A colony hybridization or plaque hybridization method using an isotope- or fluorescence-labeled probe may be used for selecting cDNA clones encoding VH and VL of an antibody derived from a non-human animal in the cDNA library [*Molecular Cloning: A Laboratory Manual*, Cold Spring Harbor Lab. Press, New York (1989)]. Also, the cDNAs encoding VH and VL can be prepared through polymerase chain reaction [PCR, *Molecular Cloning: A Laboratory Manual*, Cold Spring Harbor Lab. Press, New York (1989); *Current Protocols in Molecular Biology*, Supplement 1–34] by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−) (manufactured by Stratagene), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as ABI377 (manufactured by Applied biosystems) or the like.

Whether the obtained cDNAs encode the fill amino acid sequences of VH and VL of the antibody containing a secretory signal sequence can be confirmed by estimating the full amino acid sequences of VH and VL from the determined nucleotide sequence and comparing them with full amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full amino acid sequences of VH and VL of the antibody comprising a secretory signal sequence with full amino acid sequences of VH and VL of known antibodies [*Sequences of Proteins of Immunological Interest*, US Dept. Health and Human Services (1991)], and the subgroup to which they belong can be known. Furthermore, the amino acid sequence of each of CDRs of VH and VL can be identified.

Moreover, the novelty of the sequence can be examined by carrying out a homology search with sequences in any database, for example, SWISS-PROT, PIR-Protein or the like using the full amino acid sequences of VH and VL, for example, according to the BLAST method [*J. Mol. Biol*, 215, 403 (1990)] or the like.

(3) Construction of Human Chimeric Antibody Expression Vector

A human chimeric antibody expression vector can be constructed by cloning cDNAs encoding VH and VL of an antibody derived from a non-human animal in upstream of DNAs encoding CH and CL of a human antibody on the vector for expression of humanized antibody as described in the item 2(1). For example, by using a plasmid comprising cDNAs encoding VH and VL of an antibody derived from a non-human animal as the template, VH and VL of the antibody are amplified by PCR using primers at the 5'-terminal side and the 3'-terminal side comprising a recognition sequence of an appropriate restriction enzyme and a nucleotide sequence encoding the V region, the respective amplified product is cloned into a plasmid such as pBluescript SK(−) (manufactured by Stratagene), the nucleotide sequence is determined according to the method described in the item 2(2), and thus a plasmid comprising the DNA sequences encoding the amino acid sequences of VH and VL of the desired antibody is obtained cDNAs encoding the amino acid sequences of VH and VL of the antibody are isolated from the plasmid and are cloned so as to express them in an appropriate form in upstream of the genes encoding the C regions of the H chain and L chain of the human antibody in the vector for expression of humanized antibody described in the item 2(1) to thereby construct a vector for a humanized chimeric antibody expression.

(4) Construction of cDNA Encoding V Region of Human CDR-grafted Antibody cDNAs encoding VH and VL of a human CDR-grafted antibody can be obtained as follows. First, amino acid sequences of FRs in VH and VL of a human antibody to which amino acid sequences of CDRs in VH and VL of an antibody derived from a non-human animal antibody are grafted are selected. Any amino acid sequences of FRs in VH and VL of a human antibody can be used, so long as they are derived from a human antibody. Examples include amino acid sequences of FRs in VH and VL of human antibodies registered in database such as Protein Data Bank, and amino acid sequences common to subgroups of FRs in VH and VL of human antibodies [*Sequences of Proteins of Immunological Interest*, US Dept. Health and Human Services (1991)], and the like. Among these, in order to produce a human CDR-grafted antibody having potent activity, amino acid sequences having high homology (at least 60% or more) with amino acid sequence of FRs in VH and VL of a target antibody derived from a non-human animal is preferably selected.

Then, amino acid sequences of CDRs in VH and VL of the antibody derived from a non-human animal are grafted to the selected amino acid sequences of FRs in VH and VL of a human antibody to design amino acid sequences of VH and VL of a human CDR-grafted antibody. The designed amino acid sequences are converted to nucleotide sequences by considering the frequency of codon usage found in nucleotide sequences of genes encoding antibodies [*Sequence of Proteins of Immunological Interest*, US Dept. Health and Human Services (1991)], and the DNA sequences encoding the amino acid sequences of VH and VL of a human CDR-grafted antibody are designed. Several synthetic DNAs having a length of about 100 nucleotides are synthesized based on the designed nucleotide sequences, and PCR is carried out by using them. In this case, it is preferred in each of VH and VL that 6 synthetic DNAs are designed in view of the reaction efficiency of PCR and the lengths of DNAs which can be synthesized. Furthermore, they can be easily cloned into the vector for humanized antibody expression constructed in the item 2(1) by introducing the recognition sequence of an appropriate restriction enzyme to the 5' end of the synthetic DNAs present at both ends. After the PCR, an amplified product is cloned into a plasmid such as pbluescript SK(-) (manufactured by Stratagene), and the nucleotide sequences are determined according to the method described in the item 2(2) to obtain a plasmid having nucleotide sequences encoding VH and VL of a designed human CDR-grafted antibody.

(5) Modification of Amino Acid Sequence of V Region of Human CDR-grafted Antibody It is known that when a human CDR-grafted antibody is produced by simply grafting only CDRs in VH and VL of an antibody derived from a non-human animal in FRs in VH and VL of a human antibody, its antigen-binding activity is lower than that of the original antibody derived from a non-human animal [*BIO/TECHNOLOGY*, 9, 266 (1991)]. As the reason, it is considered that several amino acid residues in not only CDRs but also FRs directly or indirectly relate to antigen-binding activity in VH and VL of the original antibody derived from a non-human animal, and that they are changed to different amino acid residues of different FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased [*BIO/TECHNOLOGY*, 9, 266 (1991)]. In the production of a human CDR-grafted antibody, how to efficiently identify the amino acid residues relating to the antigen binding activity in FR is most important, so that the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. Although the information of the three-dimensional structure of antibodies has been useful in the production of a human CDR-grafted antibody, a method for producing a human CDR-grafted antibody which is applicable to all antibodies has not been established yet. Therefore, various attempts must currently be necessary, for example, several modified antibodies of each antibody are produced to examine the relationship between each of the modified antibodies and its antibody binding activity.

The modification of the selected amino acid sequence of FR in VH and VL of a human antibody can be accomplished by PCR using various synthetic DNA for modification. With regard to the amplified product obtained by the PCR, the nucleotide sequence is determined according to the method as described in the above 1(2) to conform whether the objective modification has been carried out is confirmed.

(6) Construction of Vector for Human CDR-grafted Antibody Expression

A vector for human CDR-grafted antibody expression can be constructed by cloning cDNAs encoding VH and VL of the human CDR-grafted antibody constructed in the item 2(4) and 1(5) into upstream of DNAs encoding CH and CL of the human antibody in the vector for expression of humanized antibody as described in the item 2(1). For example, when recognition sites for an appropriate restriction enzymes are introduced to the 5'-terminal of synthetic DNAs positioned at both ends among synthetic DNAs used in the construction of VH and VL of the human CDR-grafted antibody in the item 2(4) and 1(5), cloning can be carried out so that they are expressed in an appropriate form in upstream of DNAs encoding CH and CL of the human antibody in the vector for expression of humanized antibody as described in the item 2(1).

(7) Transient Expression of Humanized Antibodies

In order to efficiently evaluate the antigen binding activity of various humanized antibodies produced, the humanized antibodies can be expressed transiently using the humanized antibody expression vector as described in the item 2(3) and 1(6) or the modified expression vector thereof. Any cell can be used as a host cell, so long as the host cell can express a humanized antibody. Generally, COS-7 cell (ATCC CRL1651) is used in view of its high expression amount [*Methods in Nucleic Acids Res.*, CRC Press, p.283 (1991)]. The method for introducing the expression vector into COS-7 cell include a DEAE-dextran method [*Methods in Nucleic Acids Res.*, CRC Press, p. 283 (1991)], a lipofection method [*Proc. Natl. Acad. Sci. USA*, 84, 7413 (1987)] and the like.

After the vector is introduced into the cell, the expression amount and antigen binding activity of the humanized antibody in the culture supernatant can be determined by the enzyme immunoassay [ELISA; *Antibodies: A Laboratory Manual*, Cold Spring Harbor Laboratory, Chapter 14 (1988), *Monoclonal Antibodies: Principles and Practice*, Academic Press Limited (1996)] and the like.

(8) Stable Expression of Humanized Antibody

A transformant which produces a humanized antibody stably can be obtained by introducing into an appropriate host cell the humanized antibody expression vector described in the items 2(3) and 1(6).

The method for introducing the expression vector into a host cell include electroporation [Japanese Published Unexamined Patent Application No. 257891/90, *Cytotechnology,* 3, 133 (1990)] and the like.

Any cell can be used as the host cell into which the vector for humanized antibody expression is to be introduced, so long as it can express a humanized antibody. Examples include mouse SP2/0-Ag14 cell (ATCC CRL1581), mouse P3×63-Ag8.653 cell (ATCC CRL1580), CHO cell in which a dihydrofolate reductase gene (dhfr) is detective [*Proc. Natl. Acad. Sci. U.S.A.,* 77, 4216 (1980)], rat YB2/3HL.P2.G11.16Ag.20 cell (YB2/0 cell, ATCC CRL1662) and the like.

After the expression vector is introduced into the cell, transformants which express a humanized antibody stably are selected by culturing in a medium for animal cell culture comprising an agent such as G418 sulfate (G418, manufactured by Sigma) or the like [*J. Immunol. Methods,* 167, 271 (1994)]. The medium for animal cell culture includes PRMI1640 medium (manufactured by Nissul Pharmaceutical), GIT medium (manufactured by Nissul Pharmaceutical), EX-CELL302 medium (manufactured by JRH), IMDM medium (manufactured by GIBCO BRL), Hybridoma-SFM medium (manufactured by GDCO BRL), media obtained by adding various additives such as FBS to these media, and the like. The humanized antibody can be produced and accumulated in a culture medium by culturing the selected transformants in a medium. The amount and the antigen binding activity of the humanized antibody expressed in the culture medium can be measured by ELISA or the like. Also, the production amount of the humanized antibody can be increased by transformation using dhfr amplification system or the like [*J. Immunol. Methods,* 167, 271 (1994)].

The humanized antibody can be purified from the medium culturing the transformant by using a protein A column [*Antibodies, A Laboratory Manual,* Cold Spring Harbor Laboratory, Chapter 8 (1988), *Monoclonal Antibodies: Principles and Practice,* Academic Press Limited (1996)]. Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis [SDS-PAGE; *Nature,* 227, 680 (1970)], Western blotting [*Antibodies, A Laboratory Manual,* Cold Spring Harbor Laboratory, Chapter 12 (1988), *Monoclonal Antibodies: Principles and Practice,* Academic Press Limited (1996)], and the like.

3. Preparation of Antibody Fragment

The antibody fragment can be prepared based on the humanized antibody described in the item 2 genetically or proteinochemically. The antibody fragment includes Fab, F(ab)$_2$, Fab', scFv, Diabody, dsFv, a peptide comprising CDR and the like.

(1) Preparation of Fab

Fab can be prepared by treating IgG with a proteolytic enzyme papain. After the papain treatment, when the original antibody is an IgG subclass having a protein A binding activity, uniform Fab can be collected by passing through a protein A column in order to separate IgG molecules and Fc fragments [*Monoclonal Antibodies: Principles and Practice,* third edition (1995)]. When the original antibody is an antibody of IgG subclass having no protein A binding activity, Fab can be collected by ion exchange chromatography in a fraction eluted at a low salt concentration [*Monoclonal Antibodies: Principles and Practice,* third edition (1995)]. Furthermore, Fab can also be prepared genetically by using *Escherichia coli.* For example, an Fab expression vector can be prepared by cloning the DNA encoding the antibody V region described in the items 2(2), (3) and (5) into a vector for expression of Fab. As the vector for expression of Fab, any vector can be used, so long as a DNA encoding Fab can be inserted and expressed. Examples include pIT106 [*Science,* 240, 1041 (1988)] and the like. Fab can be formed and accumulated in an inclusion body or periplasmic space by introducing the Fab expression vector into an appropriate *Escherichia coli.* Fab having a binding activity can be obtained from the inclusion body by a refolding method generally used for producing a protein, and when it is expressed in the periplasmic space, the Fab having a binding activity is leaked in the culture supernatant. Uniform Fab can be purified after the refolding or from the culture medium using an antigen-linked column [*Antibody Engineering, A Practical Guide,* W.H. Freeman and Company (1992)].

(2) Preparation of F(ab')$_2$

F(ab')$_2$ can be prepared by treating IgG with a protease pepsin. After the pepsin treatment, uniform F(ab')$_2$ can be recovered by a purification procedure similar to the case of Fab [*Monoclonal Antibodies: Principles and Practice,* third edition, Academic Press (1995)]. Furthermore, it can also be prepared by the method described in the item 3(3) in which Fab' is treated with maleimide such as o-PDM or bismaleimide hexane to form a thioether bond, or a method in which it is treated with DTNB to form an S—S bond [*Antibody Engineering, A Practical Approach,* IRL PRESS (1996)].

(3) Preparation of Fab'

Fab' can be prepared by treating F(ab')$_2$ described in the item 3(2) with a reducing agent such as dithiothreitol. Furthermore, Fab' can be prepared genetically by using *Escherichia coli.* For example, an Fab' expression vector can be constructed by cloning the DNA encoding the antibody V region described in the items 2(2), (4) and (5) into a vector for expression of Fab'. As the vector for expression of Fab', any vector can be used, so long as a DNA encoding Fab' can be inserted and expressed. Examples include pAK19 [*Bio/Technology,* 10, 163 (1992)] and the like. Fab' can be formed and accumulated in an inclusion body or periplasmic space by introducing the Fab' expression vector into an appropriate *Escherichia coli.* Fab' having a binding activity can be obtained from the inclusion body by a refolding method generally used for producing a protein, and when it is expressed in the periplasmic space, it can be collected extracellularly by disrupting the cells with a treatment such as lysozyme partial digestion, osmotic pressure shock or sonication. Uniform Fab' can be purified after the refolding or from the disrupted cell suspension using a protein G column or the like [*Antibody Engineering, A Practical Approach,* IRL PRESS (1996)].

(4) Preparation of scFv scFv can be prepared genetically using a phage or *Escherichia coli.* For example, a DNA encoding scFv is produced by ligating DNAs encoding the antibody VH and VL described in the items 2(2), (4) and (5) via a DNA encoding a polypeptide linker comprising an amino acid sequence of 12 residues or more. An scFv expression vector can be constructed by cloning the DNA into a vector for expression of scFv. As the vector for expression of scFv, any vector can be used, so long as DNA encoding scFv can be inserted and expressed. Examples include pCANTAB5E (manufactured by Pharmacia), Phfa [*Hum. Antibody Hybridoma*, 5, 48 (1994)] and the like. The scFv expression vector was introduced into an appropriate *Escherichia coli* and infected with a helper phage to thereby obtain a phage which expresses scFv fused with the phage surface protein on the phage surface. Also, scFv can be formed and accumulated in the inclusion body or periplasmic space of *Escherichia coli* into which scFv expression vector is introduced. scFv having a binding activity can be obtained from the inclusion body by a refolding method generally used for producing a protein, and when it is expressed in the periplasmic space, it can be collected extracellularly by disrupting the cells with a treatment such as lysozyme partial digestion, osmotic pressure shock, sonication or the like. Uniform scFv can be purified after the refolding or from the disrupted cell suspension by cation exchange chromatography or the like [*Antibody Engineering, A Practical Approach*, IRL PRESS (1996)].

(5) Preparation of Diabody

Diabody can be prepared by changing the polypeptide linker used to prepare the above scFv to about 3 to 10 residues. A divalent diabody can be prepared when VH and VL of one antibody species is used. A diabody having two different specificity can be prepared when VH and VL of two antibody species are used [*FEBS Letters*, 453, 164 (1999), *Int. J. Cancer*, 77, 763 (1998)].

(6) Preparation of dsFv dsfv can be prepared genetically by using *Escherichia coli* First, DNAs in which an encoded amino acid residue is replaced with a cysteine residue are produced by introducing mutation into appropriate positions of the DNAs encoding the antibody VH and VL described in the items 2(2), (4) and (5). Expression vectors for VH and VL can be produced by cloning each of the DNAs into a vector for expression of dsFv. As the vector for expression of dsFv, any vector can be used, so long as DNA encoding dsFv can be inserted and expressed. Examples include pUL19 [*Protein Engineering*, 7, 697 (1994)] and the like. The expression vectors for VH and VL are introduced into an appropriate *Escherichia coli* to thereby form and accumulate the VH and VL in the inclusion body or periplasmic space. The VH and VL are obtained from the inclusion body or periplasmic space and mixed, and dsFv having a binding activity can be obtained by a refolding method generally used for producing a protein. After the refolding, it can be further purified by ion exchange chromatography, gel filtration or the like [*Protein Engineering*, 7, 697 (1994)].

(7) Preparation of Peptide Comprising CDR

A peptide comprising CDR can be prepared by a chemical synthesis method such as Fmoc or tboc. Also, a DNA encoding a peptide comprising CDR is prepared, and the resulting DNA is cloned into an appropriate vector for expression to thereby prepare the peptide comprising CDR. As the vector for expression, any vector can be used, so long as a DNA encoding a peptide comprising CDR is inserted and expressed. Examples include pLEX (manufactured by Invitrogen), pAX4a(+) (manufactured by Invitrogen) and the like. The expression vector is introduced into an appropriate *Escherichia coli* so that the peptide comprising CDR can be formed and accumulated in the inclusion body or periplasmic space. The peptide comprising CDR can be obtained from the inclusion body or periplasmic space, and it can be purified by ion exchange chromatography, gel filtration or the like [*Protein Engineering*, 7, 697 (1994)].

4. Activity Evaluation of Humanized Antibody or Antibody Fragment (1) Antigen Binding Activity The FGF-8 binding activity of the prepared humanized antibody or antibody fragment can be measured by ELISA or surface plasmon resonance [*J. Immunol. Methods*, 145, 229 (1991)] or the like.

(2) Inhibition Activity for Function Having FGF-8

The inhibition activity for function having FGF-8 of the prepared humanized antibody or the antibody fragment can be measured, e.g., by a cell growth test using a cell line. For example, the inhibition activity for function having FGF-8 of the prepared humanized antibody or antibody fragment can be measured by culturing the mouse breast cancer cell line SC-3 [*Proc. Natl. Acad. Sci. U.S.A.*, 89, 8928 (1992)], the mouse fibroblast cell line NIH3T3 or a human prostate cancer, breast cancer or ovarian cancer cell line as the target cells, using a medium containing 1 to 100 ng/ml of FGF-8 or testosterone, for a period of 24 to 72 hours after adding the humanized antibody or the antibody fragment serially diluted to a final concentration of 0.001 to 100 µg/ml to the medium, and then measuring the number of viable cells using an MTT [3-(4,5-dimethyl-2-thiazonyl)-2,5-diphenyl-2H-tetrazolium bromide] solution, a cell counting kit, a WST-1 kit or the like. Also, the activity of the humanized antibody or the antibody fragment to inhibit binding of FGF-8 to the cell surface receptor can be measured by Bolton-Hunter method in which FGF-8 labeled with $^{125}$I is used [*Biochem. J.*, 133, 527 (1973)] or the like to the above cell lines.

(3) In Vivo Antitumor Effect

In vivo antitumor effect of the prepared humanized antibody or the antibody fragment can be evaluated, for example, by using the nude mouse cancer cell transplantation system shown below.

a. Evaluation of Antitumor Effect for Early Cancer Model

The mouse breast cancer cell line SC-3 is suspended in PBS to give a density of $1 \times 10^7$ cells/ml and subcutaneously transplanted into 6- to 8-week-old male nude mice at a dose of 0.1 ml/animal ($1 \times 10^6$ cells/animal). Just after the transplantation, the humanized antibody or the antibody fragment is administered into the mouse abdominal cavity or caudal vein at a dose of 10 µg to 400 µg/animal. The antibody is administered at a frequency of 1 to 7 times a week in a total of 1 to 10 times. The antitumor effect can be evaluated by periodically measuring tumor volumes for 14 to 60 days after the tumor transplantation, and comparing the tumor volumes with those of the negative control antibody administered group or the solvent administered group. Also, the tumor volume (V) is calculated based on the following equation by measuring its length (L), width (W) and height (H) using slide calipers.

$$V(mm^3) = (L) \times (W) \times (H) \times 0.5236$$

b. Evaluation of Antitumor Effect for Advanced Cancer Model

SC-3 is suspended in PBS to give a density of $1 \times 10^7$ cells/ml and subcutaneously transplanted into 6- to 8-week-old male nude mice at a dose of 0.1 ml/animal ($1 \times 10^6$ cells/animal). When the tumor volume becomes approximately from 100 to 300 mm$^3$ (around the 14th day after tumor transplantation), administration of the humanized antibody or antibody fragment into the mouse abdominal cavity or caudal vein is started at a dose of from 10 µg to 400

μg/animal. The antibody is administered at a frequency of 1 to 7 times a week in a total of 1 to 10 times. The antitumor effect can be evaluated in the same manner as in the early cancer model of a.

5. Method for Using Humanized Antibody or Antibody Fragment Thereof.

Since the humanized antibody or the antibody fragment thereof of the present invention specifically binds to FGF-8 which is considered to be a growth factor of human cancer cells which show sex hormone-dependent growth and inhibits the function of FGF-8, it will be useful in treating and diagnosing human cancers such as prostate cancer, breast cancer, ovarian cancer and testis tumor. Also, since the proportion of amino acid sequences derived from human antibodies of the humanized antibody or the antibody fragment thereof is higher than that in antibodies derived from a non-human animal, it is expected that the humanized antibody or the antibody fragment thereof shows strong cytotoxic activity in the human body, it does not show immunogenicity, and its effects continue for a long time.

The humanized antibody or the antibody fragment thereof of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in an antibody or peptide formulation.

The dosage form includes sprays, capsules, tablets, granules, syrups, emulsions, suppositories, injections, ointments, tapes, and the like.

Formulations suitable for oral administration include emulsions, syrups, capsules, tablets, powders, granules, and the like.

Liquid preparations such as emulsions and syrups, can be produced by using additives, for example, water, saccharides such as sucrose, sorbitol, fructose; glycols such as polyethylene glycol, propylene glycol; oils such as sesame oil, olive oil, soybean oil; antiseptics such as p-hydroxybenzoate; and flavors such as strawberry flavor, peppermint.

Capsules, tablets, powders, granules and the like can be produced by using additives, for example, fillers such as lactose, glucose, sucrose, mannitol, disintegrating agents such as starch, sodium alginate; lubricants such as magnesium stearate; talc; binders such as polyvinyl alcohol, hydroxypropylcellulose, gelatin; surfactants such as fatty acid esters; and plasticizers such as glycerine.

Formulations suitable for parenteral administration include injections, suppositories, sprays and the like.

Injections can be prepared by using a carrier such as a salt solution, a glucose solution or a mixture thereof.

Suppositories can be prepared by using a carrier such as cacao butter, hydrogenated fat or carboxylic acid.

Also, sprays can be prepared from the antibody itself or using a carrier or the like which does not stimulate oral and airway mucous membranes of patients and can facilitate absorption of the antibody or antibody fragment thereof by dispersing it as minute particles.

The carrier includes lactose, glycerine, and the like. Depending on the properties of the antibody or the antibody fragment and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 0.01 mg/kg to 20 mg/kg per day per adult.

The present invention will now be illustrated in greater detail by way of Examples, but it should be understood that the invention is not construed as being limited thereto.

EXAMPLE 1

(1) Preparation of Immunogen

A peptide was synthesized by designing an amino acid sequence (Sequence ID NO:1) in which cystein was added to the C-terminal of a partial amino acid sequence of human FGF-8, the 23 position residue to the 46 position residue counting from the N-28 terminal, in order to effect its binding with a carrier protein. The peptide synthesis was carried out using a multi-item simultaneous solid layer system automatic peptide synthesizer PSSM-8 (manufactured by Shimadzu Corp.). In order to improve antigenicity, a conjugate of the synthesized peptide with KLH (manufactured by Calbiochem Co.) was prepared and used as the immunogen. That is, KLH was dissolved in PBS to a concentration of 10 μg/ml, and ⅒ volume of 25 mg/ml MBS (Nakalai Tesque) was added dropwise to the KLH solution, followed by 30 minutes of reaction with stirring. Free MBS was removed by passing the reaction solution through a gel filtration column such as a Sephadex G-25 column (Pharmacia) or the like which has been equilibrated in advance with PBS, thereby obtaining 2.5 mg of a KLH-MBS conjugate. This was further mixed with 1 mg of the peptide dissolved in 0.1 M sodium phosphate buffer (pH 7.0), and the mixture was stirred at room temperature for 3 hours to effect the reaction. After the reaction, the reaction solution was dialyzed against PBS-0.5 M NaCl and used as the immunogen.

(2) Immunization of Animals and Preparation of Antibody-producing Cells

A 100 μg portion of the peptide-KLH conjugate prepared by the method described in Example 1(1) was administered together with 2 mg of aluminum gel and $1\times10^9$ cells of pertussis vaccine (manufactured by Chiba Serum Institute) to mice of 5 weeks of age (Balb/c). Starting 2 weeks after the administration, 100 μg of the peptide-KLH conjugate was administered once a week in total of 4 times. A blood sample was collected from the venous plexus of the fundus of the eye, antibody titer of the serum derived from the sample blood was examined by an enzyme immunoassay which will be described in Example 1(3), and the spleen was excised from a mouse showing sufficient antibody titer after 3 days of the final immunization. The spleen was cut to pieces in MEM medium (manufactured by Nissui Pharmaceutical), loosened using a pair of forceps and then subjected to 5 minutes of centrifugation at 1,200 rpm. Thereafter, the supernatant was discarded, the obtained precipitate was treated with Tris-ammonium chloride buffer (pH 7.65) for 1 to 2 minutes to remove erythrocytes, and then the remaining cells were washed three times with MEM medium and used for cell fusion.

(3) Enzyme Immunoassay

A conjugate obtained by cross-linking the human FGF-8 partial peptide shown in Sequence ID NO:1 with thyroglobulin in the following manner was used as the antigen for the assay. That is, 1 mg of the peptide was dissolved in 0.1 M ammonium acetate buffer and the solution was adjusted to 1 ml by adding 5 mg of THY which has been dissolved in advance in the same buffer. To this, while stirring, was added dropwise 540 µl of 0.02 M glutaraldehyde, followed by 5 hours of stirring at room temperature to effect the reaction. After the reaction, the reaction solution was dialyzed overnight against PBS and used as the antigen. A conjugate obtained in the same manner by cross-linking the peptide shown in Sequence ID NO:2 with THY was used as a reference antigen. A 10 µg/ml solution of the prepared conjugate was distributed in 50 µl portions in wells of a 96-well plate for EIA (manufactured by Greiner), and the plate was allowed to stand overnight at 4° C. to effect coating. After washing, 1% BSA-PBS was distributed in 100 µl portions into wells of the plate which was subsequently subjected to 1 hour of reaction at room temperature to block the remaining active groups. The 1% BSA-PBS was then discarded, and a hybridoma culture supernatant or an immunized mouse antiserum was distributed in 50 µl portions into wells of the plate, subsequently carrying out 2 hours of reaction. After washing with Tween-PBS, a peroxidase-labeled rabbit anti-mouse immunoglobulin (manufactured by DAKO) was distributed in 50 µl portions into wells of the plate to carry out 1 hour of reaction at room temperature, the plate was again washed with Tween-PBS, and then color development was effected using an ABTS substrate [2,2-azinobis(3-ethylbenzothiazole-6-sulfonic acid)ammonium] solution and absorbance at $OD_{415}$ was measured (NJ 2001, Japan Intermed).

(4) Preparation of Mouse Myeloma Cells

The 8-azaguanine-resistant mouse myeloma cell line P3-U1 was cultured in the normal medium and not less than $2 \times 10^7$ cells were thereby secured at the time of cell fusion and submitted for cell fusion as a parent line.

(5) Preparation of Hybridoma

The mouse splenocytes obtained in Example 1(2) and the myeloma cells obtained in Example 1(4) were mixed in a ratio of 10:1, and the mixture was centrifuged (1,200 rpm, 5 minutes). The supernatant was discarded, and the precipitated cells were thoroughly loosened. A solution composed of a mixture of 2 g of polyethylene glycol-1,000 (PEG-1,000), 2 ml of MEM medium and 0.7 ml of dimethyl sulfoxide was added to the cells with stirring at 37° C. in an amount of 0.2 to 1 ml per 108 mouse splenocytes, followed by the addition of several 1 to 2 ml portions of MEM medium at 1 to 2 minute intervals. Thereafter, the total volume was made 50 ml by addition of MEM medium. After centrifugation (900 rpm, 5 minutes), the supernatant was discarded, and the cells were gently loosened and then gently suspended in 100 ml of HAT medium by repeated drawing up into and discharging from a graduated pipette. The suspension was distributed in 100 µl portions into wells of a 96-well culture plate, and incubation was performed in a 5% $CO_2$ incubator at 37° C. for 10 to 14 days. Each culture supernatant was examined by the enzyme immunoassay described in Example 1(3) to select wells which showed specific reaction with the FGF-8 peptide. Using the selected wells, cloning was repeated twice using HT medium and the normal medium, respectively, thereby establishing hybridoma cell lines capable of producing the anti-FGF-8 monoclonal antibody. The monoclonal antibody KM1334 shown in FIG. 1 is an example of these hybridoma cell lines. Hybridoma KM1334 was deposited on Mar. 7, 1996, at the National Institute of Bioscience and Human-Technology, Agency of Industrial Science and Technology, (1–3, Higashi 1-chome, Tsukuba-shi, Ibaraki, Japan), and has been assigned the designation FERM BP-5451. In this connection, its antibody class was IgG1 determined by an enzyme immunoassay using a subclass typing kit.

(6) Purification of Monoclonal Antibody

The hybridoma cell line obtained in Example 1(3) was intraperitoneally administered to pristane-treated female nude mice (Balb/c) of 8 weeks of age at a dose of 5 to $20 \times 10^6$ cells per animal. The hybridoma caused ascites tumor in 10 to 21 days. The ascitic fluid was collected from each ascitic fluid-carrying mouse (1 to 8 ml per animal), centrifuged (3,000 rpm, 5 minutes) to remove solid matter and then purified by the caprylic acid precipitation method (Antibodies—A Laboratory Manual, Cold Spring Harbor Laboratory, 1988) to obtain purified monoclonal antibody.

EXAMPLE 2

Figure 2:
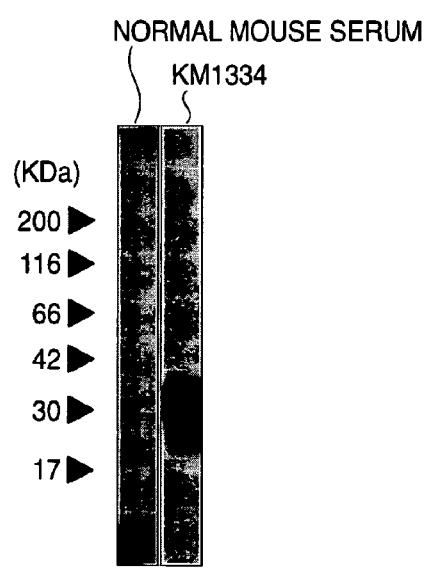
FIG. 2 shows the reactivity of anti-FGF-8 monoclonal antibody KM1334 with purified FGF-8 protein in Western blotting.

(1) Examination of the Specificity of the Monoclonal Antibody by Western Blotting The FGF-8 protein purified from a culture broth of the mouse breast cancer cell line SC-3 at the time of testosterone stimulation was fractionated by SDS-PAGE in an amount of 0.1 µg per lane and then blotted on a PVDF film in the usual way. After blocking with 1% BSA-PBS, reaction with the anti-FGF-8 monoclonal antibody KM1334 (10 µg/ml) or normal mouse serum used as a control antibody (×500) was carried out at room temperature for 2 hours or overnight at 4° C. After thorough washing with Tween-PBS, reaction with a peroxidase-labeled anti-mouse immunoglobulin antibody (manufactured by DAKO) was carried out at room temperature for 1 hour. After thorough washing with Tween-PBS, reaction with ECL (manufactured by Amersham) reagent was carried out for 1 minute, excess reagent was removed and then detection was effected by sensitizing the treated film for about 10 seconds to 2 minutes. As shown in FIG. 2, KM1334 bound to FGF-8. Although FGF-8 has a theoretical value of 22 K dalton, it was observed as a band of around 30 K dalton due to addition of sugar chains and the like.

(2) Examination on the Inhibition of FGF-8 Activity by the Monoclonal Antibody

Figure 3:
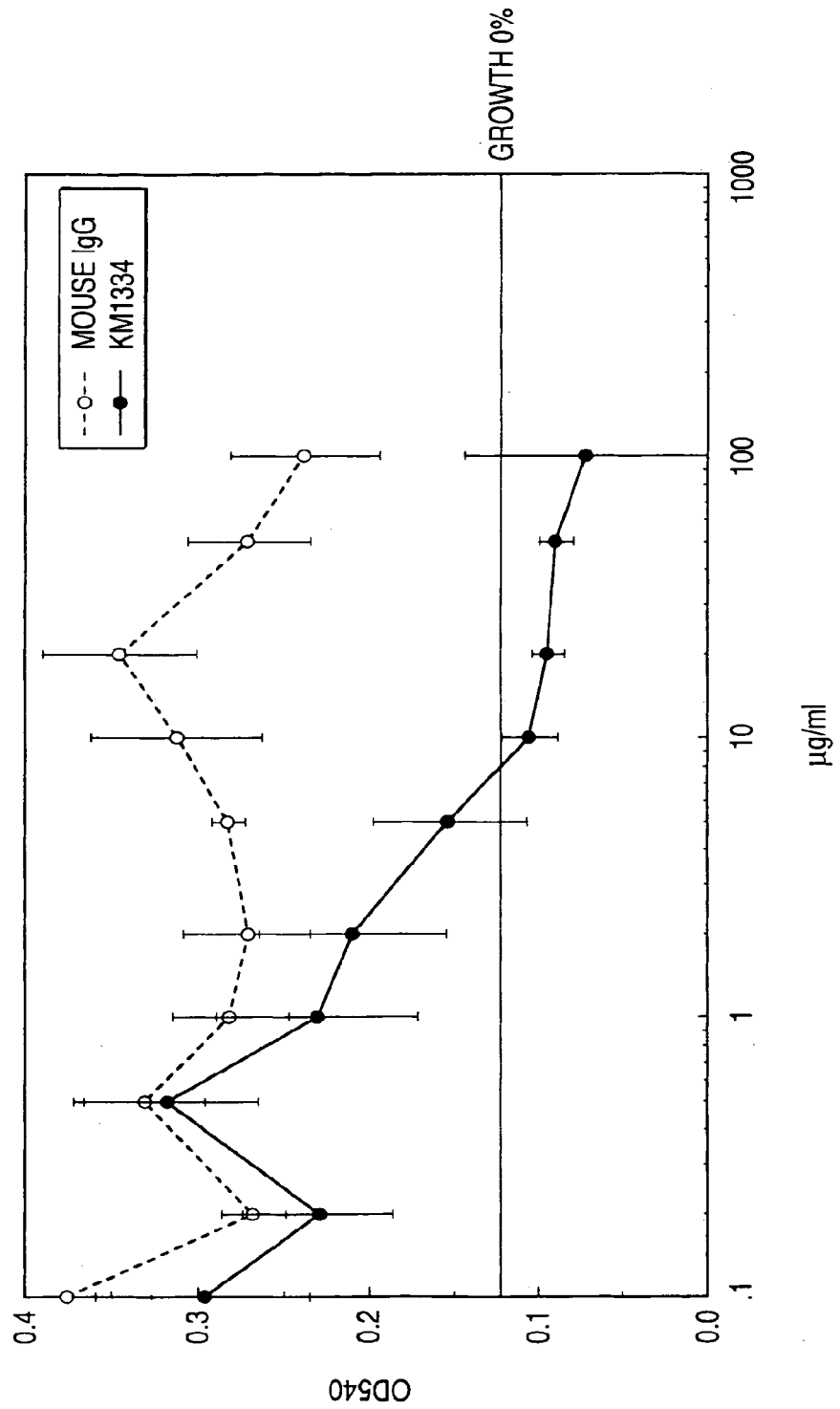
FIG. 3 shows the effect of anti-FGF-8 monoclonal antibody KM1334 in inhibiting the activity of FGF-8. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM1334.
Figure 4:
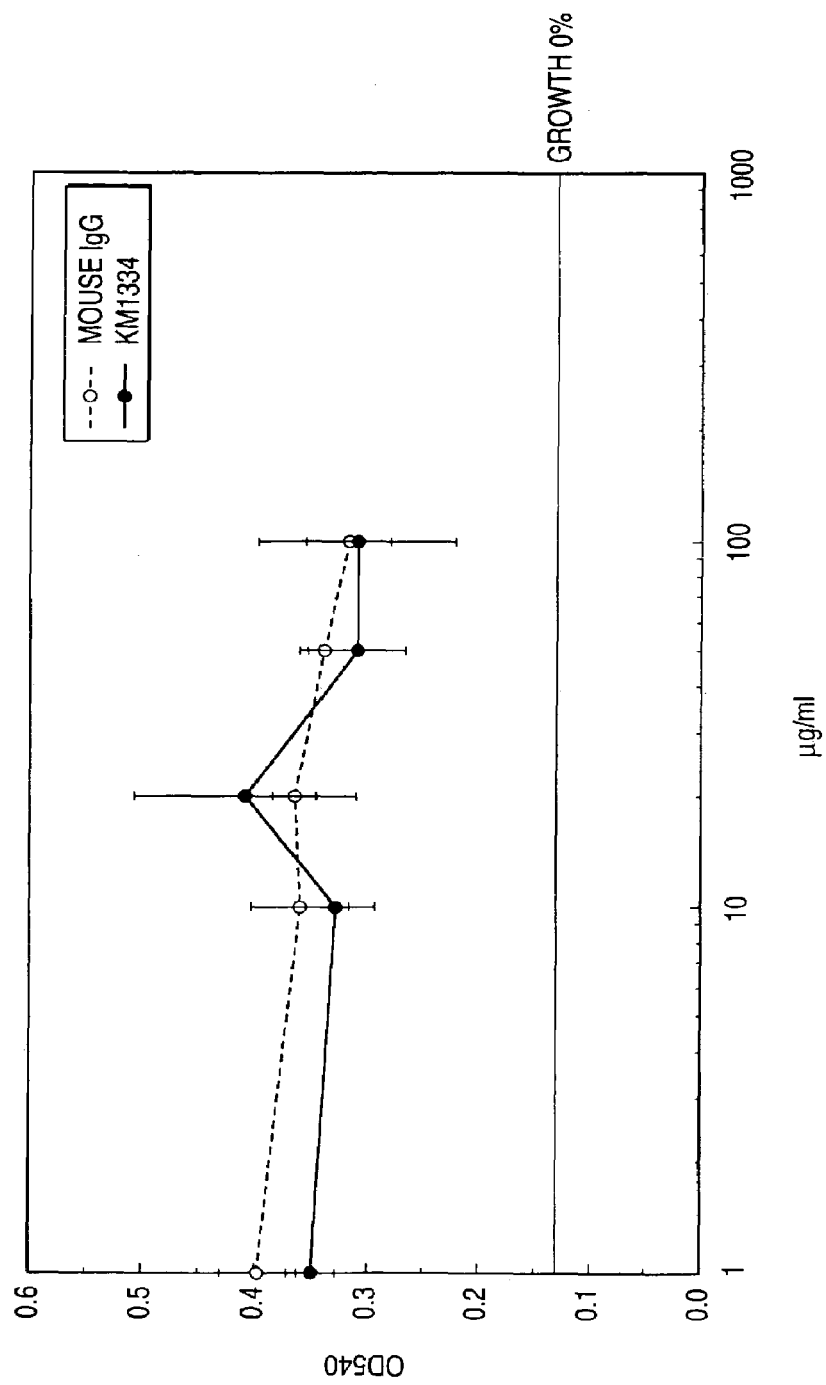
FIG. 4 shows the effect of anti-FGF-8 monoclonal antibody KM1334 in inhibiting the activity of bFGF. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM1334.
Figure 5:
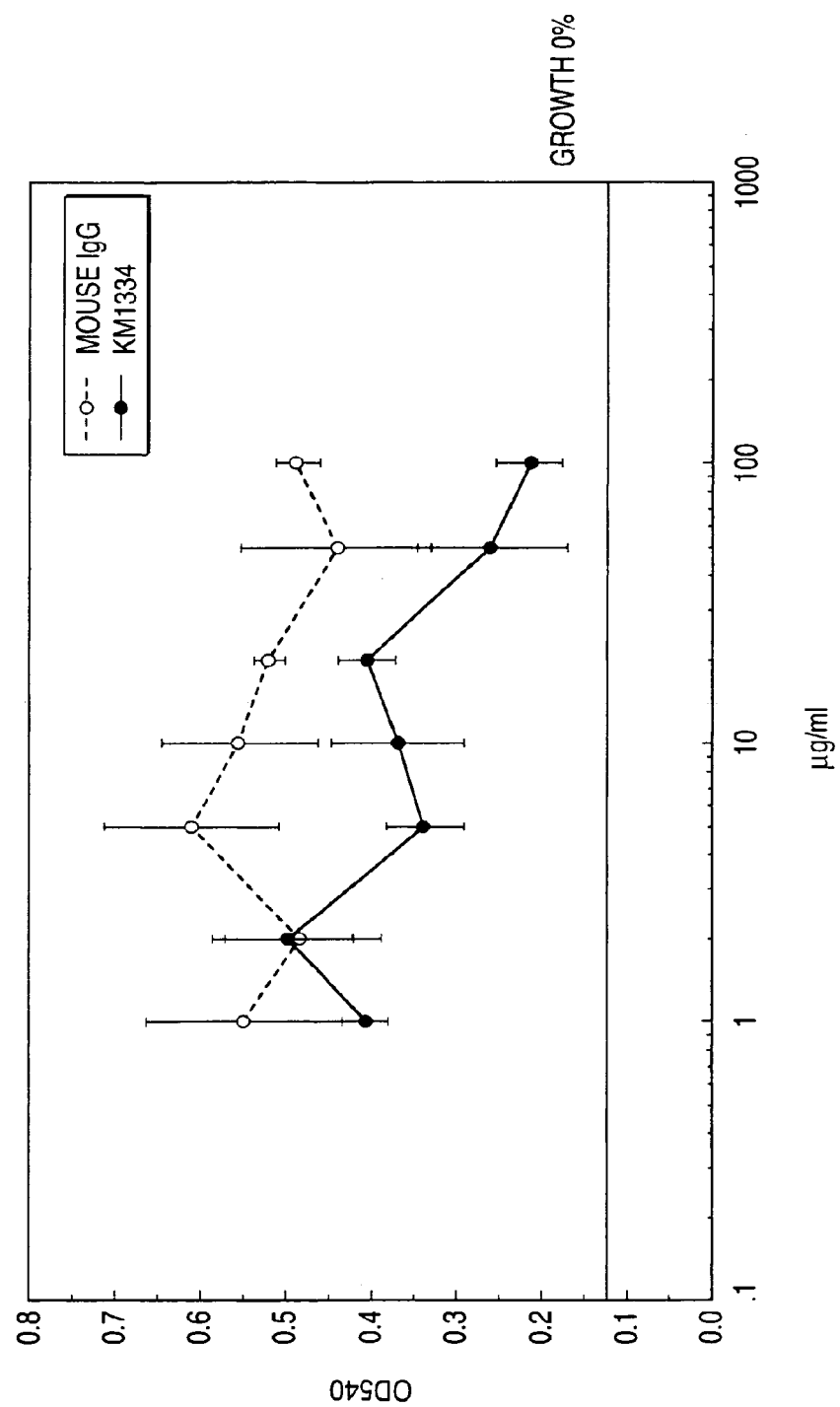
FIG. 5 shows the effect of anti-FGF-8 monoclonal antibody KM1334 in inhibiting the activity of testosterone. In the drawing, the line of growth at 0% indicates a value when neither the growth factor nor antibody were added. The dotted line indicates activity inhibition by purified mouse IgG used as a control antibody, and the solid line by anti-FGF-8 monoclonal antibody KM1334.

The ability of the anti-FGF-8 monoclonal antibody to inhibit FGF-8 activity was examined by a growth inhibition assay using the mouse breast cancer cell line SC-3 as the target cells. The SC-3 cells were cultured in a medium containing FGF-8 (50 ng/ml), testosterone (10 µl, manufactured by Nakalai Tesque) or basic fibroblast growth factor (hereinafter referred to as "bFGF" (1 ng/ml, manufactured by Pepro Tech Inc.)). In this case, the medium was supplemented in advance with the anti-FGF-8 monoclonal antibody KM1334 serially diluted to a final concentration of 0.1 to 100 µg/ml. As a control antibody, purified mouse IgG (manufactured by Sigma) was used. After 72 hours of culturing, the number of viable cells was measured by an MTT method. That is, a 5 mg/ml solution of MIT [3-(4,5-dimethyl-2-thiazonyl)-2,5-diphenyl-2H-tetrazolium bromide] in PBS was distributed in 10 µl portions into wells of culture plate and incubated at 37° C. for 4 to 5 hours, 0.04 N HCl-isopropanol was distributed in 150 µl portions into the resulting wells and then the plate was shaken at 37° C. for 1 to 2 hours. The formed pigment was then solubilized and its absorbance at $OD_{540}$ nm was measured. Results of inhibition against activity of FGF-8, bFGF and testosterone are shown in FIGS. 3, 4 and 5, respectively. As shown in FIG. 3, KM1334 inhibited the growth of SC-3 cells by FGF-8 in a dose-dependent manner, but, as shown in FIG. 4, KM1334 did not show dose-dependent inhibition of SC-3 cells by bFGF. In consequence, it was confirmed that KM 1334 inhibits the FGF-8 activity specifically. In addition, as shown in FIG. 5, KM1334 partially inhibited the growth of SC-3 cells by testosterone, but not completely at an antibody concentration of 100 µg/ml.

EXAMPLE 3

Preparation of Anti-FGF-8 Chimeric Antibody.

1. Isolation and Analysis of cDNA Encoding the V Region of Anti-FGF-8 Mouse Antibody (1) Preparation of mRNA from Hybridoma Cells Producing Anti-FGF-8 Mouse Antibody From $1 \times 10^1$ cells of a hybridoma KM1334 (FERM BP-5451) capable of producing a mouse antibody against FGF-8 (hereinafter referred to as "anti-FGF-8 mouse antibody"), about 8 µg of mRNA was prepared by using a mRNA preparation kit Fast Track mRNA Isolation Kit (manufactured by Invitrogen) according to the manufacture's instructions attached thereto.

(2) Preparation of Anti-FGF-8 Mouse Antibody H Chain and L Chain cDNA Libraries

From 5 µg of mRNA of KM1334 obtained in item 1 (1) of Example 1, cDNA having an EcoRI-NotI adapter on both termini was synthesized by using Time Saver cDNA Synthesis Kit (manufactured by Amersham Pharmacia Biotech) according to the manufacture's instructions attached thereto. Next, cDNA libraries were prepared by using λ ZAPII Cloning Kit (manufactured by Stratagene). First, a total amount of the cDNA was dissolved in 20 µl of sterile water and then fractionated by agarose gel electrophoresis to collect about 0.1 µg for each of a cDNA fragment of about 1.5 kb which corresponds to the H chain of IgG class antibody and a cDNA fragment of about 1.0 kb which corresponds to the L chain of κ class. Next, each of 0.1 µg of the cDNA fragment of about 1.5 kb and 0.1 µg of the cDNA fragment of about 1.0 kb was ligated with 1 µg of the λZAPII vector in which termini had been dephosphorylated with Calf Intestine Alkaline Phosphatase after digestion with a restriction enzyme EcoRI according to the manufacture's instructions attached thereto.

Using Gigapack II Packaging Extracts Gold (manufactured by Stratagene) according to the manufacture's instructions attached thereto, 4 µl of the each reaction solution after the ligation was packaged into A phage, and an appropriate amount thereof was infected with *Escherichia coli* XL1-Blue [*Biotechniques*, 5, 376 (1987)] to obtain about $8.1 \times 10^4$ and $5.5 \times 10^4$ of phage clones as H chain cDNA library and L chain cDNA library of KM1334, respectively. Next, each phage was fixed on a nylon membrane according to the conventional method [*Molecular Cloning; A Laboratory Manual*, Cold Spring Harbor Lab. Press, New York (1989)].

(3) Cloning of Anti-FGF-8 Mouse Antibody H Chain and L Chain cDNA

Using ECL Direct Nucleic Acid Labelling and Detection Systems (manufactured by Amersham Pharmacia Biotech) according to the manufacture's instructions attached thereto, clones of the H chain cDNA library and L chain cDNA library of KM1334 on the nylon membrane prepared in the item 1(2) of Example 3 were detected by using mouse antibody C region cDNA (H chain is a DNA fragment containing mouse Cγ1 cDNA [*J. Immunol.*, 146, 2010 (1991)] and L chain is a DNA fragment containing mouse Cκc cDNA [*Cell*, 22, 197 (1980)] as a probe to obtain 10 phage clones for each of the H chain and L chain clones which strongly reacted to the probe. Next, according to the manufacture's instructions of λ ZAPII Cloning Kit (manufactured by Stratagene), each phage clone was converted into plasmid by the in vivo excision method. Nucleotide sequence of cDNA contained in each of the thus obtained plasmids was determined by the dideoxy method [*Molecular Cloning: A Laboratory Manual*, Cold Spring Harbor Lab. Press, New York (1989)] using Big Dye Terminator Kit ver. 2 (manufactured by Applied Biosystems). As a result, a plasmid pKM1334H7-1 containing a full length functional H chain cDNA and a plasmid pKM1334L7-1 containing a full length functional L chain cDNA, in which ATG sequence considered to be an initiation codon is present in the 5'-terminal of the cDNA, were obtained.

(4) Analysis of Amino Acid Sequence of V Region of Anti-FGF-8 Mouse Antibody

A full nucleotide sequence of VH contained in the plasmid pKM1334H7-1 is shown in SEQ ID NO:3, its deduced full amino acid sequence is shown in SEQ ID NO:4, a full nucleotide sequence of VL contained in the plasmid pKM1334L7-1 is shown in SEQ ID NO:5, and its deduced full amino acid sequence is shown in SEQ ID NO:6. Based on the comparison with sequence data of known mouse antibodies [*Sequences of Proteins of Immunological Interest*, US Dept. Health and Human Services (1991)] and comparison with results of the analysis of N-terminal amino acid sequences of H chain and L chain of purified anti-FGF-8 mouse antibody KM1334, carried out by automatic Edman degradation using a protein sequencer PPSQ-10 (manufactured by Shimadzu Corporation), it was found that each cDNA thus isolated is a full length cDNA encoding the anti-FGF-8 mouse antibody KM1334 containing a secretory signal sequence, and the amino acid sequence at positions 1 to 19 of H chain shown in SEQ ID NO:4 and the amino acid sequence at positions 1 to 19 of L chain shown in SEQ ED NO:6 are the secretory signal sequences. Also, amino acid sequences of VH and VL excluding the secretory signal sequence are shown in SEQ ID NO:42 and SEQ ID NO:43, respectively.

Next, novelty of the amino acid sequences of VH and VL of the anti-FGF-8 mouse antibody KM1334 was examined. Using GCG Package (version 9.1, manufactured by Genetics Computer Group) as a sequence analyzing program, an amino acid sequence data base of known proteins [PIR-Protein (Release 56.0)] was retrieved by the BLAST method [*J. Mol. Biol*, 215, 403 (1990)]. As a result, completely identical sequences were not found regarding both H chain and L chain, so that it was confirmed that VH and VL of the anti-FGF-9 mouse antibody KM1334 are novel amino acid sequences.

In addition, CDRs of VH and VL of the anti-FGF-8 mouse antibody KM1334 were identified by comparing them with known antibody amino acid sequences. Amino acid sequences of CDR1, 2 and 3 of VH of the anti-FGF-8 mouse antibody KM1334 are shown in SEQ ID NOs:7, 8 and 9, respectively, and amino acid sequences of CDR1, 2 and 3 of VL in SEQ ID NOs:10, 11 and 12, respectively.

2. Stable Expression of Anti-FGF-8 Chimeric Antibody Using Animal Cells (1) Construction of Plasmid Containing VH cDNA of Anti-FGF-8 Chimeric Antibody Using 50 ng of the plasmid pKM1334H7-1 obtained in the item 1(3) of Example 1 as the template, synthetic DNA fragments having the nucleotide sequences shown in SEQ ID NOs:13 and 14 (manufactured by GENSET) were added as primers to give a final concentration of 0.3 µmol/l, and PCR was carried out by firstly heating 50 µl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase (manufactured by TOYOBO). The reaction product was purified, dissolved in sterile water and then allowed to react at 37° C. for 1 hour by using 10 units of restriction enzyme EcoRI (manufactured by Takara Shuzo). The reaction solution was fractionated by agarose gel electrophoresis to collect about 0.3 µg of an EcoRI fragment of about 0.48 kb (5'-terminal side is EcoRI, 3'-terminal side is blunt end).

Next, 3 µg of plasmid pBluescript SK(−) was allowed to react with 10 units of restriction enzyme EcoRI (manufactured by Takara Shuzo) and 10 units of restriction enzyme EcoRV (manufactured by Takara Shuzo) at 37° C. for 1 hour. The reaction solution was fractionated by agarose gel electrophoresis to collect about 2 µg of an EcoRI-EcoRV fragment of about 2.95 kb.

Figure 6:
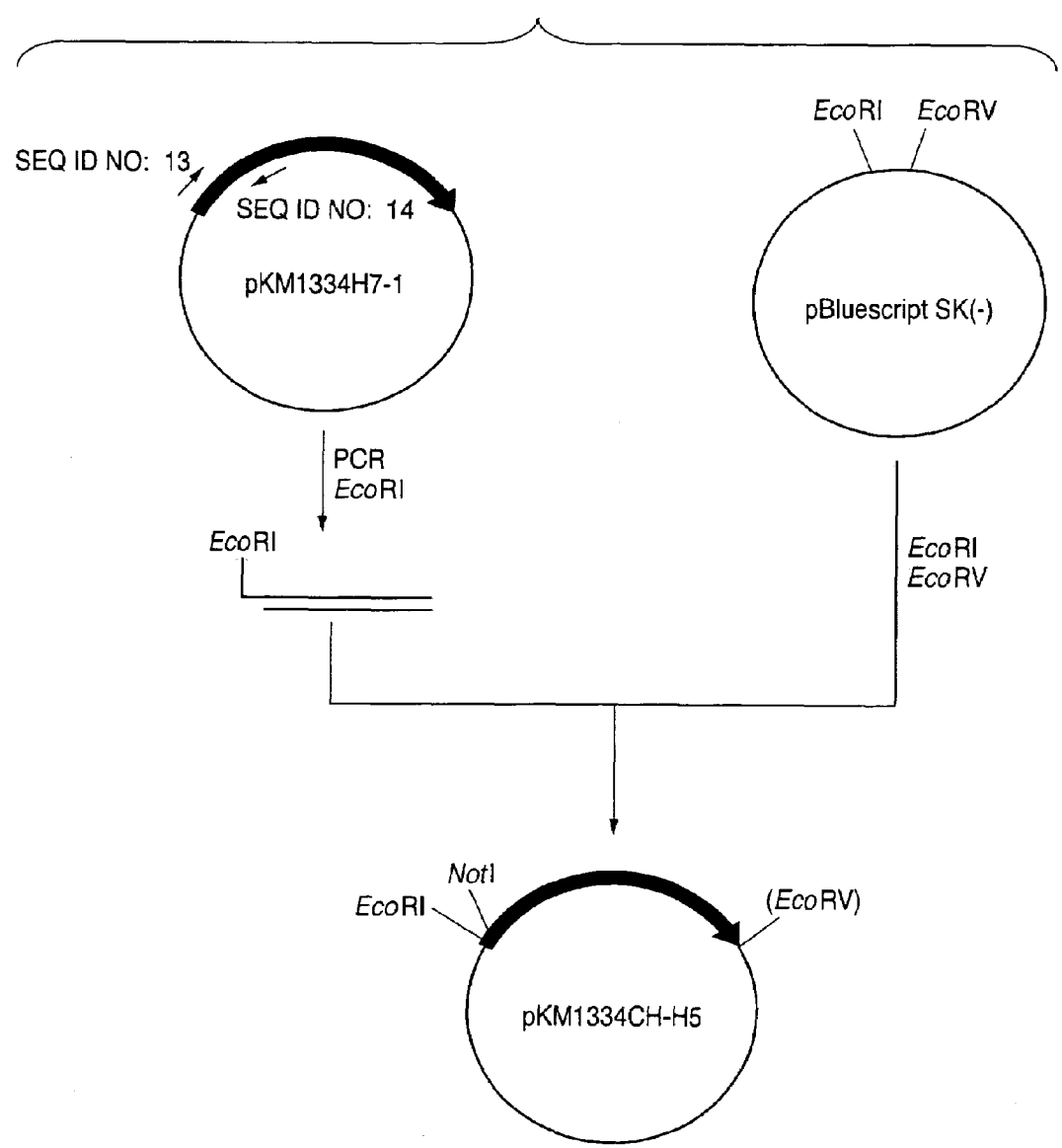
FIG. 6 shows construction steps of plasmid pKM1334CH-H5.

Next, 0.1 µg of the EcoRI fragment of VH cDNA and 0.1 µg of the EcoRI-EcoRV fragment derived from the plasmid pbluescript SK(−) obtained in the above were added to 10 µl in total volume of sterile water and ligated by using Ligation High (manufactured by TOYOBO). Using the thus obtained recombinant plasmid DNA solution, *E. coli* XL1-Blue was transformed to obtain a plasmid pKM1334CH-H5 shown in FIG. 6 containing VH cDNA of anti-FGF-8 chimeric antibody.

(2) Construction of Plasmid Containing VL cDNA of Anti-FGF-8 Chimeric Antibody

Using 50 ng of the plasmid pKM1334L7-1 obtained in the item 1(3) of Example 1 as the template, synthetic DNA fragments having the nucleotide sequences shown in SEQ ID NOs:15 and 16 (manufactured by GENSET) were added as primers to give a final concentration of 0.3 µmol/l, and PCR was carried out by firstly heating 50 µl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase (manufactured by TOYOBO). The reaction product was purified, dissolved in sterile water and then allowed to react at 37° C. for 1 hour by using 10 units of restriction enzyme EcoRI (manufactured by Takara Shuzo). The reaction solution was fractionated by agarose gel electrophoresis to collect about 0.3 µg of an EcoRI fragment of about 0.45 kb (5'-terminal side is EcoRI, 3'-terminal side is blunt end).

Figure 7:
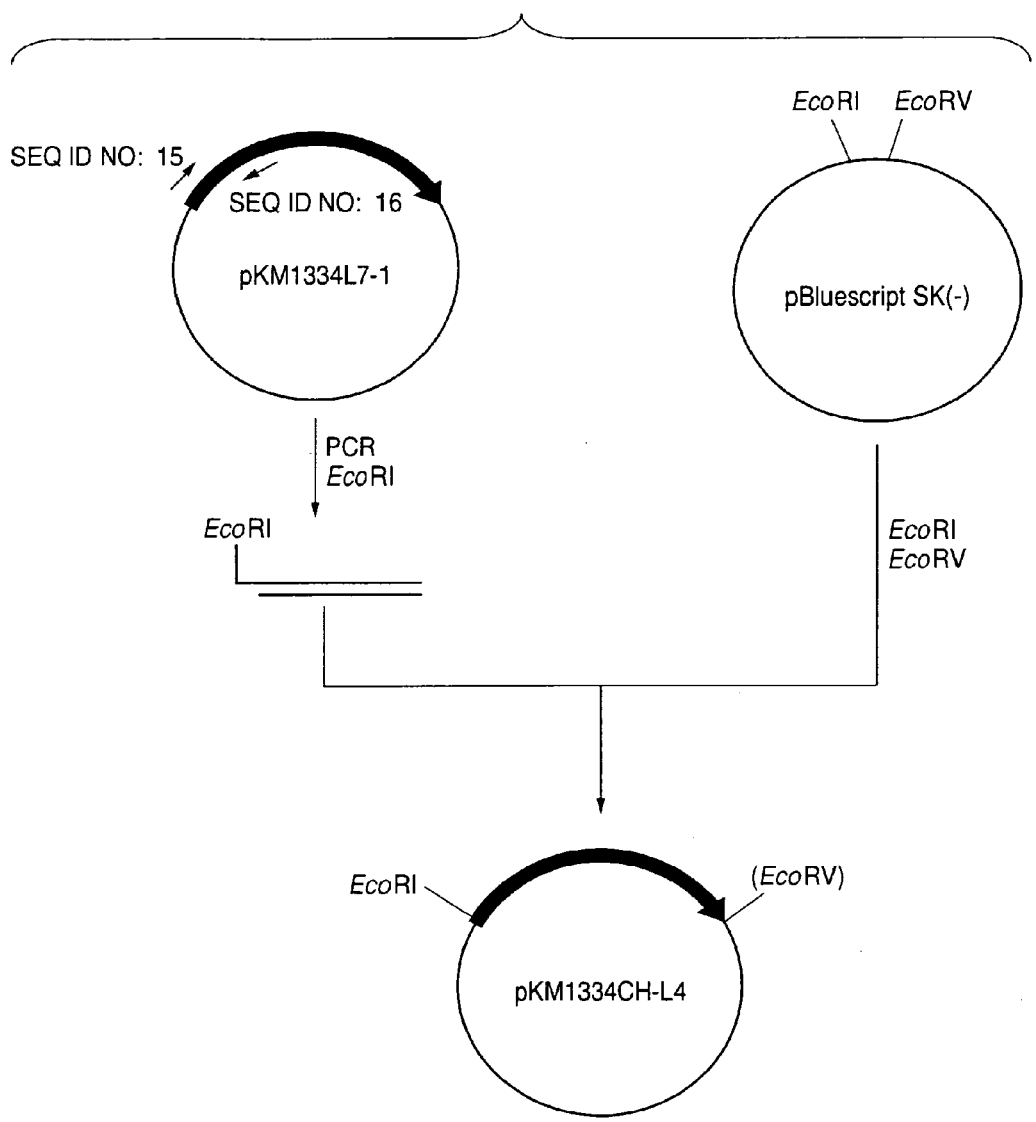
FIG. 7 shows construction steps of plasmid pKM1334CH-LA.

Next, 0.1 µg of the EcoRI fragment of VL cDNA and 0.1 µg of the EcoRI/EcoRV fragment derived from the plasmid pBluescript SK(−) both obtained in the above were added to 10 µl in total volume of sterile water and ligated using Ligation High (manufactured by TOYOBO). Using the thus obtained recombinant plasmid DNA solution, *E. coli* XL1-Blue was transformed to obtain a plasmid pKM1334CH-LA shown in FIG. 7 containing VL cDNA of anti-FGF-8 chimeric antibody.

(3) Construction of Anti-FGF-8 Chimeric Antibody Expression Vector pKANTEX1334

Using the humanized antibody expression vector pKANTEX93 described in WO97/10354 and the plasmids pKM1334CH-H5 and pKM1334CH-LA obtained in the items 2(1) and (2) of Example 3, an anti-FGF-8 chimeric antibody expression vector pKANTEX1334 was constructed as follows.

A reaction was carried out by mixing 3 µg of the plasmid pKM1334CH-H5 obtained in the item 2(1) of Example 3 with 10 units of restriction enzyme NotI (manufactured by New England Biolabs) and 10 units of restriction enzyme ApaI (manufactured by Takara Shuzo) at 37° C. for 1 hour. The reaction solution was fractionated by agarose gel electrophoresis to collect about 0.2 µg of a NotI-ApaI fragment of about 0.48 kb.

Next, 3 µg of the humanized antibody expression vector pKANTEX93 was allowed to react with 10 units of restriction enzyme ApaI (manufactured by Takara Shuzo) and 10 units of restriction enzyme NotI (manufactured by New England Biolabs) at 37° C. for 1 hour. The reaction solution was fractionated by agarose gel electrophoresis to collect about 2 µg of an ApaI-NotI fragment of about 12.8 kb.

Figure 8:
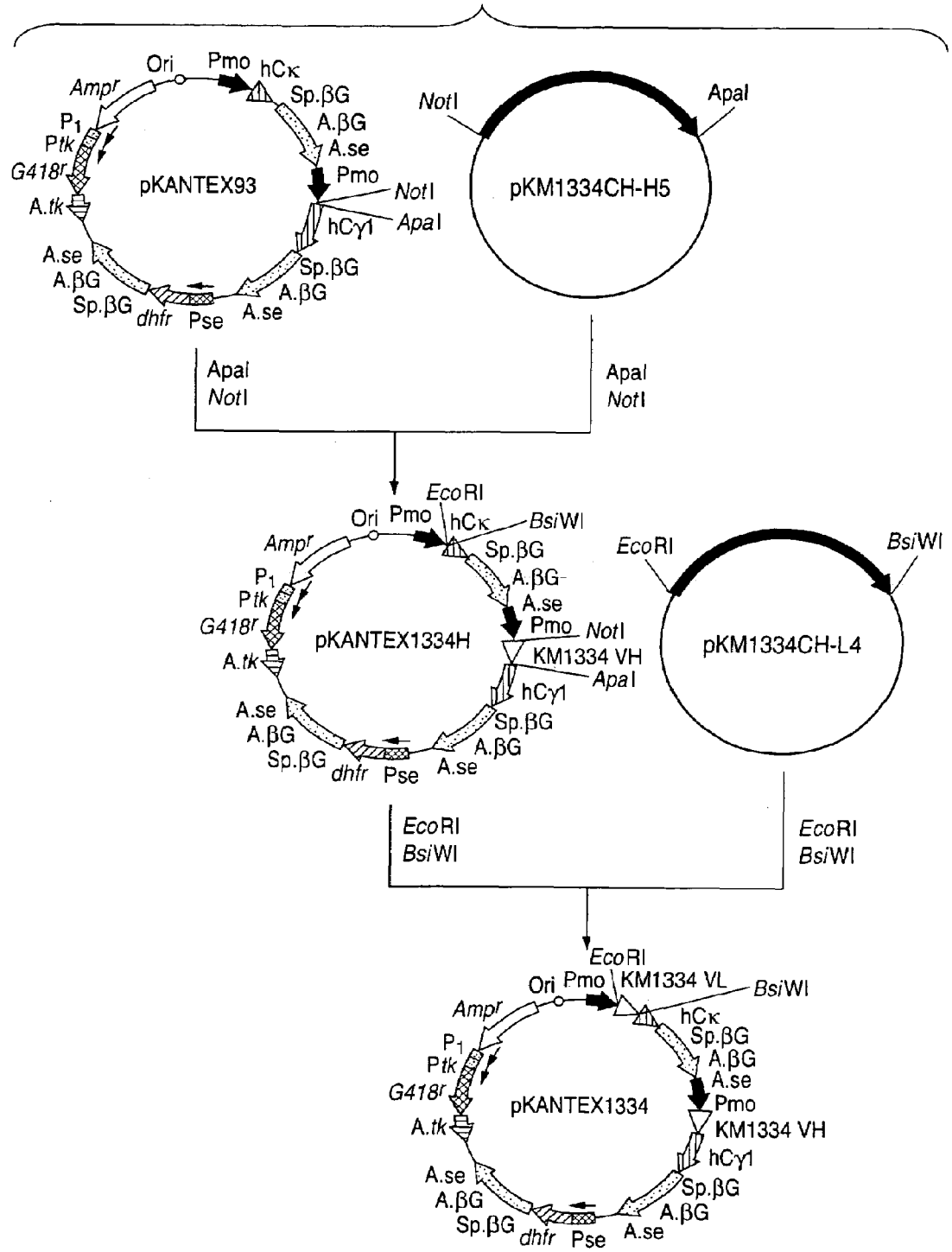
FIG. 8 shows construction steps of plasmid pKANTEX1334.

Next, 0.1 µg of the NotI-ApaI fragment derived from the plasmid pKM1334CH-H5 and 0.1 µg of the NotI-ApaI fragment derived from the plasmid pKANTEX93 were added to 10 µl in total volume of sterile water and ligated by using Ligation High (manufactured by TOYOBO). Using the thus obtained recombinant plasmid DNA solution, *E. coli* XL1-Blue was transformed to obtain the plasmid pKANTEX1334H shown in FIG. 8.

Next, 3 µg of the plasmid pKM1334CH-L4 obtained in the item 2(2) of Example 3 was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 0.2 µg of an EcoRI-BsiWI fragment of about 0.45 kb.

Next, 3 µg of the plasmid pKANTEX1334H obtained in the above was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 2 µg of an EcoRI-BsiWI fragment of about 13.30 kb.

Next, 0.1 µg of the EcoRI-BsiWI fragment derived from the plasmid pKM1334CH-IA and 0.1 lag of the EcoRI-BsiWI fragment derived from the plasmid pKANTEX1334H were added to 10 Al in total volume of sterile water and ligated using Ligation High (manufactured by TOYOBO). Using the thus obtained recombinant plasmid DNA solution, the *E. coli* XL1-Blue was transformed to obtain the plasmid pKANTEX1334 shown in FIG. 8.

Using 400 ng of the thus obtained plasmid, analysis of its nucleotide sequence was carried out by the dideoxy method [Molecular Cloning A Laboratory Manual, Cold Spring Harbor Lab. Press, New York (1989)] using Big Dye Terminator Kit ver. 2 (manufactured by Applied Biosystems), thereby confirming that a plasmid into which the DNA of interest had been cloned was obtained.

(4) Stable Expression of Anti-FGF-8 Chimeric Antibody Using CHO-DG44 Cell

Using the anti-FGF-8 chimeric antibody expression vector pKANTEX1334 obtained in the item 2(3) of Example 3, expression of anti-FGF-8 chimeric antibody in CHO/DG44 cell [*Proc. Natl. Acad. Sci. USA*, 17, 4216 (1980)] was carried out as follows.

After 10 µg of the plasmid pKANTEX1334 was introduced into $1.6 \times 10^6$ cells of CHO/DG44 cell by electroporation [*Cytotechnology*, 3, 133 (1990)], the cells were suspended in 10 to 30 ml of IMDM-1×HT supplement-dFBS (10) [IMDM medium containing 10% of dialyzed fetal bovine serum (dFBS) and 1×HT supplement, (all manufactured by GIBCO)] and dispensed at 100 μl/well into a 96 well microtiter plate (manufactured by IWAKI). After culturing at 37° C. for 24 hours in a 5% $CO_2$ incubator, the culture medium was changed to IMDM-dFBS(10) prepared by eliminating HT supplement alone, followed by culturing for 1 to 2 weeks. Culture supernatants were recovered from wells where resistant colonies were grown and became confluent, and the antigen binding activity of anti-FGF-8 chimeric antibodies in the supernatants was measured by the ELISA shown in the item 2(6) of Example 3.

Regarding the transformants of wells in which expression of anti-FGF-8 chimeric antibodies was found in the culture supernatants, in order to increase antibody expression quantity using a dhfr gene amplification system, they were inoculated into a 24 well plate and cultured for 2 weeks in IMDM-dFBS(10) medium containing 50 mol/l methotrexate (MIX, manufactured by SIGMA) which is an inhibitor of the dhfr gene product dihydrofolate reductase. The MTX concentration was further increased to 200 μmol/l and then to 500 μmol/l, followed by culturing for 2 weeks at each increasing step to induce transformants showing 500 μmol/l MTX resistance. When the transformants became confluent in wells, the antigen binding activity of anti-FGF-8 chimeric antibodies in the supernatants was measured by the ELISA shown in the item 2(6) of Example 3. Finally, transformants capable of growing in the IMDM-dFBS(10) medium containing 500 μmol/l MTX and of highly expressing anti-FGF-8 chimeric antibodies were obtained. Regarding the thus obtained transformants, single cell isolation (cloning) was carried out by limiting dilution method, and a transformed cell clone showing the highest expression of anti-FGF-8 chimeric antibody was named KM3034. Also, the KM3034 has been deposited on Dec. 26, 2001, as FERM BP-7836 in International Patent Organism Depositary, National Institute of Advanced Industrial Science and Technology (AIST Tsukuba Central 6, 1-1, Higashi I-Chome Tsukuba-shi, Ibaraki-ken 305–8566 Japan).

(5) Stable Expression of Anti-FGF-8 Chimeric Antibody Using YB2/0 Cell

Using the anti-FGF-8 chimeric antibody expression vector pKANTEX1334 obtained in the item 2(3) of Example 3, expression of anti-FGF-8 chimeric antibody in YB2/0 cell (ATCC CRL1662) was carried out as follows.

After 10 μg of the plasmid pKANTEX1334 was introduced into $4 \times 10^6$ cells of YB2/0 cell (ATCC CRL1662) by electroporation [*Cytotechnology*, 3, 133 (1990)], the cells were suspended in 40 ml of Hybridoma-SFM-FBS(5) [Hybridoma-SFM medium (manufactured by Gibco) containing 5% fetal bovine serum (FBS; manufactured by PAA Laboratories)] and dispensed at 200 μl/well into a 96 well culture plate (manufactured by Sumitomo Bakelite). After culturing at 37° C. for 24 hours in a 5% $CO_2$ incubator, G418 was added to give a concentration of 1 mg/ml, followed by culturing for 1 to 2 weeks. Culture supernatants were recovered from wells in which colonies of transformants showing G418-resistance were grown and their propagation was confirmed, and the antigen binding activity of anti-FGF-8 chimeric antibodies in the supernatants was measured by the ELISA shown in the item 2(6) of Example 3.

Regarding the transformants of wells in which expression of anti-FGF-8 chimeric antibodies was found in the culture supernatants, in order to increase antibody expression quantity using a dhfr gene amplification system, they were suspended in the Hybridoma-SFM-FBS(5) medium containing 1 mg/ml G418 and 50 nmol/l MTX (manufactured by SIGMA) to give a density of 1 to $2 \times 10^5$ cells/ml, and dispensed at 1 ml into a 24 well plate (manufactured by Greiner). By culturing at 37° C. for 1 to 2 weeks in a 5% $CO_2$ incubator, transformants showing 50 mol/l MTX resistance were induced. The antigen binding activity of anti-FGF-8 chimeric antibodies in the culture supernatants in wells where proliferation of transformants was observed was measured by the ELISA shown in the item 2(6) of Example 3.

Regarding the transformants of wells in which expression of anti-FGF-8 chimeric antibodies was found in the culture supernatants, the MTX concentration was increased by the same method as described above, and a transformant 5-D capable of growing in the Hybridoma-SFM-FBS(5) medium containing 1 mg/ml G418 and 200 mol/l MTX at final concentrations and of highly expressing anti-FGF-8 chimeric antibody was obtained. Regarding the thus obtained transformant, cloning was carried out by limiting dilution method to obtain a transformed cell line showing the highest expression of anti-FGF-8 chimeric antibody. The thus obtained transformed cell was named KM3334.

(6) Binding Activity of Antibody to FGF-8 Peptide (ELISA)

Compound 1 (SEQ ID NO:17) was selected as human FGF-8 peptide with which the anti-FGF-8 antibody can react. In order to use in the activity measurement by ELISA, its conjugate with bovine serum albumin (BSA, manufactured by Nacalai Tesque) was prepared and used as the antigen. That is, 100 μl of 25 mg/ml SMCC [4-N-maleimidomethyl)cyclohexane-1-carboxylic acid N-hydroxysuccinimide ester] (manufactured by Sigma)-DMSO solution was added dropwise under stirring to 900 μl of PBS solution containing 10 mg of BSA, followed by slowly stirring for 30 minutes. After 1 ml of the reaction solution was applied to a gel filtration column such as NAP-10 column which had been equilibrated with 25 ml of PBS, the eluate eluted with 1.5 ml of PBS was used as a BSA-SMCC solution. The BSA concentration of each fraction was measured based on the absorbance at 280 nm. Next, 200 μl of DMSO was added to 1.0 mg of Compound 1 which was then completely dissolved by adding 800 μl of PBS, the above BSA-SMCC solution (2.5 mg as BSA) added thereto under stirring, followed by slowly stirring at room temperature for 3 hours. The reaction solution was dialyzed overnight at 4° C. against PBS, sodium azide was added thereto to give a final concentration of 0.05%, the mixture was filtered through a 0.22 μm filter, and the filtrate was used as a BSA-compound 1 solution.

The conjugate prepared in the above was dispensed at 50 μl/well into a 96 well plate for ELISA (manufactured by Greiner) at a concentration of 0.5 to 1.0 μg/ml and allowed to stand for adsorption overnight at 4° C. After washing with PBS, 1% BSA-containing PBS (BSA-PBS) was added at 100 μl/well and allowed for blocking of remaining active groups to react at room temperature for 1 hour. After washing each well with 0.05% Tween-containing PBS (Tween-PBS), culture supernatants of transformants or purified antibodies were added at 50 μl/well and allowed to react at room temperature for 1 hour. After the reaction, each well was washed with Tween-PBS and then a peroxidase-labeled goat anti-human IgG (H & L) antibody solution (manufactured by American Qualex) diluted 3,000 to 6,000-folds with BSA-PBS was added as a secondary antibody solution at 50 μl/well and allowed to react at room temperature for 1 hour. After the reaction and subsequent washing with Tween-PBS, an ABTS substrate solution [a solution prepared by dissolving 0.55 g of 2,2'-azinobis(3-ethylbenzothiazoline-6-sulfonic acid) ammonium in 1 L of 0.1 M citrate buffer (pH 4.2)

and adding 1 μl/ml hydrogen peroxide just before use] was added at 50 μl/well for color development, and the reaction was stopped by adding 5% SDS solution at 50 μl/well. Thereafter, absorbance at 415 nm (OD415) was measured.

4. Purification of Anti-FGF-8 Chimeric Antibody (1) Culturing of CHO-DG44 Cell-derived Expression Cell and Purification of Antibody The anti-FGF-8 chimeric antibody-expressing transformed cell line KM3034 obtained in the item 2(4) of Example 3 was suspended in IMDM-dFBS(10) medium containing 500 nmol/l MTX to give a density of 1 to $2 \times 10^5$ cells/ml and dispensed at 40 ml into a 175 cm² flask (manufactured by Greiner). When the cells became confluent by culturing at 37° C. for 5 to 7 days in a 5% $CO_2$ incubator, the culture supernatant was discarded and the cells were washed with 20 ml of PBS. After discarding PBS and subsequently adding 40 ml of EXCELL301 medium (manufactured by JRH), the cells were cultured at 37° C. for 7 to 14 days in a 5% $CO_2$ incubator and then the culture supernatant was recovered. Using Prosep-A (manufactured by Millipore) column and according to the manufacture's instructions attached thereto, the anti-FGF-8 chimeric antibody was purified from the culture supernatant. The thus obtained anti-FGF-8 chimeric antibody was named KM3034.

(2) Culturing of YB2/0 Cell-Derived Expression Cells and Purification of Antibody The anti-FGF-8 chimeric antibody-expressing transformed cell line KM3334 obtained in the item 2(5) of Example 3 was cultured in Hybridoma-SFM (manufactured by Gibco) medium containing 200 nmol/l MTX and 5% in concentration of Daigo's GF21 (manufactured by Wako Pure Chemical Industries) at 37° C. in a 5% $CO_2$ incubator using a 175 cm² flask (manufactured by Creiner). Using Prosep-A (manufactured by Millipore) column and according to the manufacture's instructions attached thereto, the anti-FGF-8 chimeric antibody was purified from the culture supernatant which had been recovered after 8 to 10 days of the culturing. The thus obtained anti-FGF-8 chimeric antibody was named KM3334.

5. Analysis of Purified Anti-FGF-8 Chimeric Antibody

About 4 μg of each of the two anti-FGF-8 chimeric antibodies KM3034 and KM3334 expressed in respective animal cells, purified and obtained in the item 3 of Example 3 was subjected to SDS-PAGE according to the known method [*Nature*, 227, 680 (1970)] to analyze their molecular weights and purity. In each of the purified anti-FGF-8 chimeric antibodies, a single band of about 150 Kd in molecular weight was found under non-reducing conditions, and two bands of about 50 Kd and about 25 Kd were found under reducing conditions. These molecular weights almost coincided with the molecular weights deduced from the cDNA nucleotide sequences of H chain and L chain of the antibody (H chain; about 49 Kd, L chain: about 23 Kd, whole molecule: about 144 Kd), and also coincided with the reports stating that the IgG type antibody has a molecular weight of about 150 Kd under non-reducing conditions and is degraded into H chains having a molecular weight of about 50 Kd and L chains having a molecular weight of about 25 Kd under reducing conditions due to cleavage of S—S bond in the molecule [*Antibodies: A Laboratory Manual*, Cold Spring Harbor Laboratory, Chapter 14 (1988); *Monoclonal Antibodies: Principles and Practice*, Academic Press Limited (1996)], so that it was confirmed that each anti-FGF-8 chimeric antibody was expressed and purified as an antibody molecule of correct structure.

6. Activity Evaluation of Purified Anti-FGF-8 Chimeric Antibodies

Figure 9:
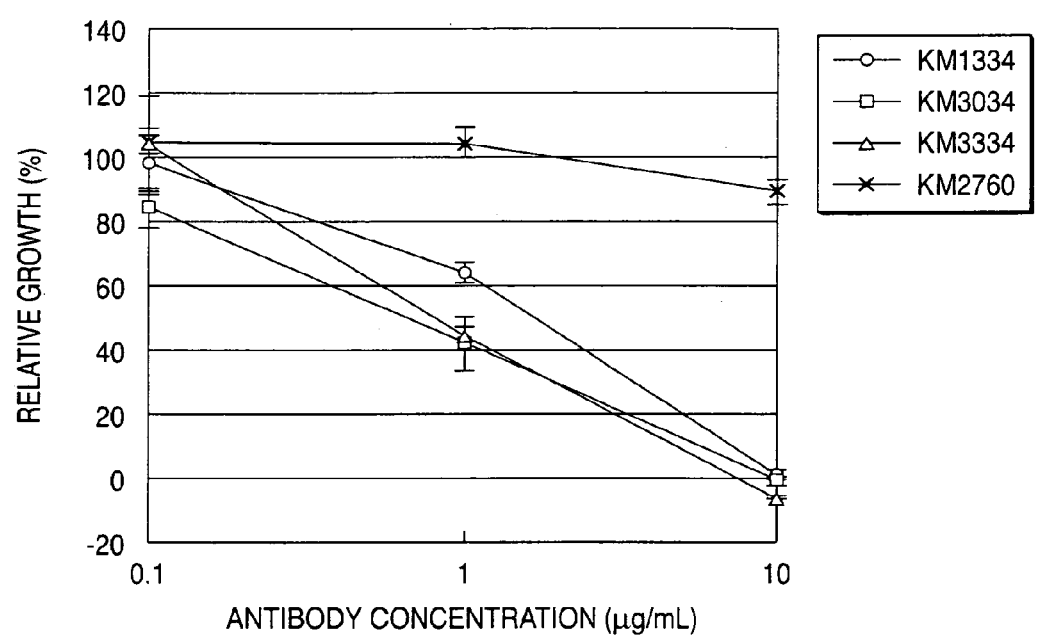
FIG. 9 shows neutralization activities of anti-FGF-8 mouse antibody KM1334 and anti-FGF-8 chimeric antibodies KM3034 and KM3334 on the FGF-8-dependent growth of mouse breast cancer cell line SC-3 cells. The abscissa and the ordinate indicate antibody concentration (µg/ml) and relative growth (%) when the growth by the addition of FGF-8 alone is defined as 100%, respectively. "○", "□", "Δ" and "x" indicate activities of KM1334, KM3034, KM3334 and KM2760 as a negative control, respectively.

FGF-8 neutralizing activity of purified anti-FGF-8 chimeric antibodies was evaluated by measuring the following FGF-8-dependent growth inhibitory effect of a mouse breast cancer cell line SC-3 [*Proc. Natl. Acad. Sci. USA*, 89, 8928 (1992)]. That is, the SC-3 cell was suspended at a density of $3.0 \times 10^4$ cells/ml in DMEM:Ham's F12 (1:1) medium (manufactured by Gibco) containing 2% activated carbon-treated FBS and inoculated at 150 μl ($4.5 \times 10^3$ cells)/well into a 96 well plate. After culturing at 37° C. for 18 hours in a 5% $CO_2$ incubator, the medium was exchanged by using 100 μl/well of a test medium. The test medium was prepared by dissolving 50 ng/ml FGF-8 (manufactured by R&D) and anti-FGF-8 chimeric antibody in each diluted concentration in DMEM:Ham's F12 (1:1) medium containing 0.1% BSA. Also, the chimeric antibody KM2760 for human chemokine receptor CCR4 described in WO/0164754 was used as a negative control antibody. After culturing at 37° C. for 48 hours in a 5% $CO_2$ incubator, the medium was exchanged with a freshly prepared test medium, followed by culturing for 48 hours. WST-1 reagent (manufactured by Roche) was added at 10 μl/well, followed by light stirring, and then $OD_{450/650}$ was measured after culturing at 37° C. for 1 hour in the 5% $CO_2$ incubator. In FIG. 9, the abscissa and the ordinate show the concentration of the added antibody and the relative growth (%) to the growth after addition of 50 ng/ml FGF-8 alone, respectively. The relative growth (%) to the growth after addition of 50 ng/ml FGF-8 alone was calculated by the following equation:

Relative growth (%) to the growth after addition of
FGF-8=[(OD value after addition of FGF-8 and
antibody)–(OD value before addition of FGF-8
and antibody)]/[(OD value after addition of
FGF-8 alone)–(OD value before addition of
FGF-8 and antibody)]×100

As shown in FIG. 9, each of the anti-FGF-8 mouse antibody KM1334 and anti-FGF-8 chimeric antibodies KM3034 and KM3334 showed similar SC-3 cell growth inhibitory activity so that reduction of the activity by chimeric antibody formation was not found.

EXAMPLE 4

Preparation of Human CDR-grafted Antibody for FGF-8:

1. Construction of cDNA Encoding VH and VL of Human CDR-grafted Antibody Against FGF-8

(1) Design of Amino Acid Sequences of VH and VL of Human CDR-grafted Antibody Against FGF-8

First, amino acid sequence of VH of a human CDR-grafted antibody against FGF-8 (anti-FGF-9 CDR-grafted antibody) was designed as follows. In order to graft the amino acid sequence of CDR in VH of the anti-FGF-8 mouse antibody KM1334 identified in the item 1(4) of Example 3, the amino acid sequence of FR in VH of a human antibody was selected. Kabat et al. have classified VH of various known human antibodies into three subgroups (HSG I to III) based on the homology of the amino acid sequences and then reported consensus sequences among respective subgroups [*Sequences of Proteins of Immunological Interest*, US Dep. Health and Human Services (1991)]. Since these consensus sequences have a possibility that the immunogenicity is reduced in human, it was decided to design the amino acid sequence of VH of an anti-FGF-8 CDR-grafted antibody based on these consensus sequences. In order to prepare an anti-FGF-8 CDR-grafted antibody having higher activity in designing it, it was decided to select the amino acid sequence of FR having the highest homology with the amino acid sequence of FR in VH of KM1334, among the amino acid sequences of FRs in consensus sequences of the three subgroups of VH of human antibodies. Results of the homology search are shown in Table 1. As shown in Table 1, the amino acid sequence of FR in the VH region of KM1334 showed the highest homology with the subgroup I.

TABLE 1

Homology between the amino acid sequence of FR in consensus sequence of each subgroup of human antibody VH and the amino acid sequence of FR in VH of KM1334

| HSG I | HSG II | HSG III |
|---|---|---|
| 79.3% | 51.7% | 59.8% |

Based on the above results, an amino acid sequence HV.0 of VH of the anti-FGF-8 CDR-grafted antibody describe in SEQ ID NO 18 was designed by grafting the amino acid sequence of CDR in VH of the anti-FGF-8 mouse antibody KM1334 to an appropriate position of the amino acid sequence of FR in the consensus sequence of subgroup I of VH of the human antibody.

Next, the amino acid sequence of VL of an anti-FGF-8 CDR-grafted antibody was designed as follows. In order to graft the amino acid sequence of CDR in VL of the anti-FGF-8 mouse antibody KM1334 identified in the item 1(4) of Example 3, the amino acid sequence of FR in VL of a human antibody was selected. Kabat et al. have classified the VL of various known human antibodies into four subgroups (HSG I to IV) based on the homology of the amino acid sequences and then reported consensus sequences among respective subgroups [*Sequences of Proteins of Immunological Interest*, US Dep. Health and Human Services (1991)]. Accordingly, similar to the case of VH, the amino acid sequence of FR having the highest homology with the amino acid sequence of FR in VL of KM1334 was selected from the amino acid sequences of FRs in consensus sequences of the four subgroups of VL of human antibodies.

Results of the homology search are shown in Table 2. As shown in Table 2, the amino acid sequence of FR in VL of KM1334 showed the highest homology with the subgroup II.

TABLE 2

Homology between the amino acid sequence of FR in consensus sequence of each subgroup of VL of human antibody and the amino acid sequence of FR in VL of KM1334

| HSG I | HSG II | HSG III | HSG IV |
|---|---|---|---|
| 66.3% | 83.8% | 66.2% | 73.8% |

Based on the above results, the amino acid sequence LV.0 of VL of the anti-FGF-8 CDR-grafted antibody shown in SEQ ID NO:19 was designed by grafting the amino acid sequence of CDR in VL of the anti-FGF-8 mouse antibody KM1334 to an appropriate position of the amino acid sequence of FR in the consensus sequence of subgroup II of VL of the human antibody.

The thus designed amino acid sequence HV.0 of VH and amino acid sequence LV.0 of VL of the anti-FGF-8 CDR-grafted antibody are sequences in which only the CDR amino acid sequence of the anti-FGF-8 mouse antibody KM1334 is grafted to the amino acid sequence of FR in the selected human antibody. In many cases, in the case of human CDR-grafted antibodies, the binding activity is decreased by grafting of the amino acid sequence of CDR in the mouse antibody alone. In order to avoid this reduction, among the amino acid residues in FR different between a human antibody and a mouse antibody, amino acid residues considered to have influences on the binding activity are grafted together with the amino acid sequence of CDR. Accordingly, an attempt was also made in this Example to identify the amino acid residues in FR considered to have influences on the binding activity.

First, a three-dimensional structure of an antibody V region comprising the amino acid sequence HV.0 of VH and the amino acid sequence LV.0 of VL of the anti-FGF-8 CDR-grafted antibody designed in the above (HV0LV0) was constructed by using computer modeling techniques. The preparation of three-dimensional structure coordinates was carried out by using software AbM (manufactured by Oxford Molecular), and the display of three-dimensional structure was carried out by using software ProExplore (manufactured by Oxford Molecular) or RasMol (manufactured by Glaxo) according to the respective manufacture's instructions attached thereto. Also, a computer model of the three-dimensional structure of the V region of anti-FGF-8 mouse antibody KM1334 was constructed in the same manner. In addition, a three-dimensional structure model of a modified antibody comprising an amino acid sequence in which amino acid residues different from anti-FGF-8 mouse antibody KM1334 in the amino acid sequences of FRs in VH and VL of HV0LV0 were substituted by the amino acid residues of positions corresponding to the anti-FGF-8 mouse antibody KM1334 in order, was constructed, and three-dimensional structures of V regions of the anti-FGF-8 mouse antibody KM1334, HV0LV0 and modified structure were compared. As a result, as residues among the amino acid residues of FRs in HV0LV0 considered to have influences on the antibody activity by changing three-dimensional structure of the antigen-binding region, Lys at position 12, Lys at position 13, Ala at position 40, Pro at position 41, Met at position 48, Val at position 68, Ile at position 70, Thr at position 74, Thr at position 76, Glu at position 82, Arg at position 87 and Tyr at position 95 were selected for HV.0, and Ile at position 2, Val at position 3, Thr at position 14, Pro at position 15, Gin at position 50, Leu at position 51 and Tyr at position 92 were selected for LV.0, and used for the modification of amino acids. By changing at least one or more of these selected amino acid residues to the amino acid residues found in the mouse antibody KM1334, the VH and VL of human CDR-grafted antibodies having various modifications were designed as follows.

Specifically, the amino acid sequence shown in SEQ ID NO:20, in which 6 residues of Lys at position 12, Lys at position 13, Ala at position 40, Pro at position 41, Met at position 48 and Tyr at position 95 were changed to Ala, Arg, Arg, Ser, Ile and Phe, respectively, found in the mouse antibody KM1334, was designed as the VH. The amino acid sequence shown in SEQ ID NO:21, in which 6 residues of Ile at position 2, Thr at position 14, Pro at position 15, Gin at position 50, Leu at position 51 and Tyr at position 92 were changed to Val, Ser, Leu, Lys, Val and Phe, respectively, found in the mouse antibody KM1334, was designed as the VL.

(2) Construction of cDNA Encoding VH of Anti-FGF-8 CDR-grafted Antibody

A cDNA encoding the anti-FGF-8 CDR-grafted antibody VH amino acid sequence HV.0 designed in the item 1(1) of Example 4 was constructed using PCR method in the following manner.

Firstly, the designed amino acid sequence was made into a full antibody amino acid sequence by ligating the secretory signal sequence of H chain of anti-FGF-8 mouse antibody KM1334 shown in SEQ ID NO:4. Next, the amino acid sequence was converted into genetic codons. When two or more genetic codons were present for one amino acid residue, corresponding genetic codon was determined by taking the codon usage found in nucleotide sequences of antibody genes into consideration [*Sequences of Proteins of Immunological Interest*, US Dept. Health and Human Services (1991)]. A nucleotide sequence of cDNA encoding the full antibody V region amino acid sequence was designed by ligating the thus determined genetic codons, and complementary nucleotide sequences of primers for use in the PCR amplification (including restriction enzyme recognition sequences for cloning into a humanized antibody expression vector) were added to the 5'-terminal and 3'-terminal. The thus designed nucleotide sequence was divided into sequences, each having 141 bases, from the 5'-terminal side, adjoining nucleotide sequences being designed such that the termini have an overlapping sequence of about 20 bases, and they were synthesized in alternating order of sense sequence and antisense sequence. Specifically, 4 synthetic oligonucleotides of SEQ ID NOs:22 to 25 were synthesized (manufactured by GENSET).

Each oligonucleotide was added to 50 μl of a reaction solution to give a final concentration of 0.1 μmol/l, and PCR was carried out by using 0.5 μmol/l M13 primer RV (manufactured by Takara Shuzo), 0.5 μmol/l [M13 primer M4 (manufactured by Takara Shuzo) and 2.5 units of KOD polymerase (manufactured by TOYOBO) according to the manufacture's instructions attached to the KOD polymerase. Regarding the reaction conditions, the reaction solution was carried out by heating at 94° C. for 5 minutes, subsequent 25 cycles of the reactions at 94° C. for 30 seconds, 50° C. for 30 seconds 74° C. for 60 seconds as one cycle, and further heating at 74° C. for 5 minutes. The reaction solution was precipitated with ethanol, and the precipitate was dissolved in sterile water and reaction was carried out by using 10 units of a restriction enzyme EcoRI (manufactured by Takara Shuzo) and 10 units of a restriction enzyme SpeI (manufactured by Takara Shuzo) at 37° C. for 1 hour. The reaction solution was fractionated by agarose gel electrophoresis to collect about 0.3 μg of an EcoRI-SpeI fragment of about 0.47 kb.

Next, 3 μg of a plasmid pBluescript II SK(–) (manufactured by Stratagene) was allowed to react with 10 units of restriction enzyme EcoRI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2.9 μg of an EcoRI-SpeI fragment of about 2.95 kb.

Figure 10:
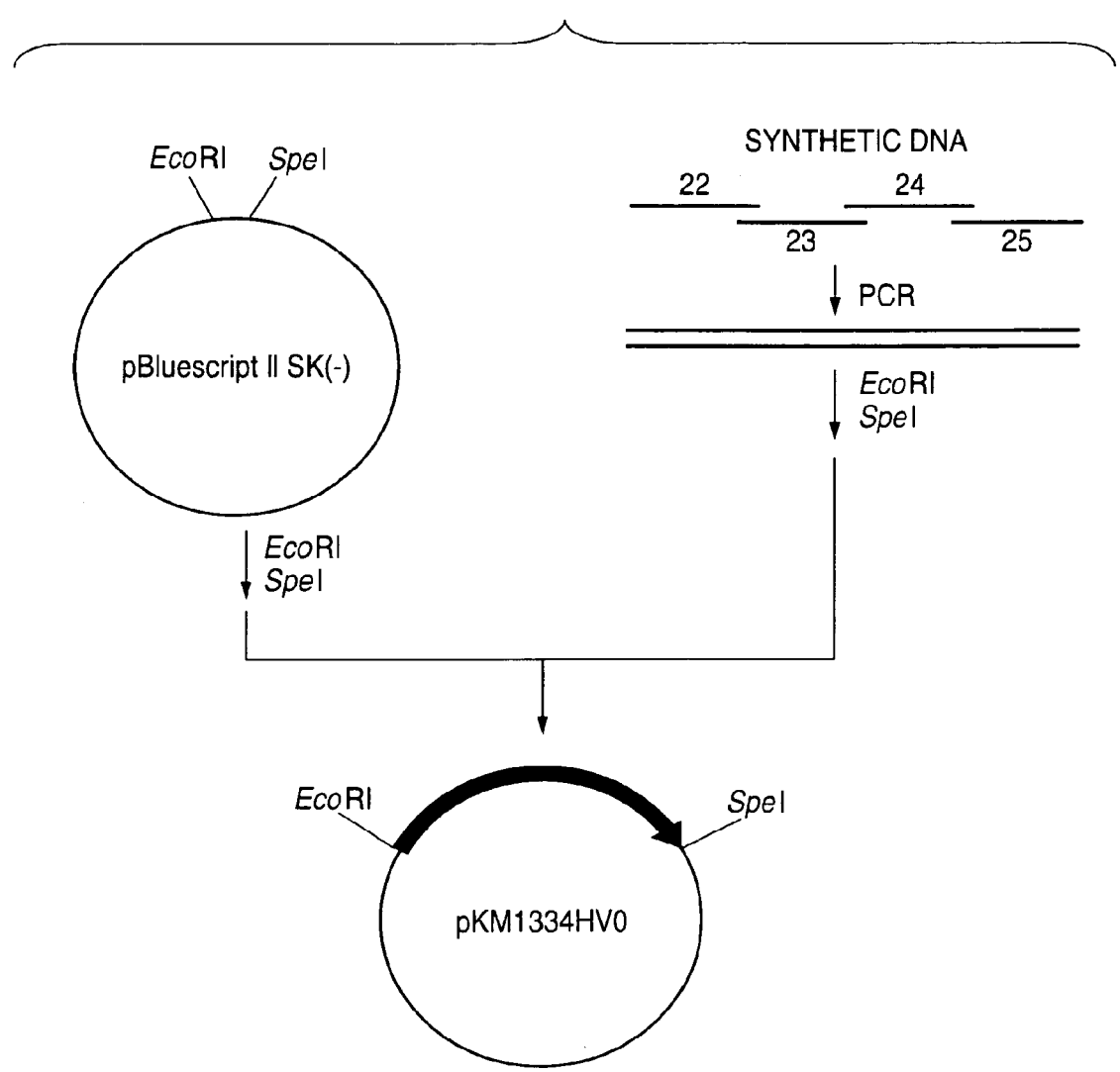
FIG. 10 shows construction steps of plasmid pKM1334HV0.

Next, 0.1 μg of the EcoRI-SpeI fragment of the PCR product of VH of the anti-FGF-8 CDR-grafted antibody and 0.1 μg of the EcoRI-SpeI fragment of the plasmid pBluescript II SK(–) both obtained in the above were added to 10 μl in total volume of sterile water and ligated using Ligation High (manufactured by TOYOBO). *E. coli* DH5α (manufactured by TOYOBO) was transformed by using the thus obtained recombinant plasmid DNA solution, each plasmid DNA was prepared from 10 clones of the transformants, and then nucleotide sequence analysis was carried out by the dideoxy method [*Molecular Cloning: A Laboratory Manual*, Cold Spring Harbor Lab. Press, New York (1989)] using Big Dye Terminator Kit ver. 2 (manufactured by Applied Biosystems). As a result of the nucleotide sequence analysis, a plasmid pKM1334HV0 shown in FIG. 10 having the nucleotide sequence of interest was obtained.

Also, a cDNA encoding the amino acid sequence HV.6 of VH of the anti-FGF-8 CDR-grafted antibody designed in the item 1(1) of Example 4 was constructed by PCR in the same manner as described above by using, as synthetic DNAs, 4 synthetic oligonucleotides of SEQ ED NOs:26 to 29 (manufactured by GENSET). As a result, a plasmid pKM1334HV6 containing HV.6-encoding cDNA was obtained.

(3) Construction of cDNA Encoding VL of Anti-FGF-8 CDR-grafted Antibody

A cDNA encoding the amino acid sequence LV.0 of VL of the anti-FGF-8 CDR-grafted antibody designed in the item 1(1) of Example 4 was constructed by PCR in the same manner as in the case of VH. In this case, however, the anti-FGF-8 mouse antibody KM1334 L chain sequence shown in SEQ ID NO:6 was used as the secretory signal sequence, and 4 synthetic oligonucleotides of SEQ ID NOs:30 to 33 (manufactured by GENSET) were used as synthetic DNAs. As a result, a plasmid pKM1334LV0 containing LV.0-encoding cDNA was obtained.

Also, a cDNA encoding the amino acid sequence LV.6 of VL of the anti-FGF-8 CDR-grafted antibody designed in the item 1(1) of Example 4 was constructed by PCR in the same manner as described above by using 4 synthetic oligonucleotides of SEQ ID NOs:34 to 37 (manufactured by GENSET) as synthetic DNAs. As a result, a plasmid pKM1334LV6 containing LV.6-encoding cDNA was obtained.

2. Construction of Anti-FGF-8 CDR-grafted Antibody Expression Vector

Using the pKANTEX93 for humanized antibody expression described in WO97/10354 and the plasmids pKM1334HV0 and pKM1334LV4 obtained in the items 1(2) and (3) of Example 4, an anti-FGF-8 CDR-grafted antibody expression vector pKANTEX1334HV0LV0 was constructed in the following manner.

A reaction was carried out by mixing 3 μg of the plasmid pKM1334HV0 obtained in the item 1(2) of Example 4 with 10 units of restriction enzyme ApaI (manufactured by Takara Shuzo) and 10 units of restriction enzyme NotI (manufactured by Takara Shuzo) at 37° C. for 1 hour. The reaction solution was fractionated by agarose gel electrophoresis to collect about 0.3 μg of an ApaI-NotI fragment of about 0.47 kb.

Next, 3 μg of the humanized antibody expression vector pKANTEX93 was allowed to react with 10 units of restriction enzyme ApaI (manufactured by Takara Shuzo) and 10 units of restriction enzyme NotI (manufactured by Takara Shuzo) at 37° C. for 1 hour. The reaction solution was fractionated by agarose gel electrophoresis to collect about 2 μg of an ApaI-NotI fragment of about 12.8 kb.

Figure 11:
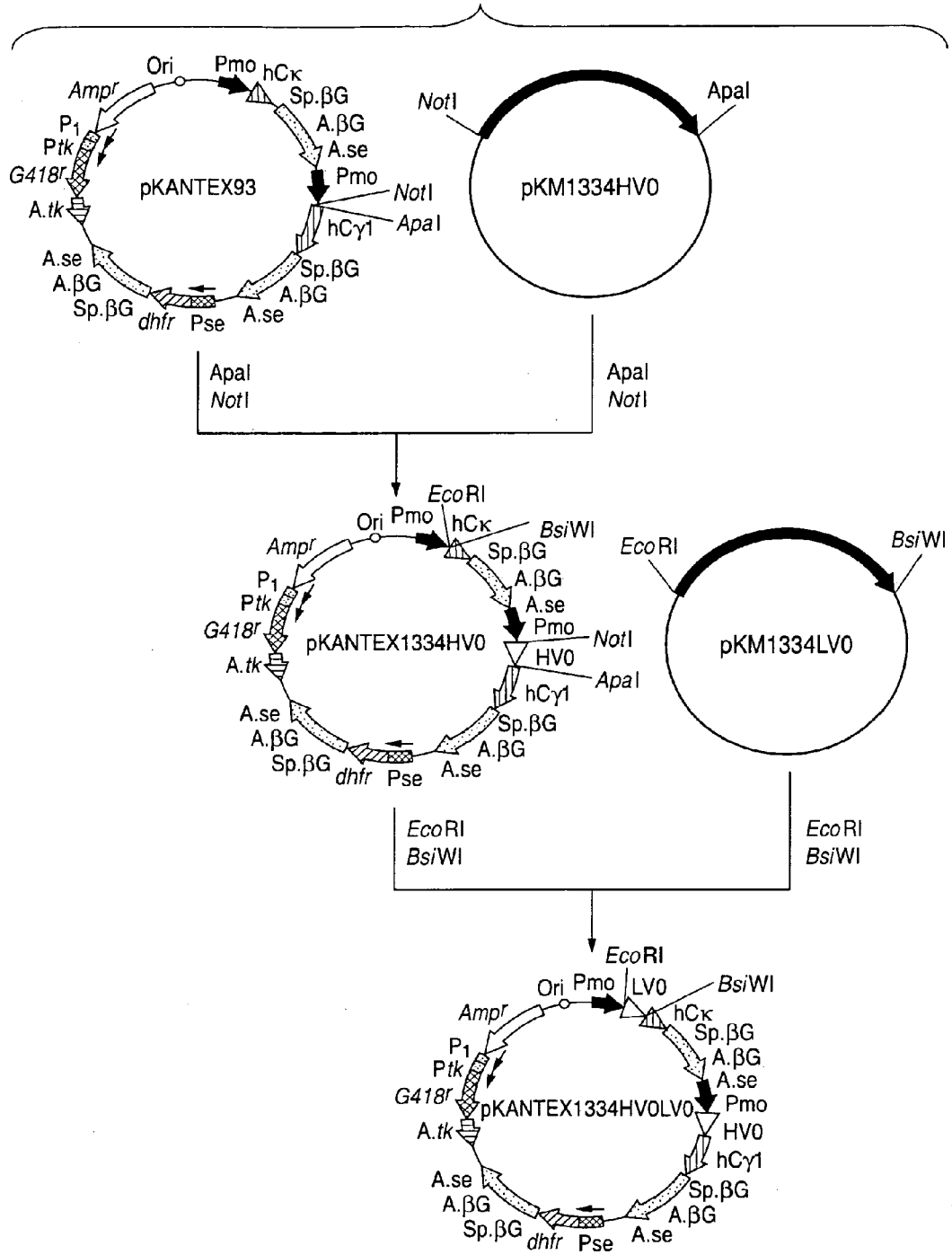
FIG. 11 shows construction steps of plasmid pKANTEX1334HV0LV0.

Next, 0.1 μg of the NotI-ApaI fragment derived from the plasmid pKM1334HV0 and 0.1 μg of the NotI-ApaI fragment derived from the plasmid pKANTEX93 were added to 10 μl in total volume of sterile water and ligated using Ligation High (manufactured by TOYOBO). Using the thus obtained recombinant plasmid DNA solution, *E. coli* DH5R was transformed to obtain a plasmid pKANTEX1334HV0 shown in FIG. 11.

Next, 3 μg of the plasmid pKM1334LV0 obtained in the item 1(3) of Example 4 was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 0.3 µg of an EcoRI-BsiWI fragment of about 0.45 kb.

Next, 3 µg of the plasmid pKANTEX1334HV0 obtained in the above was allowed to react with 10 units of restriction enzyme EcoRI (manufactured by Takara Shuzo) and 10 units of restriction enzyme BsiWI (manufactured by New England Biolabs) at 37° C. for 1 hour. The reaction solution was fractionated by agarose gel electrophoresis to collect about 2 µg of an EcoRI-BsiWI fragment of about 13.30 kb.

Next, 0.1 µg of the EcoRI-BsiWI fragment derived from the plasmid pKM1334LV0 and 0.1 µg of the EcoRI-BsiWI fragment derived from the plasmid pKANTEX334HV0 were added to 10 µl in total volume of sterile water and ligated by using Ligation High (manufactured by TOYOBO). Using the thus obtained recombinant plasmid DNA solution, the *E. coli* strain DH5a was transformed to obtain a plasmid pKANTEX1334HV0LV0 shown in FIG. 11.

Using 400 ng of the thus obtained plasmid, its nucleotide sequence was analyzed by the dideoxy method [*Molecular Cloning: A Laboratory Manual*, Cold Spring Harbor Lab. Press, New York (1989)] using Big Dye Terminator Kit ver. 2 (manufactured by Applied Biosystems) to thereby confirm that a plasmid into which the DNA of interest had been cloned was obtained.

Also, an expression vector pKANTEX1334HV0LV6 was constructed in the same manner as described above by using the plasmid pKM1334HV0 obtained in the item 1(2) of Example 4 and the plasmid pKANTEX1334LV6 obtained in the item 1(3) of Example 4.

In addition, an expression vector pKANTEX1334HV6LV6 was constructed by the same method described above using the plasmid pKM1334HV6 obtained in the item 1(2) of Example 4 and the plasmid pKANTEX1334LV6 obtained in the item 1(3) of Example 4.

3. Stable Expression of Anti-FGF-8 CDR-grafted Antibody Using YB2/0 Cell

Using the anti-FGF-8 CDR-grafted antibody expression vectors pKANTEX1334HV0 LV0, pKANTEX1334HV0LV6 and pKANTEX1334HV6LV6 obtained in the item 2 of Example 4, stable expression of various anti-FGF-8 CDR-grafted antibodies in YB2/0 cell was carried out in accordance with the method described in the item 2(5) of Example 1.

4. Purification of Anti-FGF-8 CDR-grafted Antibody

Culturing of transformants derived from YB2/0 cell expressing various anti-FGF-8 CDR-grafted antibodies obtained in the item 3 of Example 4 and purification of anti-FGF-8 CDR-grafted antibodies from culture supernatants were carried out according to the method described in the item 3(2) of Example 3. An antibody derived from a pKANTEX1334HV0LV0-introduced transformant was named HV0 LV0, an antibody derived from a pKANTEX1334HV0LV6-introduced transformant was named HV0LV6 and an antibody derived from a pKANTEX1334HV6LV6-introduced transformant was named HV6LV6.

5. Analysis of Purified Anti-FGF-8 CDR-grafted Antibodies

SDS-PAGE of various anti-FGF-8 CDR-grafted antibodies obtained in the item 4 of Example 4 was carried out in accordance with the method described in the item 4 of Example 3 As a result, it was confirmed that each antibody was expressed and purified as an antibody molecule of correct structure.

6. Measurement of Binding Activity of Anti-FGF-8 CDR-grafted Antibody Against FGF-8 (ELISA)

Figure 12:
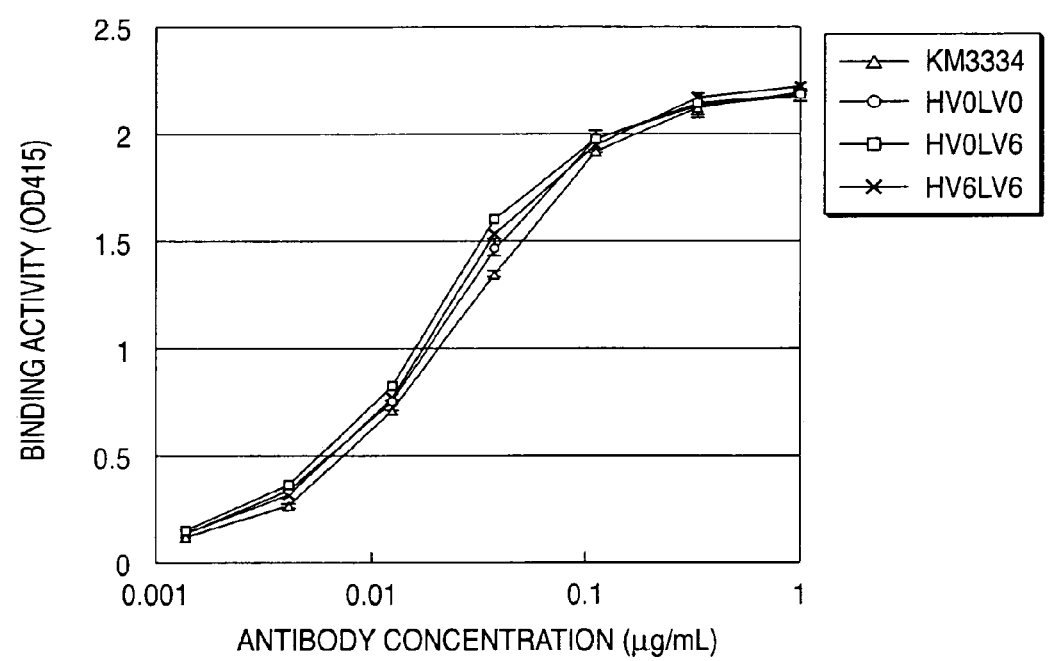
FIG. 12 shows results of the ELISA measurement of the FGF-8 binding activities of anti-FGF-8 chimeric antibody KM3334 and anti-FGF-8 CDR-grafted antibodies HV0LV0, HV0LV6 and HV6LV6. The abscissa and the ordinate show antibody concentration (µg/ml) and binding activity (OD415), respectively. "○", "□", "Δ" and "x" indicate activities of KM3334, HV0 LV0, HV0LV6 and HV6LV6, respectively.

The activity of various anti-FGF-8 CDR-grafted antibodies obtained in the item 4 of Example 4 to bind to FGF-8 was measured by the ELISA described in the item 2(6) of Example 3. The YB2/0-derived anti-FGF-8 chimeric antibody KM3334 obtained in the item 3(2) of Example 3 was used as a positive control. The results are shown in FIG. 12. As shown in FIG. 12, each of the anti-FGF-8 CDR-grafted antibodies showed an FGF-8 binding activity similar to that of KM3334, so that significant reduction of the binding activity caused by the CDR grafting was not observed.

7. Measurement of Binding Activity of Anti-FGF-8 CDR-grafted Antibodies for FGF-8

In order to examine the activity of various anti-FGF-8 CDR-grafted antibodies obtained in the item 4 of Example 4 to bind to FGF-S in more detail, activities of various anti-FGF-8 CDR-grafted antibodies to bind to FGF-8 were measured and compared as follows by using BIAcore 2000 (manufactured by BIACORE). The YB2/0-derived anti-FGF-8 chimeric antibody KM3334 obtained in the item 3(2) of Example 3 was used as a positive control.

Hereinafter, BBS-EP (manufactured by BIACORE) was used as the buffer for dilution of samples and during the measurement. First, a sensor tip CM-5 (manufactured by BIACORE) was set, and FGF-8 (manufactured by R&D) dissolved to give a concentration of 31.25 µg/ml by using 10 µmol/l acetate buffer (pH 4.0) was immobilized on the sensor tip surface by an amine coupling method. The immobilized amount was 4,498 RU.

Figure 13:
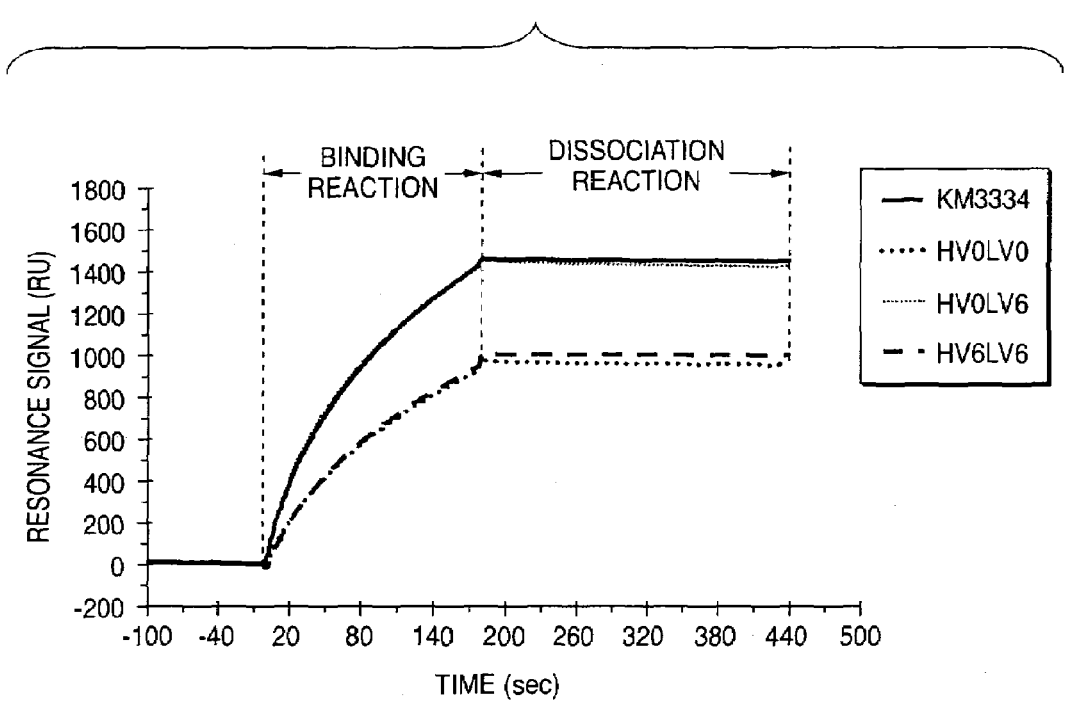
FIG. 13 shows results of the BIAcore 2000 measurement of the FGF-8 binding activities of anti-FGF-8 chimeric antibody KM3334 and anti-FGF-8 CDR-grafted antibodies HV0 LV0, HV0LV6 and HV6LV6. The abscissa and he ordinate show time (seconds) and resonance signal (RU), respectively.

To the FGF-8 immobilized flow cell, 60 µl of each antibody solution was added at a flow rate of 20 µl/minute, and then the dissociation reaction was monitored for 3 minutes. After the dissociation reaction, the tip surface was regenerated by adding 20 µl of 10 mmol/l Glycine-HCl buffer (pH 1.5) continuously twice to the flow cell. This cycle was carried out for antibody solutions of various concentrations (50 to 0.068 µg/ml), and a sensorgram at each concentration was obtained. The sensorgram of each antibody was made into a sensorgram of specific reaction by subtracting a sensorgram obtained using a chimeric antibody KM871 for GD3 [*Cancer Immunol. Immunother*, 36, 373 (1993)] as a negative control. The sensorgram of 50 µg/ml of each antibody is shown in FIG. 13. As is apparent from the sensorgram, dissociation was hardly observed at the time of the dissociation reaction of each antibody, so that it was difficult to obtain an accurate dissociation constant. Accordingly, comparison of the binding activity of various antibodies was carried out by comparing heights of binding [resonance signal (RU)] at the time of the binding reaction. As a result, as shown in FIG. 13, the chimeric antibody KM3334 showed the highest binding reaction, and the CDR-grafted antibody HV0LV6 showed a high binding reaction similar to that of KM3334. On the other hand, the CDR-grafted antibodies HV0LV0 and HV6LV6 showed a slightly lower binding reaction than KM3334 and HV0LV6. The above results show that comparison of binding activities between antibodies which could not be recognized by ELISA is possible by the use of BIAcore and that binding activity of CDR-grafted antibody is recovered to the same level of chimeric antibody by the modification of 6 amino acid residues of FR of VL. In addition, the effect on the increase of binding activity was not recognized on the 6 amino acid residues of FR of VH.

The YB2/0 cell-derived CDR-grafted antibody HV0LV6 which showed a high binding reaction similar to that of the chimeric antibody KM3334 was named KM8037, and the YB2/0 cell-derived transformed cell line highly expressing KM8037 was also named KM8037. Also, the transformed cell line KM8037 has been deposited on Jun. 20, 2002, as FERM BP-8084 in International Patent Organism Depositary, National Institute of Advanced Industrial Science and Technology (AIST Tsukuba Central 6, 1-1, Higashi 1-Chome Tsukuba-shi, Ibaraki-ken 305–8566 Japan).

EXAMPLE 5

Preparation of Anti-FGF-8 CDR-grafted Antibody Having Lower Immunogenicity (I)

It was revealed from the results of Example 4 that the anti-FGF-8 CDR-grafted antibody having modification of 6 amino acid residues derived from the mouse antibody KM1334, in FR of VL, shows a binding activity similar to that of the corresponding chimeric antibody. Accordingly, the effect of these 6 residues on the recovery of the activity was further examined, and anti-FGF-8 CDR-grafted antibodies which have sufficient activity and contain smaller number of mouse antibody-derived amino acid residues and are expected to have more reduced immunogenicity were prepared as follows 1. Design of Amino Acid Sequence of VL Regarding the above 6 amino acid residues, amino acid sequences of 6 VLs having the following modifications were designed.

In LV.4-1, 4 residues of Ile at position 2, Gln at position 50, Leu at position 51 and Tyr at position 92 were changed to Val, Lys, Val and Phe, respectively, which are amino acid residues found in the mouse antibody KM1334.

In LV.4-2, 4 residues of Ile at position 2, Thr at position 14, Pro at position 15 and Tyr at position 92 were changed to Val, Ser, Leu and Phe, respectively, which are amino acid residues found in the mouse antibody KM1334.

In LV.3-1, 3 residues of Ile at position 2, Leu at position 51 and Tyr at position 92 were changed to Val, Val and Phe, respectively, which are amino acid residues found in the mouse antibody KM1334.

In LV.3-2, 3 residues of Thr at position 14, Pro at position 15 and Tyr at position 92 were changed to Ser, Leu and Phe, respectively, which are amino acid residues found in the mouse antibody KM1334.

In LV.2-1, 2 residues of Leu at position 51 and Tyr at position 92 were changed to Val and Phe, respectively, which are amino acid residues found in the mouse antibody KM1334.

In LV.2-2, 2 residues of Ile at position 2 and Tyr at position 92 were respectively changed to Val and Phe, respectively, which are amino acid residues found in the mouse antibody KM1334.

2. Construction of cDNA Encoding VL

The cDNAs encoding respective anti-FGF-8 CDR-grafted antibody VL amino acid sequences designed in the item 1 of Example 5 were constructed as follows.

(1) Construction of cDNA Encoding LV.4-1

The cDNA encoding LV.4-1 was constructed in accordance with the method described in the item 1(3) of Example 4, using four synthetic oligonucleotides of SEQ ID NOs:31, 34, 36 and 37 as synthetic DNA fragments (manufactured by GENSET). As a result, a plasmid pKM1334LV4-1 containing a cDNA encoding LV.4-1 was obtained.

(2) Construction of cDNA Encoding LV.3-1

Using 50 ng of the plasmid pKM1334LV6 obtained in the item 1(3) of Example 4 as the template, M13 primer RV (manufactured by Takara Shuzo) and the synthetic DNA having the nucleotide sequence describe in SEQ ID NO:38 (manufactured by GENSET) were added as primers to give a final concentration of 0.3 μmol/Lol/L, PCR was carried out according to the manufacture's instructions attached to KOD polymerase (manufactured by TOYOBO) by first heating at 94° C. for 2 minutes and subsequent 35 cycles of reactions at 94° C. for 15 seconds, 50° C. for 30 seconds and 68° C. for 1 minute one cycle. The reaction solution was purified, the product was dissolved in sterile water, and a reaction was carried out by adding 10 units of a restriction enzyme KpnI (manufactured by Takara Shuzo) and 10 units of a restriction enzyme SpeI (manufactured by Takara Shuzo) thereto at 37° C. for 1 hour. The reaction solution was fractionated by agarose gel electrophoresis to collect about 0.3 μg of a KpnI-SpeI fragment of about 0.22 kb.

Next, 3 μg of the plasmid pKM1334LV4-1 obtained in the item 2(1) of Example 5 was allowed to react with 10 units of restriction enzyme KpnI (manufactured by Takara Shuzo) at 37° C. for 1 hour. The reaction solution was fractionated by agarose gel electrophoresis to collect about 0.2 μg of a KpnI-KpnI fragment of about 0.21 kb.

Next, 3 μg of the plasmid pBluescript II SK(−) was allowed to react 10 units of restriction enzyme KpnI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2 μg of a KpnI-SpeI fragment of about 2.95 kb.

Figure 14:
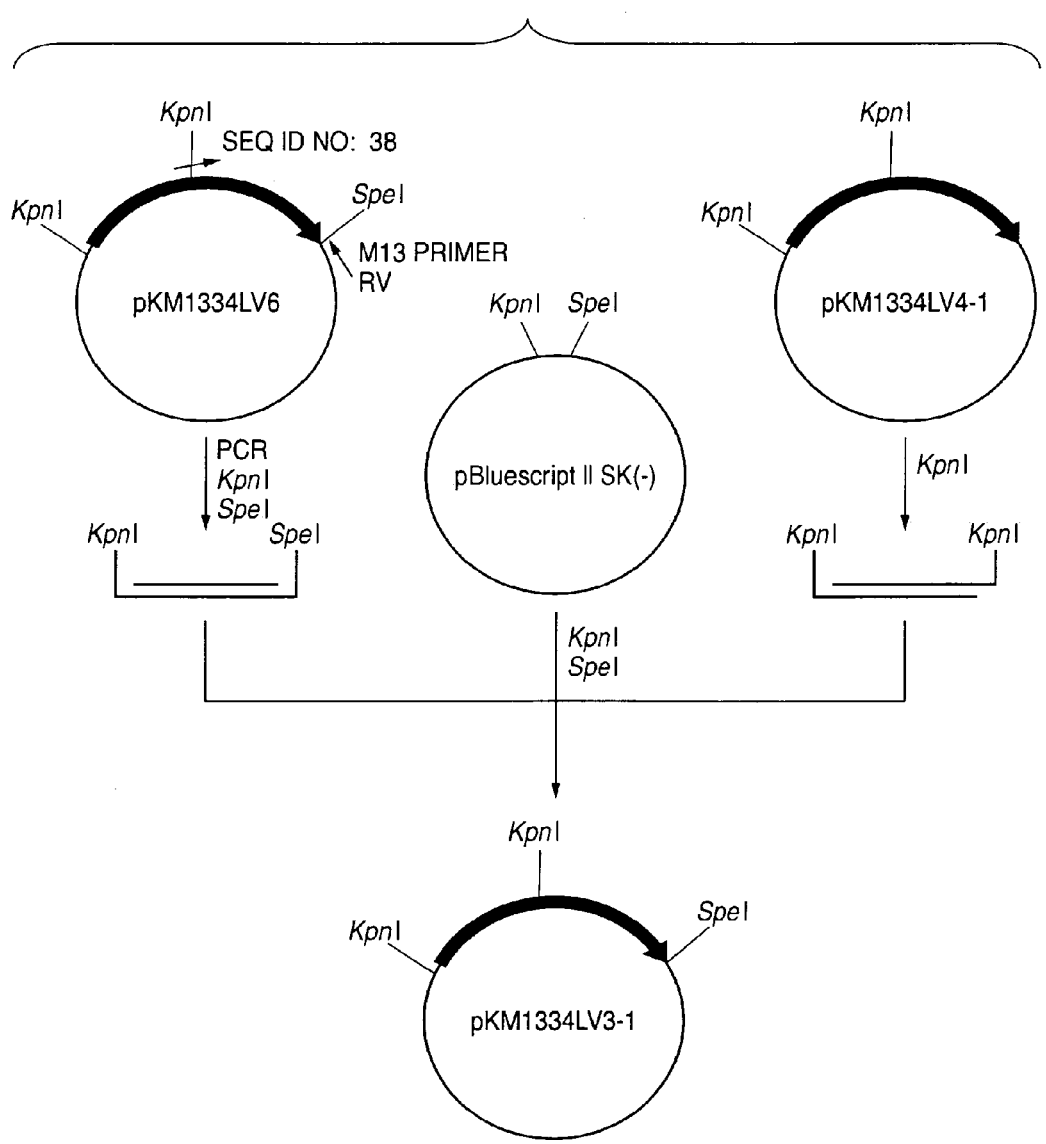
FIG. 14 shows construction steps of plasmid pKM1334LV3-1.

To 10 μl in total volume of sterile water, 0.1 μg of the KpnI-SpeI fragment of the VL cDNA, 0.1 μg of the KpnI-KpnI fragment derived from the plasmid pKM1334LV4-1 and 0.1 μg of the KpnI-SpeI fragment of the plasmid pBluescript II SK(−) each obtained in the above were added and ligated by using Ligation High (manufactured by TOYOBO). E. coli DH5α was transformed by using the thus obtained recombinant plasmid DNA solution to obtain a plasmid pKM1334LV3-1 shown in FIG. 14 containing a cDNA encoding the LV.3-1.

(3) Construction of cDNA Encoding LV.2-1

A plasmid pKM1334LV2-1 containing a cDNA encoding the LV.2-1 was obtained by a method similar to that described in the item 2(1) of Example 5, except that the plasmid pKM1334LV0 obtained in the item 1(3) of Example 4 was used instead of the plasmid pKM1334LV4-1.

(4) Construction of cDNA Encoding LV.2-2

A plasmid pKM1334LV2-2 containing a cDNA encoding the LV.2-2 was obtained by a method similar to that described in the item 2(1) of Example 5, except that the synthetic DNA shown in SEQ ID NO:38 was used instead of the synthetic DNA shown in SEQ ID NO:39 as a primer.

(5) Construction of cDNA Encoding LV.4-2

A reaction was carried out by mixing 3 μg of the plasmid pKM1334LV2-2 obtained in the item 2(4) of Example 5 with 10 units of restriction enzyme KpnI (manufactured by Takara Shuzo) at 37° C. for 1 hour. The reaction solution was fractionated by agarose gel electrophoresis to collect about 2 μg of a KpnI-KpnI fragment of about 3.16 kb.

Next, 3 μg of the plasmid pKM1334LV6 obtained in the item 1(3) of Example 4 was allowed to react with 10 units of restriction enzyme KpnI (manufactured by Takara Shuzo) at 37° C. for 1 hour. The reaction solution was fractionated by agarose gel electrophoresis to collect about 0.2 µg of a KpnI-KpnI fragment of about 0.21 kb.

Figure 15:
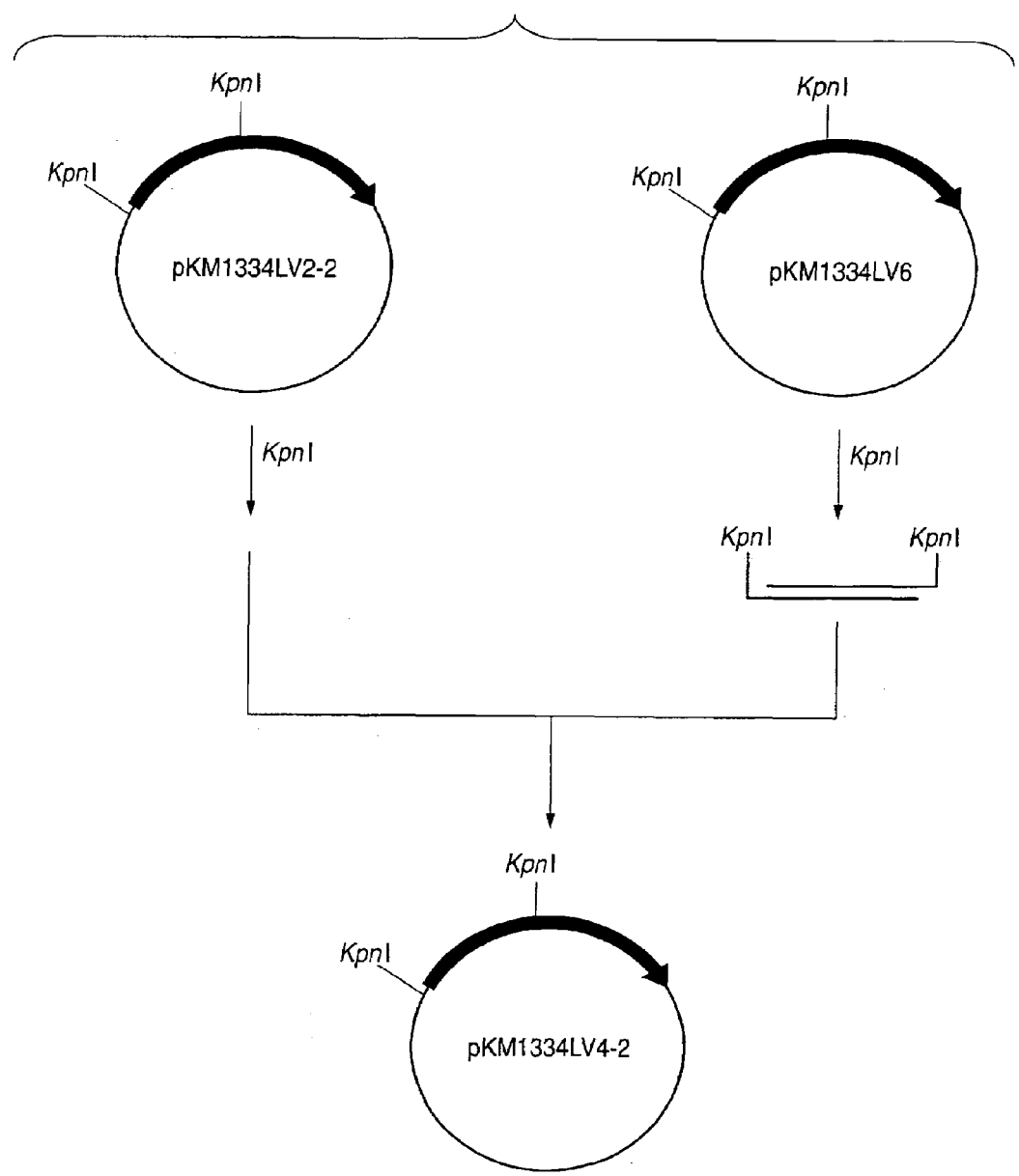
FIG. 15 shows construction steps of plasmid pKM1334LV4-2.

To 10 µl in total volume of sterile water, 0.1 µg of the KpnI-KpnI fragment derived from the plasmid pKM1334LV2-2 and 0.1 µg of the KpnI-KpnI fragment derived from the plasmid pKM1334LV6 each obtained in the above were added and ligated by using Ligation High (manufactured by TOYOBO). *E. coli* DH5a was transformed by using the thus obtained recombinant plasmid DNA solution to obtain the plasmid pKM1334LV4-2 shown in FIG. 15 containing a cDNA encoding the LV.4-2.

(6) Construction of cDNA Encoding LV.3-2

A reaction was carried out by mixing 3 µg of the plasmid pKM1334LV4-2 obtained in the item 2(5) of Example 5 with 10 units of restriction enzymes Tth111I (manufactured by Takara Shuzo) and XmnI (manufactured by New England Biolabs) at 37° C. for 1 hour. The reaction solution was fractionated by agarose gel electrophoresis to collect about 2 µg of a Tth111]-XmnI fragment of about 2.24 kb.

Next, 3 µg of the plasmid pKM1334LV0 obtained in the item 1(3) of Example 4 was allowed to react with 10 units of restriction enzymes Tth111I (manufactured by Takara Shuzo) and XmnI (manufactured by New England Biolabs) at 37° C. for 1 hour. The reaction solution was fractionated by agarose gel electrophoresis to collect about 1 µg of a Tth111I-XmnI fragment of about 1.11 kb.

Figure 16:
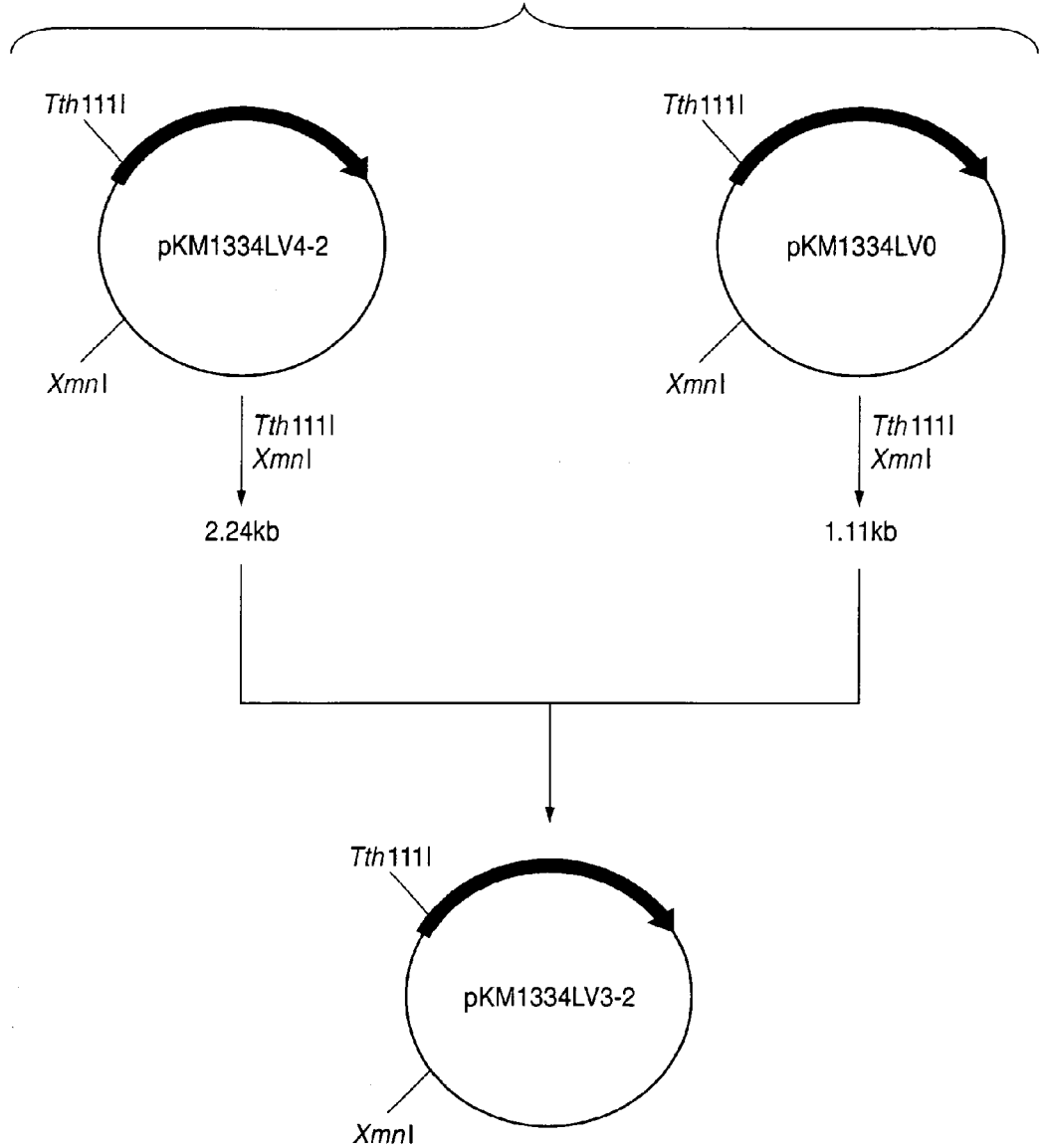
FIG. 16 shows construction steps of plasmid pKM1334LV3-2.

To 10 µl in total volume of sterile water, 0.1 µg of the Tth111I-XmnI fragment derived from the plasmid pKM1334LV42 and 0.1 µg of the Tth111I-XmnI fragment derived from the plasmid pKM1334LV0 each obtained in the above were added and ligated by using Ligation High (manufactured by TOYOBO). *E. coli* DH5a was transformed by using the thus obtained recombinant plasmid DNA solution to obtain a plasmid pKM1334LV3-2 shown in FIG. 16 containing a cDNA encoding the LV.3-2.

3. Construction of Anti-FGF-8 CDR-grafted Antibody Expression Vector

Various VL cDNA-containing anti-FGF-8 CDR-grafted antibody expression vectors were constructed by replacing the EcoRI-BsiWI fragment containing the VL cDNA of the expression vector pKANTEX1334HV0LV0 obtained in the item 2 of Example 4 by each of the various VL cDNA-containing EcoRI-BsiWI fragments constructed in the item 2 of Example 5. Specifically, 6 vectors pKANTEX1334HV0LV4-1, pKANTEX1334HV0LV4-2, pKANTEX1334HV0LV3-1, pKANTEX1334HV0LV3-2, pKANTEX1334HV0LV2-1 and pKANTEX1334HV0LV2-2 were constructed.

4. Stable Expression of Anti-FGF-8 CDR-grafted Antibody Using CHO/DG44 Cell

Stable expression of various anti-FGF-8 CDR-grafted antibodies in CHO/DG44 cell was carried out in accordance with the method described in the item 2(4) of Example 3, using the anti-FGF-8 CDR-grafted antibody expression vectors pKANTEX1334HV0LV0 and pKANTEX1334HV0LV6 obtained in the item 2 of Example 4 and the various anti-FGE-8 CDR-grafted antibody expression vectors obtained in the item 3 of Example 5.

5. Purification of Anti-FGF-8 CDR-grafted Antibody

Culturing of CHO/DG44 cell-derived transformants expressing various anti-FGF-8 CDR-grafted antibodies obtained in the item 4 of Example 5 and purification of the anti-FGF-8 CDR-grafted antibodies from culture supernatants were carried out in accordance with the method described in the item 3(1) of Example 3. An antibody derived from a pKANTEX1334HV0LV0-introduced transformant was named HV0LV0/CHO, an antibody derived from a pKANTEX1334HV0LV6-introduced transformant was named HV0LV6/CHO, an antibody derived from a pKANTEX1334HV0LV4-1-introduced transformant was named HV0LV4-1/CHO, an antibody derived from a pKANTEX1334HV0LV4-2-introduced transformant was named HV0LV4-2/CHO, an antibody derived from a pKANTEX1334HV0LV3-1-introduced transformant was named HV0LV3-l/CHO, an antibody derived from a pKANTEX1334HV0LV3-2-introduced transformant was named HV0LV0/CH3-2, an antibody derived from a pKANTEX1334HV0LV2-1-introduced transformant was named HV0LV201/CHO and an antibody derived from a pKANTEX1334HV0LV2-2-introduced transformant was named HV0LV2-2/CHO.

6. Analysis of Purified Anti-FGF-8 CDR-grafted Antibody

SDS-PAGE of various anti-FGF-8 CDR-grafted antibodies obtained in the item 5 of Example 5 was carried out in accordance with the method described in the item 4 of Example 3. As a result, it was confirmed that each antibody was expressed and purified as an antibody molecule of correct structure.

7. Measurement of Binding Activity of Anti-FGF-8 CDR-grafted Antibody Against FGF-8 (BIAcore biosensor)

In order to examine the activity of various anti-FGF-8 CDR-grafted antibodies obtained in the item 5 of Example 5 to bind to FGF-8 in more detail, activities of various anti-FGF-8 CDR-grafted antibodies to bind to FGF-8 were measured and compared as follows by using BIAcore 2000 (manufactured by BIACORE). The CHO/DG44-derived anti-FGF-8 chimeric antibody KM3034 obtained in the item 3(1) of Example 3 was used as a positive control.

Hereinbelow, HBS-EP (manufactured by Pharmacia) was used as the buffer solution for dilution of samples and during the measurement. First, a sensor tip SA (manufactured by BIACORE) was set, and 5 µl of a C-terminus-biotin labeled compound 1 (an N-terminus peptide of FGF-8; SEQ ID NO:17) prepared to a solution of 0.05 µg/ml was added thereto at a flow rate of 20 µg/minute. Thereafter, the tip surface was washed by adding 5 µl of 10 mmol/l Glycine-HCl buffer (pH 1.5) continuously twice. Immobilized amount of the FGF-8 peptide was 35 RU.

To the FGF-8 peptide immobilized flow cell, 60 µl of each antibody solution was added at a flow rate of 20 µl/minute, and then the dissociation reaction was monitored for 3 minutes. After the dissociation reaction, the tip surface was regenerated by adding 20 µl of 10 mmol/l Glycine-HCl buffer (pH 1.5) continuously twice. This cycle was carried out for antibody solutions of various concentrations (50 to 1.85 µg/ml), and a sensorgram at each concentration was obtained. The sensorgram of each antibody was made into a sensorgram of specific reaction by subtracting a sensorgram obtained using a chimeric antibody KM871 for GD3 *[Cancer Immunol. Immunother.,* 36, 373 (1993)] as a negative control.

Figure 17:
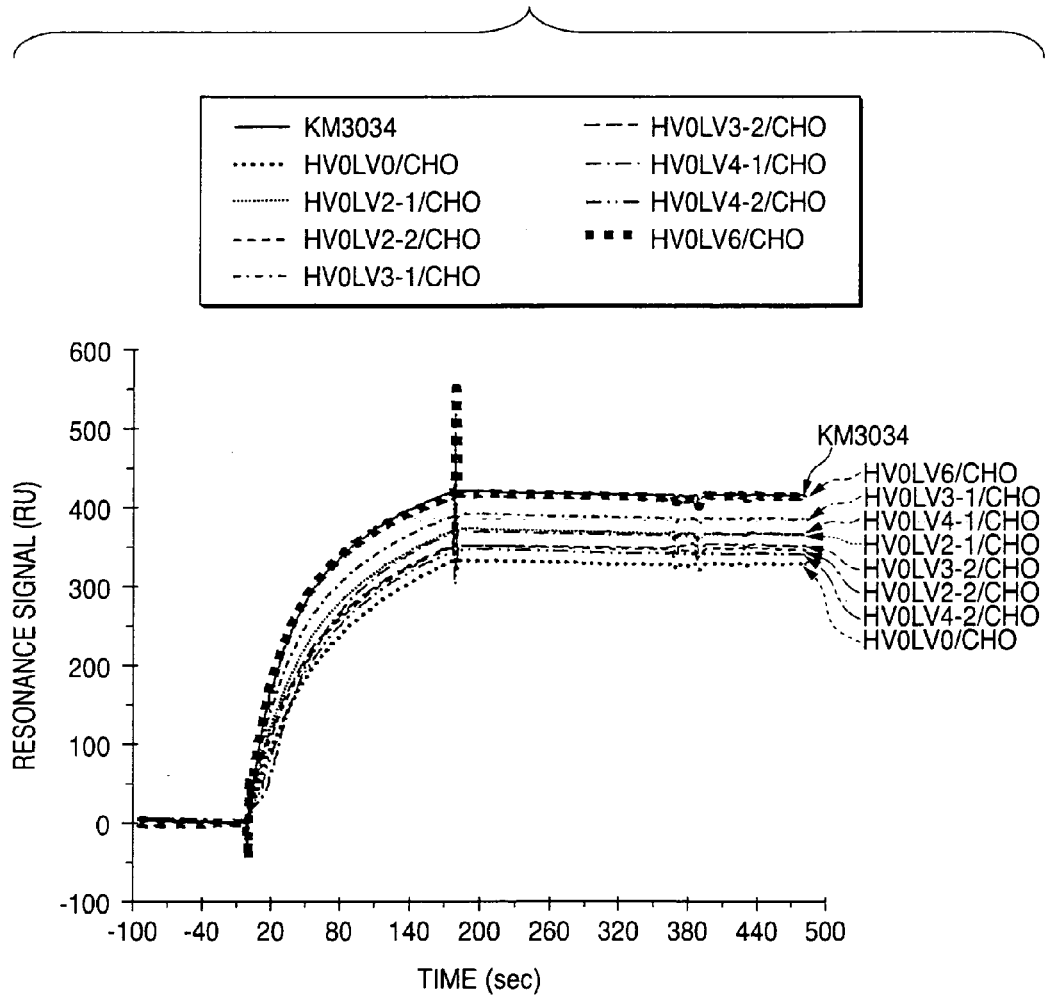
FIG. 17 shows results of BIAcore 2000 measurement of FGF-8 binding activities of anti-FGF-8 chimeric antibody KM3034 and anti-FGF-8 CDR-grafted antibodies HV0LV0/CHO, HV0LV2-1/CHO, HV0LV2-2/CHO, HV0LV3-1/CHO, HV0LV3-2/CHO, HV0LV4-1/CHO, HV0LV4-2/CHO and HV0LV6/CHO. The abscissa and the ordinate show time (seconds) and resonance signal (RU), respectively.

The sensorgram of 16.7 µg/ml of each antibody is shown in FIG. 17. As is apparent from the sensorgram, dissociation was hardly observed at the time of the dissociation reaction of each antibody, so that it was difficult to obtain accurate dissociation constant. Accordingly, the binding activity of various antibodies was carried out by comparing intensity of binding [resonance signal (RU)] at the time of the binding reaction.

As a result, as shown in FIG. 17, the chimeric antibodies KM3034 and HV0LV6/CHO showed the highest binding reaction, followed by HV0LV3-1/CHO, HV0LV4-1/CHO and HV0LV2-1/CHO in this order. On the other hand, HV0LV32/CHO, HV0LV2-2/CHO and HV0LV4-2/CHO showed low binding reaction, and HV0LV0/CHO showed the lowest binding reaction. These results coincided with the results using the YB2/0 cell-derived anti-FGF-8 CDR-grafted antibodies described in the item 7 of Example 4.

8. Measurement of Neutralization Activity of Anti-FGF-8 CDR-grafted Antibodies for FGF-8

Figure 18:
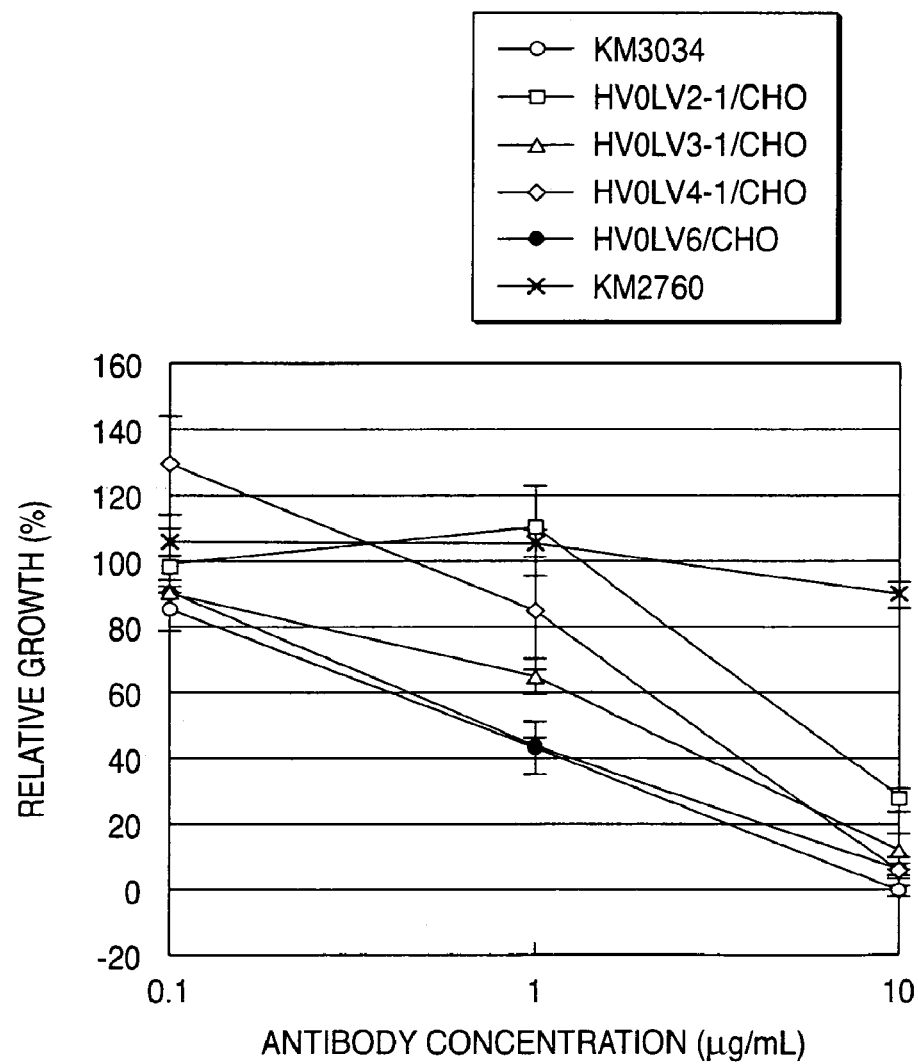
FIG. 18 shows neutralization activities of anti-FGF-8 chimeric antibody KM3034 and anti-FGF-8 CDR-grafted antibodies HV0LV2-1/CHO, HV0LV3-1/CHO, HV0LV4-1/CHO and HV0LV6/CHO on the FGF-8-dependent growth of mouse breast cancer cell line SC-3 cells. The abscissa and the ordinate show antibody concentration (µg/ml) and relative growth (%) when the growth by the addition of FGF-8 alone is defined as 100%, respectively. "○", "□", "Δ", "◇", "●" and "x" indicate activities of KM3034, HV0LV2-1/CHO, HV0LV3-1/CHO, HV0LV4-1/CHO, HV0LV6/CHO and KM2760 as a negative control, respectively.

Evaluation of neutralization activity of the four anti-FGF-8 CDR-grafted antibodies HV0LV6/CHO, HV0LV3-1/CHO, HV0LV4-1/CHO and HV0LV2-1/CHO whose high binding reaction for FGF-8 was confirmed in the item 7 of Example 5 was carried out in accordance with the method described in the item 5 of Example 4. The CHO/DG44 cell-derived anti-FGF-8 chimene antibody KM3034 obtained in the item 3(1) of Example 3 was used as a positive control, and the chimeric antibody KM2760 for human chemokine CCR4 described in WO 01/64754 as a negative control. The results are shown in FIG. 18. As shown in FIG. 18, the HV0LV6/CHO showed similar FGF-8 neutralization activity to that of the chimeric antibody KM3034, and the HV0LV3-1/CHO showed the next high FGF-8 neutralization activity. The HV0LV4-1/CHO showed a slightly lower FGF-8 neutralization activity than the HV0LV3-1/CHO, and the HV0LV2I/CHO showed the lowest neutralization activity.

EXAMPLE 6

Preparation of Anti-FGF-8 CDR-grafted Antibody Having Lower Immunogenicity (2)

It was found from the results of Example 5 that among modifications of the 6 amino acid residues of LV6, modification at position 51 is essential for the activity recovery. Also, it was suggested that modification at position 2 has small effect for the activity recovery by its modification alone, but it contributes to the activity recovery cooperatively by its combination with the 51st position modification. Regarding the modifications at positions 14 and 15, it was suggested also that they contribute to the activity recovery cooperatively by their combination with the modification at position 51. On the other hand, it was suggested that effect of the modification of the 50th position is small. Accordingly, in order to examine which one of the modification at position 2 and the modification at position 14 or 15 has higher effect on the activity recovery, and for examining effect of the modification at position 92, preparation of anti-FGF-8 CDR-grafted antibodies was carried out again.

1. Re-designing of VL Amino Acid Sequences

Amino acid sequences of two VLs having the following modifications were designed. Each case shows modification from amino acid residues of LV.0.

In LV.4-3, 4 residues of Thr at position 14, Pro at position 15, Leu at position 51 and Tyr at position 92 were changed to Ser, Leu, Val and Phe, respectively, which are amino acid residues found in the mouse antibody KM1334.

In LV.3-3, 3 residues of Thr at position 14, Pro at position 15 and Leu at position 51 were changed to Ser, Leu and Val, respectively, which are amino acid residues found in the mouse antibody KM1334.

2. Construction of cDNA Encoding VL

The cDNAs encoding respective anti-FGF-8 CDR-grafted antibody VL amino acid sequences designed in the item 1 of Example 6 were constructed as follows.

(1) Construction of cDNA Encoding LV.4-3

This was constructed in accordance with the method described in the item 2(5) of Example S. However, the plasmid pKM1334LV2-1 obtained in the item 2(3) of Example 5 was used instead of the plasmid pKM1334LV2-2 and the plasmid pKM1334LV3-2 obtained in the item 2(6) of Example 3 was used instead of the plasmid pKM1334LV6. As a result, a plasmid pKM1334LV4-3 containing a cDNA encoding LV.4-3 was obtained.

(2) Construction of cDNA Encoding LV.3-3

A reaction was carried out by mixing 3 µg of the plasmid pKM1334LV4-3 obtained in the item 2(1) of Example 6 with 10 units of restriction enzyme BamHI (manufactured by Takara Shuzo) and 10 units of restriction enzyme SpeI (manufactured by Takara Shuzo) at 37° C. for 1 hour. The reaction solution was fractionated by agarose gel electrophoresis to collect about 2.5 µg of a BamHI-SpeI fragment of about 3.23 kb.

Next, 3 µg of the plasmid pKM1334LV0 obtained in the item 1(3) of Example 4 was allowed to react with 10 units of restriction enzyme BamHI (manufactured by Takara Shuzo) and 10 units of restriction enzyme SpeI (manufactured by Takara Shuzo) at 37° C. for 1 hour. The reaction solution was fractionated by agarose gel electrophoresis to collect about 0.15 µg of a BamHI-SpeI fragment of about 0.13 kb.

Figure 19:
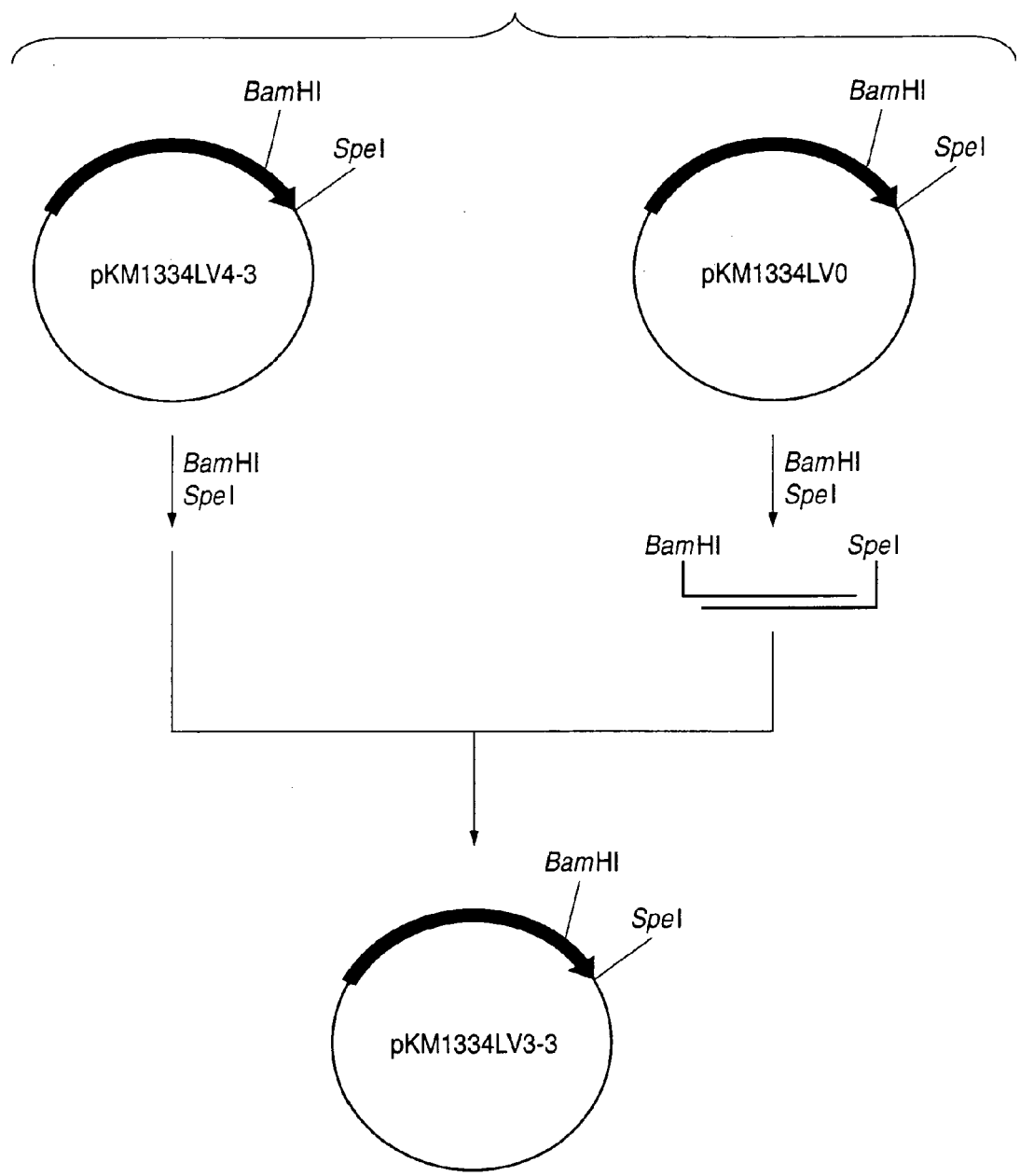
FIG. 19 shows construction steps of plasmid pKM1334LV3-3.

To 10 µl in total volume of sterile water, 0.1 µg of the BamHI-SpeI fragment derived from the plasmid pKM1334LV4-3 and 0.1 µg of the BamHI-SpeI fragment derived from the plasmid pKM1334LV0 each obtained in the above were added and ligated by using Ligation High (manufactured by TOYOBO). E. coli DH5a was transformed by using the thus obtained recombinant plasmid DNA solution to obtain the plasmid pKM1334LV3-3 shown in FIG. 19 containing a cDNA encoding the LV.3-3.

3. Construction of Anti-FGF-8 CDR-grafted Antibody Expression Vectors

Anti-FGF-8 CDR-grafted antibody expression vectors having various VL cDNAs were constructed by replacing the EcoRI-BsiWI fragment containing the VL cDNA of the expression vector pKANTEX1334HV0LV6 obtained in the item 2 of Example 4 by the EcoRI-BsiWI fragments containing various VL cDNAs constructed in the item 2 of Example 6. Specifically, 2 vectors pKANTEX)334HV0LV4-3 and pKANTEX1334HV0LV3-3 were constructed.

4. Stable Expression of Anti-FGF-8 CDR-grafted Antibody Using CHO/DG44 Cell

Stable expression of various anti-FGF-8 CDR-grafted antibodies in CHO/DG44 cell was carried out in accordance with the method described in the item 2(4) of Example 3 by using various anti-FGF-8 CDR-grafted antibody expression vectors obtained in the item 3 of Example 6.

5. Purification of Anti-FGF-8 CDR-grafted Antibody

Culturing of CHO/DG44 cell-derived transformants expressing various anti-FGF-8 CDR-grafted antibodies obtained in the item 4 of Example 6 and purification of the anti-FGF-8 CDR-grafted antibodies from culture supernatants were carried out in accordance with the method described in the item 3(1) of Example 3. An antibody derived from a pKANTEX1334HV0LV4-3-introduced transformant was named HV0LV431CHO, and an antibody derived from a pKANTEX1334HV0LV3-3-introduced transformant was named HV0LV3-3/CHO.

6. Analysis of Purified Anti-FGF-8 CDR-grafted Antibody

SDS-PAGE of various anti-FGF-8 CDR-grafted antibodies obtained in the item 5 of Example 6 was carried out according to the method described in the item 4 of Example 3. As a result, it was confirmed that each antibody was expressed and purified as an antibody molecule of correct structure.

7. Measurement of Binding Activity of Anti-FGF-8 CDR-grafted Antibodies for FGF-8

The FGF-8 binding activities of the anti-FGF-8 CDR-grafted antibodies HV0LV6/CHO and HV0LV3-1/CHO obtained in the item 5 of Example 5 and the anti-FGF-8 CDR-grafted antibodies HV0LV4-3/CHO and HV0LV3-3/CHO obtained in the item 5 of Example 6 were measured in accordance with the method described in the item 7 of Example 5. The CHO/DG44-derived anti-FGF-8 chimeric antibody KM3034 obtained in the item 3(1) of Example 3 was used as a positive control.

Figure 20:
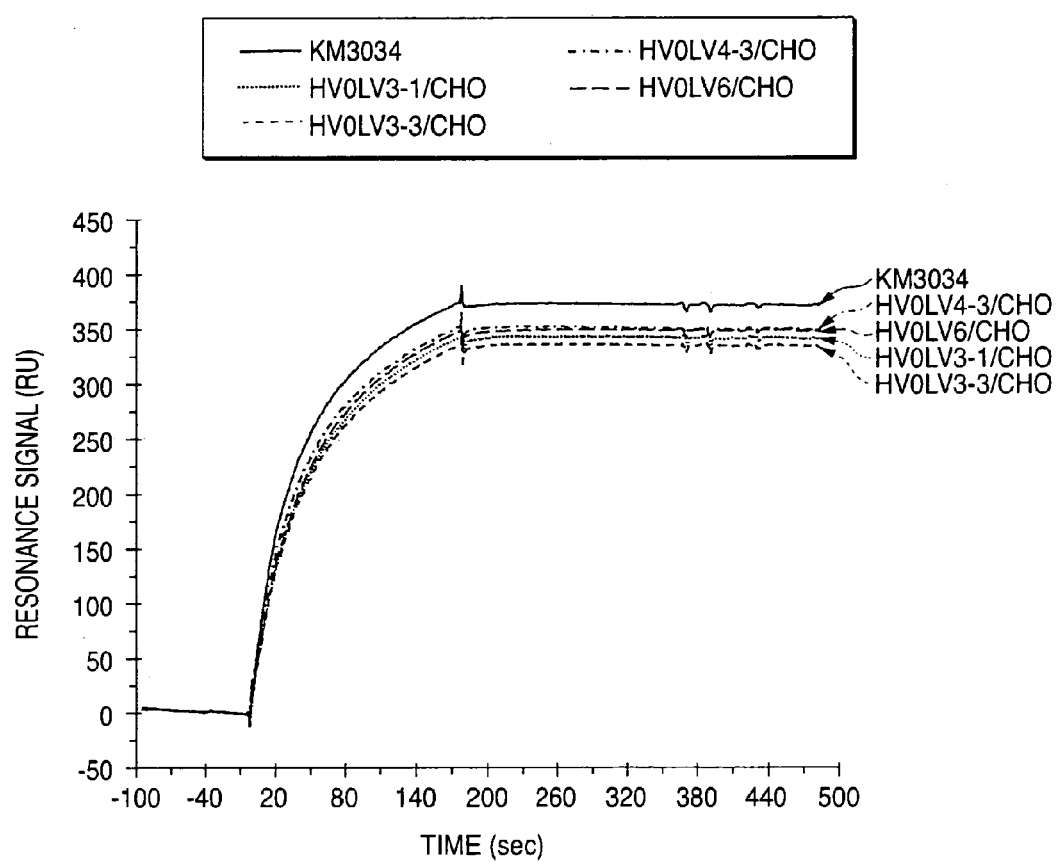
FIG. 20 shows results of BIAcore 2000 measurement of FGF-8 binding activities of anti-FGF-8 chimeric antibody KM3034 and anti-FGF-8 CDR-grafted antibodies HV0LV3-1/CHO, HV0LV3-3/CHO, HV0LV4-3/CHO and HV0LV6/CHO. The abscissa and the ordinate show time (seconds) and resonance signal (RU), respectively.

The sensorgram of 16.7 µg/ml of each antibody is shown in FIG. 20. As is apparent from the sensorgram, dissociation was hardly observed at the time of the dissociation reaction of each antibody, so that it was difficult to obtain accurate dissociation constant. Accordingly, the binding activity of respective antibodies was carried out by comparing intensity of binding [resonance signal (RU)] at the time of the binding reaction. As a result, as shown in FIG. 20, the chimeric antibodies KM3034 showed the highest binding reaction, and HV0LV4-3/CHO showed a binding reaction which was higher than that of HV0LV3-1/CHO and similar to that of HV0LV3-3/CHO. Binding reaction of HV0LV3-3/CHO was lower than that of HV0LV3-1. From the above results, it was suggested that regarding the height of the binding reaction, the modification at position 14 or 15 functions more cooperatively than the modification at position 2, and modification at position 92 is essential for the recovery of the activity.

8. Measurement of Neutralization Activity of Anti-FGF-8 CDR-grafted Antibody for FGF-8

Evaluation of Neutralization Activity of the Anti-FGF-8 CDR-grafted Antibodies

Figure 21:
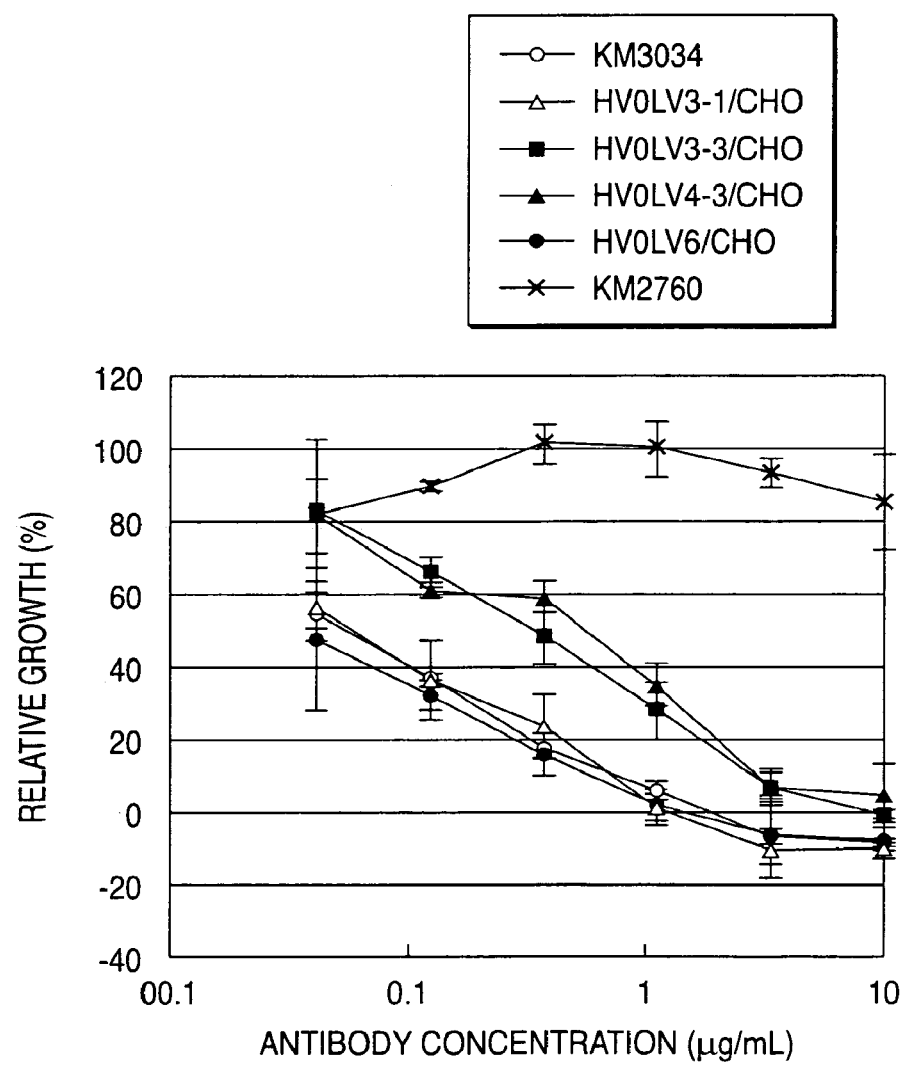
FIG. 21 shows neutralization activities of anti-FGF-8 chimeric antibody KM3034 and anti-FGF-8 CDR-grafted antibodies HV0LV3-1/CHO, HV0LV3-3/CHO, HV0LV4-3/CHO and HV0LV6/CHO on the FGF-8-dependent growth of mouse breast cancer cell line SC-3 cells. The abscissa and the ordinate show antibody concentration (µg/ml) and relative growth (%) when the growth by the addition of FGF-8 alone is defined as 100%, respectively. "○", "Δ", "■", "▲", "●" and "x" indicate activities of KM3034, HV0LV3-1/CHO, HV0LV3-3/CHO, HV0LV4-3/CHO, HV0LV6/CHO and KM2760 as a negative control, respectively.

HV0LV6/CHO and HV0LV3-1/CHO obtained in the item 5 of Example 5 and the anti-FGF-8 CDR-grafted antibodies HV0LV4-3/CHO and HV0LV3-3/CHO obtained in the item 5 of Example 6 was carried out in accordance with the method described in the item 5 of Example 4. The CHO/DG44 cell-derived anti-FGF-8 chimeric antibody KM3034 obtained in the item 3(1) of Example 3 was used as a positive control, and the chimeric antibody KM2760 for human chemokine CCR4 described in WO 01/64754 as a negative control. The results are shown in FIG. 21. As shown in FIG. 21, HV0LV6/CHO and HV0LV3-1/CHO showed similar FGF-8 neutralization activity to that of the chimeric antibody KM3034. On the other hand, HV0LV4-3/CHO and HV0LV3-3/CHO showed almost the same neutralization activity, and the activity was about 1/2 of that of the chimeric antibody KM3034. Neutralization activity of HV0LV3-1/CHO and HV0LV4-3/CHO showed no correlation with the height of the binding reaction by BIAcore, and it was suggested that the amino acid residue at position 2 and amino acid residues at positions 14 and 15 have independent influences on the binding activity for FGF-5 and the FGF-8 neutralization activity for cells.

Based on the above results of respective evaluations, the CHO/DG44 cell-derived CDR-grafted antibody HV0LV6/CHO which showed high binding reaction and FGF-8 neutralization activity similar to those of the chimeric antibody KM3034 was named KM8034, and the CHO/DG44 cell-derived transformed cell clone highly expressing KM8034 was named KM8034 in the same manner. Also, the CHO/DG44 cell-derived CDR-grafted antibody HV0LV4-3/CHO which showed high binding reaction similar to that of KM8034 was named KM8035, and the CHO/DG44 cell-derived transformed cell line highly expressing KM8035 was named KM8035 in the same manner. The VL amino acid sequence LV.4-3 of KM8035 is shown in SEQ ID NO:40. Furthermore, the transformed cell line KM8035 has been deposited on Jun. 20, 2002, as FERM BP-8082 in International Patent Organism Depositary, National Institute of Advanced Industrial Science and Technology (AMST Tsukuba Central 6, 1-1, Higashi I-Chome Tsukuba-shi, Ibaraki-ken 305-8566 Japan). In addition, the CHO/DG44 cell-derived CDR-grafted antibody HV0LV3-1/CHO which showed a high binding reaction similar to that of KM8034 was named KM8036, and the CHO/DG44 cell-derived transformed cell line highly expressing KM8036 was named KM8036 in the same manner. The amino acid sequence LV.3-1 of VL of KM8036 is shown in SEQ ID NO:41. Also, the transformed cell line KM8036 has been deposited on Jun. 20, 2002, as FERM BP-8083 in International Patent Organism Depositary, National Institute of Advanced Industrial Science and Technology (AIST Tsukuba Central 6, 1-1, Higashi I-Chome Tsukuba-shi, Ibaraki-ken 305-8566 Japan).

Since the anti-FGF-8 CDR-grafted antibody KM8034 shows high binding reaction and FGF-8 neutralization activity similar to those of the chimeric antibody KM3034, and the immunogenicity in human is reduced than the chimeric antibody, its therapeutic effects higher than the chimeric antibody is expected. Although there is a possibility that the binding activity and FGF-8 neutralization activity of the anti-FGF-8 CDR-grafted antibodies KM8036 and KM8035 are slightly reduced in comparison with KM8034, amino acid residues of the V region FR derived from the mouse antibody KM1334 are 3 residues and 4 residues, respectively, so that further reduced immunogenicity than the KM8034 is expected.

EXAMPLE 7

Evaluation of In Vivo Antitumor Effect of Antibody for FGF-8:

In vivo antitumor effect of KM1334 was evaluated using a nude mouse subcutaneous transplantation model of a mouse mammary tumor cell line SC-3. As a control antibody, KM511 was used. KM1334 and KM511 were prepared according to the method in Example 1 of the present application and that of *Agric. Biol. Chem.*, 53: 1095–1101 (1989), respectively.

1. Evaluation of Antitumor Effect in Early Stage Cancer Model

The SC-3 cells were suspended in PBS in a density of $1 \times 10^7$ cells/ml, and the suspension was subcutaneously transplanted under the left-side, back of male nude mice of 6 to 8 weeks of age (CLEA JAPAN, INC.) at 100 µl/head ($1 \times 10^6$ cells/head). Immediately after the transplantation, 100 µg/head, KM1334, 400 µg/head KM1334 or 400 µg/head KM511 was intraperitoneally administered into each of the tumor-transplanted mice. Each of the antibodies was administered by dissolving it in 100 μl of PBS. The antibodies were administered after 4, 7, 11, 14 and 18 days, in a total of 6 times. The results are shown in FIG. 22 as attached.

Figure 22:
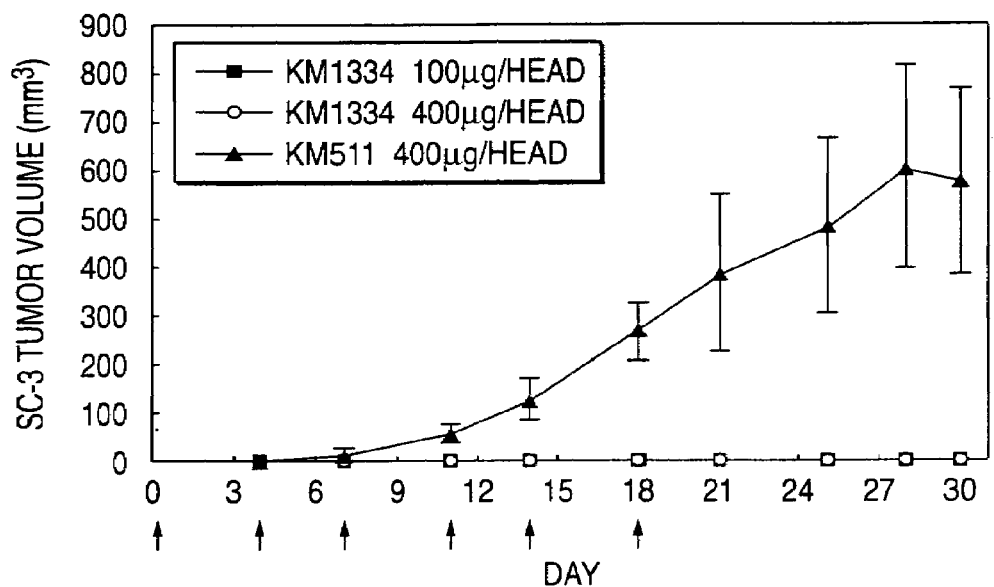
FIG. 22 shows tumor taking inhibition of KM1334 in the SC-3-transplanted nude mice. "↑" indicates the antibody-administered day, and "■", "○", and "▲" indicate tumor volumes in the 100 µg/head KM1334 administration group, in the 400 µg/head KM1334 administration group, and in the 400 µg/head KM511 administration group, respectively.

FIG. 22 shows tumor taking inhibition of KM1334 in the SC-3-transplanted nude mice. The symbol "↑" indicates the antibody-administered day, and the symbols "■", "○", and "▲" indicate tumor volumes in the 100 μg/head KM1334 administration group, in the 400 μg/head KM1334 administration group, and in the 400 μg/head KM511 administration group, respectively.

The tumor volume was measured periodically until 30 days after the tumor transplantation. As shown in FIG. 22, the tumor observed in the KM511 administration group was not found in each of the KM1334 administration groups, thus showing that KM1334 has a strong SC-3 tumor taking inhibition effect. Also, the length (L), width (W) and height (M) of the tumor were measured using a pair of calipers, and the tumor volume (V) was calculated by a formula of V (mm$^3$)=(L)×(W)×(H)×0.5326.

2. Evaluation of Antitumor Effect in Advanced Cancer Model

The SC-3 cells were suspended in PBS in a density of 1×10$^7$ cells/ml, and the suspension was subcutaneously transplanted under the left-side back of male nude mice of 6 to 8 weeks of age (CLEA JAPAN, INC.) at 100 μl/head (1×10$^6$ cells/head). Administration of the antibodies was started when the tumor volume became approximately 120 mm$^3$ (on the 13th day after the μmol transplantation). As the antibodies, 100 μg/head KM1334, 400 μg/head KM1334 or 400 μg/head KM511 was intraperitoneally administered into each of the tumor-transplanted mice. In this case, each of the antibodies was administered by dissolving it in 100 μl of PBS. The antibodies were administered on the 13th, 16th, 20th, 23rd, 27th, 30th, 34th and 37th days after the tumor transplantation, in a total of 8 times. The results are shown in FIG. 23 as attached.

Figure 23:
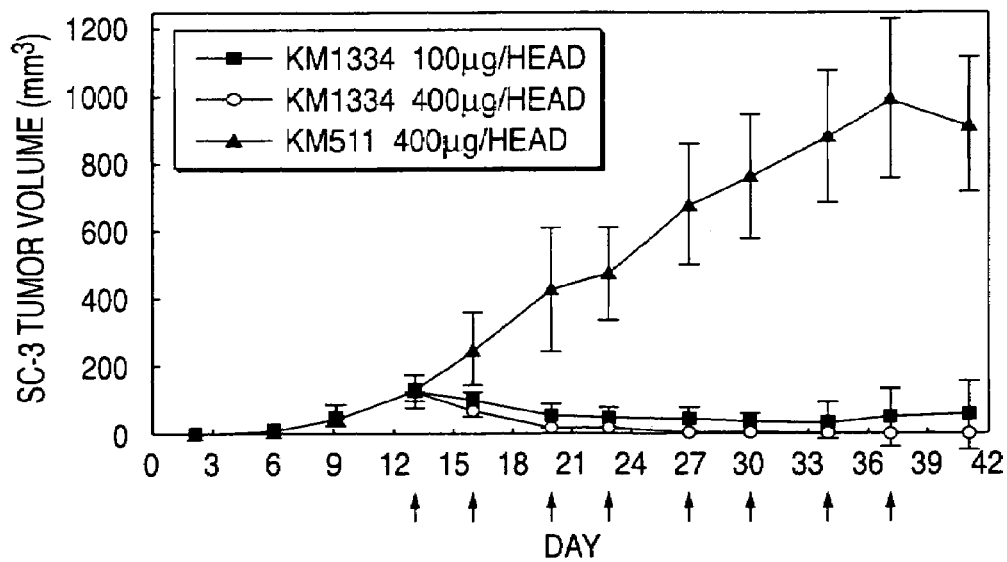
FIG. 23 shows tumor proliferation inhibition of KM1334 in the SC-3-transplanted nude mice. "↑" indicates the antibody-administered day, and "■", "○", and "▲" indicate tumor volumes in the 100 µg/head KM1334 administration group, in the 400 µg/head KM1334 administration group, and in the 400 µg/head KM511 administration group, respectively.

FIG. 23 shows tumor proliferation inhibition of KM1334 in the SC-3-transplanted nude mice. The symbol "↑" indicates the antibody-administered day, and the symbols "■", "○", and "▲" indicate tumor volumes in the 100 μg/head KM1334 administration group, in the 400 μg/head KM1334 administration group, and in the 400 μg/head KM511 administration group, respectively.

The tumor volume was measured periodically until 41st day after the tumor transplantation. As shown in FIG. 23, reduction of tumor was already observed on the 3rd day after the administration of the antibody in each of the KM1334 administration groups, and particularly in the 400 μg/head administration group, the tumor was reduced to traces after a lapse of 8 days and reached a value of T/C<0.001 after a lapse of 41 days. On the other hand, increase in the tumor volume was continued in the KM511 administration group. Based on these results, it was revealed that KM1334 has a strong tumor reducing effect upon SC-3.

While the invention has been described in detail and with reference to specific embodiments thereof, it will be apparent to one skilled in the art that various changes and modifications can be made therein without departing from the spirit and scope thereof.

This application is based on application No. Hei 8-81754 filed in Japan, the content of which is incorporated hereinto by reference.

What is claimed is:

1. A method for treating a prostate cancer or breast cancer, comprising administering to human or animal in need of such treatment an effective amount of a monoclonal antibody which specifically binds to fibroblast growth factor-8 (FGF-8) and inhibits activity of FGF-8.

2. The method according to claim 1, wherein the monoclonal antibody is a monoclonal antibody which specifically binds to SEQ ID NO:1.

3. The method according to claim 1, wherein the monoclonal antibody is a humanized antibody or the antigen binding fragment thereof.

4. The method according to claim 3, wherein the antibody comprises CDR1, CDR2 and CDR3 of an antibody heavy chain (H chain) variable region (V region) comprising the amino acid sequences represented by SEQ ID NOs: 7, 8 and 9, respectively, and CDR1, CDR2 and CDR3 of an antibody light chain (L chain) variable region (V region) comprising the amino acid sequences represented by SEQ ID NOs: 10, 11 and 12, respectively.

5. The method according to claim 3, wherein the humanized antibody is a human chimeric antibody or a human CDR-grafted antibody.

6. The method according to claim 5, wherein the human chimeric antibody comprises a heavy chain (H chain) variable region (V region) and a light chain (L chain) V region of a monoclonal antibody against FGF-8.

7. The method according to claim 5, wherein the human chimeric antibody comprises a heavy chain (H chain) variable region (V region) and a light chain (L chain) V region of a monoclonal antibody against FGF-8, and an H chain constant region (C region) and an L chain C region of a human antibody.

8. The method according to claim 4, wherein VH of the antibody comprises an amino acid sequence represented by SEQ ID NO:42.

9. The method according to claim 4, wherein VL of the antibody comprises an amino acid sequence represented by SEQ ID NO:43.

10. The method according to claim 4, wherein VH and VL of the antibody comprise amino acid sequences represented by SEQ ID NOs:42 and 43, respectively.

11. The method according to claim 5, wherein the human CDR-grafted antibody comprises CDRs of VH and VL of a monoclonal antibody against FGF-8.

12. The method according to claim 5, wherein the human CDR-grafted antibody comprises CDRs of VH and VL of a monoclonal antibody against FGF-8, and framework regions (FRs) of VH and VL of a human antibody.

13. The method according to claim 5, wherein the human CDR-grafted antibody comprises CDRs of VH and VL of a monoclonal antibody against FGF-8, and an H chain C region and an L chain C region of a human antibody.

14. The method according to claim 5, wherein CDR1, CDR2 and CDR3 of VH of the antibody comprises amino acid sequences represented by SEQ ID NOs:7, 8 and 9, respectively, and wherein CDR1, CDR2 and CDR3 of VL of the antibody comprises amino acid sequences represented by SEQ ID NOs:10, 11 and 12, respectively.

15. The method according to claim 4, wherein VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:18 is substituted.

16. The method according to claim 4, wherein VL of the antibody comprises an amino acid sequence in which at least one amino acid residue selected from lie at position 2, Val at position 3, Thr at position 14, Pro at position 15, Gin at position 50, Leu at position 51 and Tyr at position 92 in the amino acid sequence represented by SEQ ID NO:19 is substituted.

17. The method according to claim 4, wherein VH of the antibody comprises an amino acid sequence in which at least one amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 in the amino acid sequence represented by SEQ ID NO:18 is substituted, and wherein VL of the antibody comprises an amino acid sequence in which at least one amino acid residue selected from lie at position 2, Val at position 3, Thr at position 14, Pro at position 15, Gin at position 50, Leu at position 51 and Tyr at position 92 in the amino acid sequence represented by SEQ ID NO:19 is substituted.

18. The method according to claim 4, wherein VH of the antibody comprises the amino acid sequence represented by SEQ ID NO:18 or 20.

19. The method according to claim 4, wherein VL of the antibody comprises the amino acid sequence represented by SEQ ID NO:19, 21, 40 or 41.

20. The method according to claim 4, wherein VH of the antibody comprises the amino acid sequence represented by SEQ ID NO:18 or 20, and wherein VL of the antibody comprises the amino acid sequence represented by SEQ ID NO:19, 21, 40 or 41.

21. The method according to claim 4, wherein VH and VL of the antibody comprise amino acid sequences represented by SEQ ID NOs:18 and 21, respectively.

22. The method according to claim 4, wherein VH and VL of the antibody comprise amino acid sequences represented by SEQ ID NOs:18 and 40, respectively.

23. The method according to claim 4, wherein VH and VL of the antibody comprise amino acid sequences represented by SEQ ID NOs:18 and 41, respectively.

24. The method according to claim 3, wherein the antigen binding fragment is selected from the group consisting of Fab, Fab', F(ab')$_2$, a single chain antibody (scFv), a dimerized variable region (V region) fragment (diabody), a disulfide-stabilized V region fragment (dsFv) and a peptide comprising a complementary determining region (CDR).

25. The method according to claim 1, wherein the monoclonal antibody is a monoclonal antibody belonging to the IgG1 subclass produced by hybridoma FERM BP-5451.

26. The method according to claim 4, wherein the monoclonal antibody is a humanized antibody produced by a transformant FERM BP-7836, FERM BP-8082, FERM BP-8083 or FERM BP-8084.

* * * * *